(12) United States Patent
LaChapelle

(10) Patent No.: US 10,551,501 B1
(45) Date of Patent: Feb. 4, 2020

(54) DUAL-MODE LIDAR SYSTEM

(71) Applicant: LUMINAR TECHNOLOGIES, INC., Orlando, FL (US)

(72) Inventor: Joseph G. LaChapelle, Philomath, OR (US)

(73) Assignee: Luminar Technologies, Inc., Orlando, FL (US)

(*) Notice: Subject to any disclaimer, the term of this patent is extended or adjusted under 35 U.S.C. 154(b) by 0 days.

(21) Appl. No.: 16/059,638

(22) Filed: Aug. 9, 2018

(51) Int. Cl.
*G01S 17/10* (2006.01)
*G01S 17/58* (2006.01)
*G01N 21/47* (2006.01)
*G02B 26/12* (2006.01)
*G01S 17/93* (2006.01)

(52) U.S. Cl.
CPC .............. *G01S 17/10* (2013.01); *G01N 21/47* (2013.01); *G01S 17/58* (2013.01); *G01S 17/93* (2013.01); *G02B 26/121* (2013.01)

(58) Field of Classification Search
CPC ........ G01S 17/10; G01S 7/484; G01S 17/936; G01S 7/497; G01S 17/42; G01S 17/89; G01S 7/4808; G01S 17/023; G08G 1/16
See application file for complete search history.

(56) References Cited

U.S. PATENT DOCUMENTS

| 5,006,721 A | 4/1991 | Cameron et al. |
| 6,449,384 B2 | 9/2002 | Laumeyer et al. |
| 6,710,324 B2 | 3/2004 | Hipp |
| 6,723,975 B2 | 4/2004 | Saccomanno |
| 6,747,747 B2 | 6/2004 | Hipp |
| 6,759,649 B2 | 7/2004 | Hipp |
| 7,092,548 B2 | 8/2006 | Laumeyer et al. |
| 7,209,221 B2 | 4/2007 | Breed et al. |
| 7,345,271 B2 | 3/2008 | Boehlau et al. |
| 7,443,903 B2 | 10/2008 | Leonardo et al. |
| 7,532,311 B2 | 5/2009 | Henderson et al. |
| 7,570,793 B2 | 8/2009 | Lages et al. |
| 7,583,364 B1 | 9/2009 | Mayor et al. |
| 7,649,920 B2 | 1/2010 | Welford |
| 7,652,752 B2 | 1/2010 | Fetzer et al. |
| 7,839,491 B2 | 11/2010 | Harris et al. |
| 7,872,794 B1 | 1/2011 | Minelly et al. |
| 7,902,570 B2 | 3/2011 | Itzler et al. |
| 7,945,408 B2 | 5/2011 | Dimsdale et al. |

(Continued)

FOREIGN PATENT DOCUMENTS

WO    WO-2013/087799 A1    6/2013

*Primary Examiner* — Luke D Ratcliffe

(57) ABSTRACT

A method in a lidar system comprises emitting a pulse of light, detecting at least a portion of the emitted pulse of light scattered by a target located a distance from the lidar system, and determining the distance from the lidar system to the target based at least in part on a round-trip time of flight for the emitted pulse of light to travel from the lidar system to the target and back to the lidar system. The method further comprises emitting a series of pulses of light having particular pulse-frequency characteristics, detecting at least a portion of the series of emitted pulses of light scattered by the target, and comparing the pulse-frequency characteristics of the series of emitted pulses of light with corresponding pulse-frequency characteristics of the detected series of scattered pulses of light to determine a velocity of the target with respect to the lidar system.

24 Claims, 23 Drawing Sheets

(56) References Cited

U.S. PATENT DOCUMENTS

| | | |
|---|---|---|
| 7,969,558 B2 | 6/2011 | Hall |
| 7,995,796 B2 | 8/2011 | Retterath et al. |
| 8,059,263 B2 | 11/2011 | Haberer et al. |
| 8,072,663 B2 | 12/2011 | O'Neill et al. |
| 8,081,301 B2 | 12/2011 | Stann et al. |
| 8,138,849 B2 | 3/2012 | West et al. |
| 8,279,420 B2 | 10/2012 | Ludwig et al. |
| 8,280,623 B2 | 10/2012 | Trepagnier et al. |
| 8,346,480 B2 | 1/2013 | Trepagnier et al. |
| 8,364,334 B2 | 1/2013 | Au et al. |
| 8,452,561 B2 | 5/2013 | Dimsdale et al. |
| 8,548,014 B2 | 10/2013 | Fermann et al. |
| 8,625,080 B2 | 1/2014 | Heizmann et al. |
| 8,675,181 B2 | 3/2014 | Hall |
| 8,723,955 B2 | 5/2014 | Kiehn et al. |
| 8,767,190 B2 | 7/2014 | Hall |
| 8,796,605 B2 | 8/2014 | Mordarski et al. |
| 8,836,922 B1 | 9/2014 | Pennecot et al. |
| 8,880,296 B2 | 11/2014 | Breed |
| 8,896,818 B2 | 11/2014 | Walsh et al. |
| 8,934,509 B2 | 1/2015 | Savage-Leuchs et al. |
| 9,000,347 B2 | 4/2015 | Woodward et al. |
| 9,041,136 B2 | 5/2015 | Chia |
| 9,048,370 B1 | 6/2015 | Urmson et al. |
| 9,063,549 B1 | 6/2015 | Pennecot et al. |
| 9,069,060 B1 | 6/2015 | Zbrozek et al. |
| 9,074,878 B2 | 7/2015 | Steffey et al. |
| 9,086,273 B1 | 7/2015 | Gruver et al. |
| 9,086,481 B1 | 7/2015 | Dowdall et al. |
| 9,091,754 B2 | 7/2015 | d'Aligny |
| 9,103,669 B2 | 8/2015 | Giacotto et al. |
| 9,121,703 B1 | 9/2015 | Droz et al. |
| 9,160,140 B2 | 10/2015 | Gusev et al. |
| 9,170,333 B2 | 10/2015 | Mheen et al. |
| 9,199,641 B2 | 12/2015 | Ferguson et al. |
| 9,213,085 B2 | 12/2015 | Kanter |
| 9,239,260 B2 | 1/2016 | Bayha et al. |
| 9,246,041 B1 | 1/2016 | Clausen et al. |
| 9,285,464 B2 | 3/2016 | Pennecot et al. |
| 9,285,477 B1 | 3/2016 | Smith et al. |
| 9,297,901 B2 | 3/2016 | Bayha et al. |
| 9,299,731 B1 | 3/2016 | Lenius et al. |
| 9,304,154 B1 | 4/2016 | Droz et al. |
| 9,304,203 B1 | 4/2016 | Droz et al. |
| 9,304,316 B2 | 4/2016 | Weiss et al. |
| 9,310,471 B2 | 4/2016 | Sayyah et al. |
| 9,335,255 B2 | 5/2016 | Retterath et al. |
| 9,360,554 B2 | 6/2016 | Retterath et al. |
| 9,368,933 B1 | 6/2016 | Nijjar et al. |
| 9,383,201 B2 | 7/2016 | Jachman et al. |
| 9,383,445 B2 | 7/2016 | Lu et al. |
| 9,383,753 B1 | 7/2016 | Templeton et al. |
| RE46,672 E | 1/2018 | Hall |
| 2006/0290920 A1 | 12/2006 | Kampchen et al. |
| 2007/0115541 A1* | 5/2007 | Rogers ............... H01S 3/06754 359/345 |
| 2009/0273770 A1 | 11/2009 | Bauhahn et al. |
| 2010/0034221 A1 | 2/2010 | Dragic |
| 2012/0227263 A1 | 9/2012 | Leclair et al. |
| 2013/0033742 A1 | 2/2013 | Rogers et al. |
| 2014/0111805 A1 | 4/2014 | Albert et al. |
| 2014/0168631 A1 | 6/2014 | Haslim et al. |
| 2014/0176933 A1 | 6/2014 | Haslim et al. |
| 2014/0211194 A1 | 7/2014 | Pacala et al. |
| 2014/0293263 A1 | 10/2014 | Justice et al. |
| 2014/0293266 A1 | 10/2014 | Hsu et al. |
| 2015/0131080 A1 | 5/2015 | Retterath et al. |
| 2015/0177368 A1 | 6/2015 | Bayha et al. |
| 2015/0185244 A1 | 7/2015 | Inoue et al. |
| 2015/0185313 A1 | 7/2015 | Zhu |
| 2015/0192676 A1 | 7/2015 | Kotelnikov et al. |
| 2015/0192677 A1 | 7/2015 | Yu et al. |
| 2015/0204978 A1 | 7/2015 | Hammes et al. |
| 2015/0214690 A1 | 7/2015 | Savage-Leuchs et al. |
| 2015/0301182 A1 | 10/2015 | Geiger et al. |
| 2015/0323654 A1 | 11/2015 | Jachmann et al. |
| 2015/0378023 A1 | 12/2015 | Royo Royo et al. |
| 2015/0378241 A1 | 12/2015 | Eldada |
| 2016/0003946 A1* | 1/2016 | Gilliland ............... G01S 17/10 356/5.01 |
| 2016/0025842 A1 | 1/2016 | Anderson et al. |
| 2016/0047896 A1 | 2/2016 | Dussan |
| 2016/0047901 A1 | 2/2016 | Pacala et al. |
| 2016/0049765 A1 | 2/2016 | Eldada |
| 2016/0146939 A1 | 5/2016 | Shpunt et al. |
| 2016/0146940 A1 | 5/2016 | Koehler |
| 2016/0161600 A1 | 6/2016 | Eldada et al. |
| 2016/0245919 A1 | 8/2016 | Kalscheur et al. |
| 2018/0032042 A1 | 2/2018 | Turpin et al. |
| 2018/0180739 A1 | 6/2018 | Droz |
| 2018/0306927 A1* | 10/2018 | Slutsky ............... G01S 17/10 |

\* cited by examiner

DUAL-MODE LIDAR SYSTEM

FIELD OF TECHNOLOGY

This disclosure generally relates to lidar systems and, more particularly, detecting both the distance to a target and a velocity of the target.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Light detection and ranging (lidar) is a technology that can be used to measure distances to remote targets. Typically, a lidar system includes a light source and an optical receiver. The light source can be, for example, a laser which emits light having a particular operating wavelength. The operating wavelength of a lidar system may lie, for example, in the infrared, visible, or ultraviolet portions of the electromagnetic spectrum. The light source emits light toward a target which then scatters the light. Some of the scattered light is received back at the receiver. The system determines the distance to the target based on one or more characteristics associated with the returned light. For example, the system may determine the distance to the target based on the time of flight of a returned light pulse. However, a pulsed lidar system generally cannot determine the velocity of a target based on the returned light pulse.

SUMMARY

According to one implementation, a method comprises emitting, by a light source of a lidar system, a pulse of light; detecting, by a receiver of the lidar system, at least a portion of the emitted pulse of light scattered by a target located a distance from the lidar system; determining, by a processor of the lidar system, the distance from the lidar system to the target based at least in part on a round-trip time of flight for the emitted pulse of light to travel from the lidar system to the target and back to the lidar system; emitting, by the light source, a series of pulses of light having particular pulse-frequency characteristics; detecting, by the receiver, at least a portion of the series of emitted pulses of light scattered by the target; and comparing, by a comparison module, the pulse-frequency characteristics of the series of emitted pulses of light with corresponding pulse-frequency characteristics of the detected series of scattered pulses of light to determine a velocity of the target with respect to the lidar system.

Another embodiment of the techniques of this disclosure is lidar system comprising a light source configured to emit a pulse of light; a receiver configured to detect at least a portion of the emitted pulse of light scattered by a target located a distance from the lidar system; and a processor configured to determine the distance from the lidar system to the target based at least in part on a round-trip time of flight for the emitted pulse of light to travel from the lidar system to the target and back to the lidar system. The light source is further configured, in response to determining the distance to the target, to emit a series of pulses of light having particular pulse-frequency characteristics. The receiver is further configured to detect at least a portion of the series of emitted pulses of light scattered by the target. The lidar system further comprises a comparator module configured to compare the pulse-frequency characteristics of the series of emitted pulses of light with corresponding pulse-frequency characters of the detected series of scattered pulses of light to determine a velocity of the target with respect to the lidar system.

Yet another embodiment is a method comprising emitting, by a light source, a series of pulses of light having particular pulse-frequency characteristics; detecting, by a receiver of the lidar system, at least a portion of the series of emitted pulses of light scattered by scattered by a target located a distance from the lidar system; determining, by a processor of the lidar system, the distance from the lidar system to the target based at least in part on a round-trip time of flight for the emitted series of pulses of light to travel from the lidar system to the target and back to the lidar system; and comparing, by a comparison module, the pulse-frequency characteristics of the series of emitted pulses of light with corresponding pulse-frequency characteristics of the detected series of scattered pulses of light to determine a velocity of the target with respect to the lidar system.

DETAILED DESCRIPTION

Figure 1:
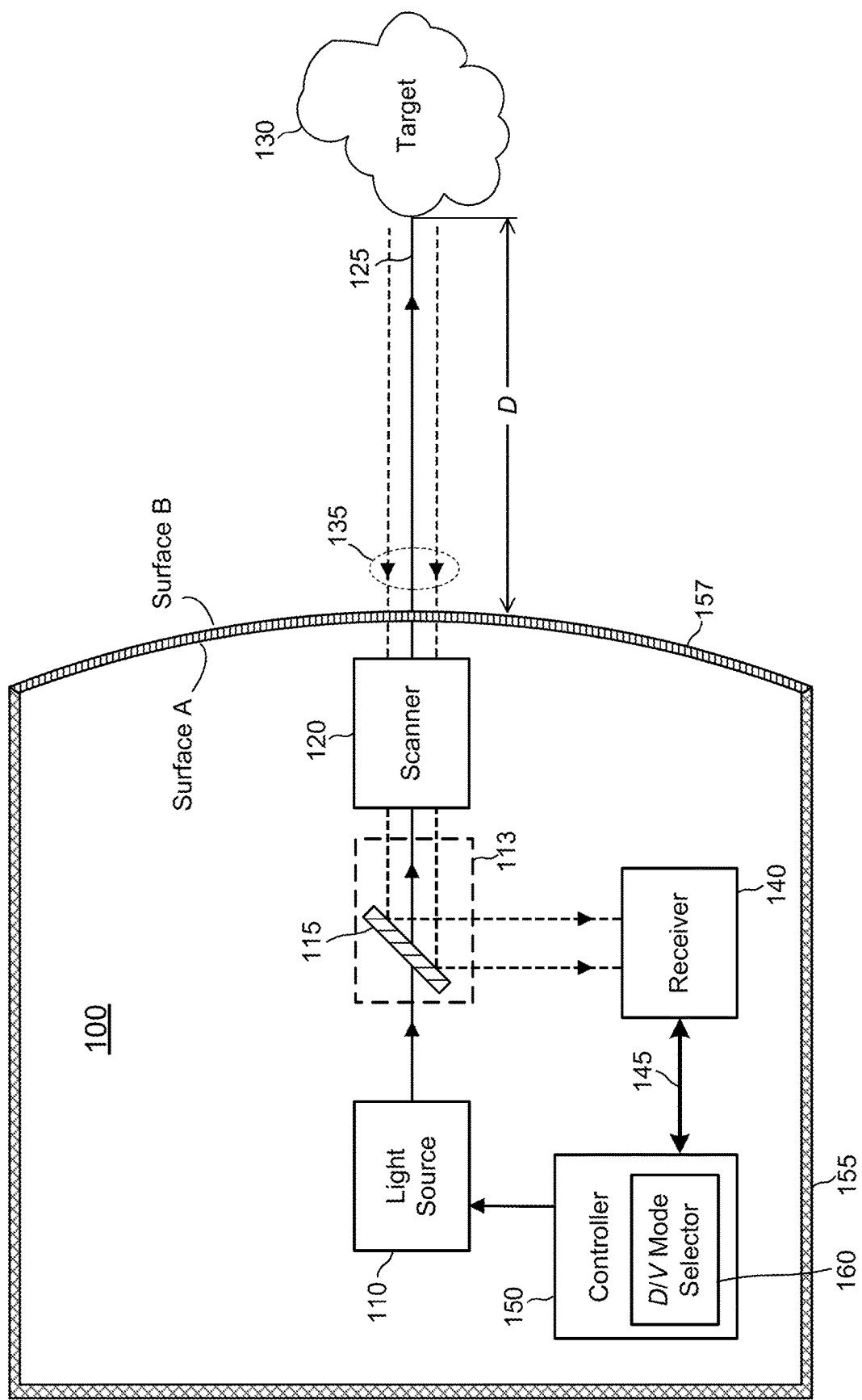
FIG. 1 is a block diagram of an example dual-mode light detection and ranging (lidar) system capable of detecting both distances to targets and velocities of targets, implemented according to one embodiment of the techniques of this disclosure.

A dual-mode lidar of system of this disclosure can generate pulses of light to determine a distance to a target as well as the velocity of the target relative to the lidar system. The dual-mode lidar system has at least two operational modes: in the first mode, the system emits an individual pulse of light, detects light scattered by a remote target and corresponding to the individual pulse of light (e.g., having the same wavelength), and determines the distance to the target based on the time it took the scattered light to reach the lidar system; in the second mode, the system generates a burst (a series, a train) of pulses with certain pulse-frequency characteristics, such as a constant separation between successive pulses, and determines the velocity of the target based on the change in this characteristic (e.g., the frequency shift due to the Doppler effect). The dual-mode lidar system in both cases operates as a pulsed lidar system.

Alternatively, to determine the velocity of a target, a frequency-modulated continuous-wave (FM CW) lidar system can use frequency-modulated coherent light (e.g., from a frequency-stable CW laser). Such a system can determine the velocity of a target based on the Doppler effect by determining by how much the frequency of the light scattered by the object is shifted due to the relative velocity of the object. However, when a lidar system is pulsed rather than continuous-wave-based, the system generally cannot determine velocity based on the Doppler effect because it may not be practical (or possible) to perform coherent detection with a pulsed light source (e.g., it is difficult to store a portion of an emitted pulse to interfere with scattered light from the emitted pulse).

As discussed in more detail below, the dual-mode lidar system of this disclosure addresses these issues by using particular characteristics of bursts of pulses. Because this system determines velocity using a quasi-Doppler effect that does not require optical coherence, this lidar system can be described as a non-coherent pulsed Doppler system.

The dual-mode lidar system in some cases operates according to the two modes during the same ranging event by first emitting a pulse of light to determine a distance to a target and, immediately upon receiving a return corresponding to the emitted pulse, emitting a pulse train to determine the velocity of the target. Both the distance measurement and the velocity measurement can be provided as respective properties of the same pixel in a point-cloud. The dual-mode lidar system thus can eliminate lag time between distance and velocity measurements almost entirely. Moreover, by conducting distance and velocity measurements using the same optical path, the dual-model lidar system eliminates optical misalignment between the two measurements (whereas using two different instruments to determine distance and velocity produces offsets between measurements).

In another implementation, the dual-mode lidar system can operate in different modes during different ranging events, so as to maximize the distance at which the system can determine the velocity of a target. As a more specific example, the dual-mode lidar system can measure the distance for a certain pixel and the velocity for the adjacent pixel, with the entire duration of a ranging event allocated to a single measurement of distance or velocity. This approach may be useful when a controller of the dual-mode lidar system or of the vehicle has previously determined that the two pixels likely cover the same remote target.

Depending on the implementation, the dual-mode lidar system can operate at the same wavelength in the two modes or at different wavelengths. Further, the dual-mode lidar system in some cases imparts a pattern to the pulse train so as to check whether the return signal corresponds to the imparted pattern, transformed due to the Doppler effect when the target is moving, as discussed above. The dual-mode lidar system in this manner can reduce cross-talk, or erroneous detections of light from other lidar systems.

Still further, a dual-mode lidar system in some implementations transitions to the velocity-detection mode only in response to determining that one or more conditions are satisfied, such as sufficient time remaining in the ranging event or the target being disposed within a certain distance, prior results of processing the field of regard indicating that the target is a of a certain type, the scan angle being within a certain range, etc.

An example lidar system in which these techniques can be implemented is considered next with reference to FIGS. 1-5, followed by a discussion of the techniques which the lidar system can implement to scan a field of regard and generate individual pixels (FIGS. 6-9). An example implementation in a vehicle is then discussed with reference to FIGS. 10 and 11, and example photo detector and pulse-detection circuit are discussed with reference to FIGS. 12 and 13. Example scenarios in which a lidar system of this disclosure can determine velocities of targets are discussed with reference to FIG. 14-16, and the techniques this lidar system can implement to operate in the two modes are discussed with reference to FIGS. 17-25.

System Overview

FIG. 1 illustrates an example light detection and ranging (lidar) system 100. The lidar system 100 may be referred to as a laser ranging system, a laser radar system, a LIDAR system, a lidar sensor, or a laser detection and ranging (LADAR or ladar) system. The lidar system 100 may include a light source 110, a mirror 115, a scanner 120, a receiver 140, and a controller 150. The light source 110 may be, for example, a laser which emits light having a particular operating wavelength in the infrared, visible, or ultraviolet portions of the electromagnetic spectrum. As a more specific example, the light source 110 may include a laser with an operating wavelength between approximately 1.2 μm and 1.7 μm.

In operation, the light source 110 emits an output beam of light 125 which may be continuous-wave, pulsed, or modulated in any suitable manner for a given application. The output beam of light 125 is directed downrange toward a remote target 130 located a distance D from the lidar system 100 and at least partially contained within a field of regard of the system 100. Depending on the scenario and/or the implementation of the lidar system 100, D can be between 1 m and 1 km, for example.

Once the output beam 125 reaches the downrange target 130, the target 130 may scatter or, in some cases, reflect at least a portion of light from the output beam 125, and some of the scattered or reflected light may return toward the lidar system 100. In the example of FIG. 1, the scattered or reflected light is represented by input beam 135, which passes through the scanner 120, which may be referred to as a beam scanner, optical scanner, or laser scanner. The input beam 135 passes through the scanner 120 to the mirror 115, which may be referred to as an overlap mirror, superposition mirror, or beam-combiner mirror. The mirror 115 in turn directs the input beam 135 to the receiver 140. The input 135 may contain only a relatively small fraction of the light from the output beam 125. For example, the ratio of average power, peak power, or pulse energy of the input beam 135 to average power, peak power, or pulse energy of the output beam 125 may be approximately $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, or $10^{-12}$. As another example, if a pulse of the output beam 125 has a pulse energy of 1 microjoule (μJ), then the pulse energy of a corresponding pulse of the input beam 135 may have a pulse energy of approximately 10 nanojoules (nJ), 1 nJ, 100 picojoules (pJ), 10 pJ, 1 pJ, 100 femtojoules (fJ), 10 fJ, 1 fJ, 100 attojoules (aJ), 10 aJ, or 1 aJ.

The output beam 125 may be referred to as a laser beam, light beam, optical beam, emitted beam, or just beam; and the input beam 135 may be referred to as a return beam, received beam, return light, received light, input light, scattered light, or reflected light. As used herein, scattered light may refer to light that is scattered or reflected by the target 130. The input beam 135 may include light from the output beam 125 that is scattered by the target 130, light from the output beam 125 that is reflected by the target 130, or a combination of scattered and reflected light from target 130.

The operating wavelength of a lidar system 100 may lie, for example, in the infrared, visible, or ultraviolet portions of the electromagnetic spectrum. The Sun also produces light in these wavelength ranges, and thus sunlight can act as background noise which can obscure signal light detected by the lidar system 100. This solar background noise can result in false-positive detections or can otherwise corrupt measurements of the lidar system 100, especially when the receiver 140 includes SPAD detectors (which can be highly sensitive).

Generally speaking, the light from the Sun that passes through the Earth's atmosphere and reaches a terrestrial-based lidar system such as the system 100 can establish an optical background noise floor for this system. Thus, in order for a signal from the lidar system 100 to be detectable, the signal must rise above the background noise floor. It is generally possible to increase the signal-to-noise (SNR) ratio of the lidar system 100 by raising the power level of the output beam 125, but in some situations it may be desirable to keep the power level of the output beam 125 relatively low. For example, increasing transmit power levels of the output beam 125 can result in the lidar system 100 not being eye-safe.

In some implementations, the lidar system 100 operates at one or more wavelengths between approximately 1400 nm and approximately 1600 nm. For example, the light source 110 may produce light at approximately 1550 nm.

In some implementations, the lidar system 100 operates at frequencies at which atmospheric absorption is relatively low. For example, the lidar system 100 can operate at wavelengths in the approximate ranges from 980 nm to 1110 nm or from 1165 nm to 1400 nm.

In other implementations, the lidar system 100 operates at frequencies at which atmospheric absorption is high. For example, the lidar system 100 can operate at wavelengths in the approximate ranges from 930 nm to 980 nm, from 1100 nm to 1165 nm, or from 1400 nm to 1460 nm.

According to some implementations, the lidar system 100 can include an eye-safe laser, or the lidar system 100 can be classified as an eye-safe laser system or laser product. An eye-safe laser, laser system, or laser product may refer to a system with an emission wavelength, average power, peak power, peak intensity, pulse energy, beam size, beam divergence, exposure time, or scanned output beam such that emitted light from the system presents little or no possibility of causing damage to a person's eyes. For example, the light source 110 or lidar system 100 may be classified as a Class 1 laser product (as specified by the 60825-1 standard of the International Electrotechnical Commission (IEC)) or a Class I laser product (as specified by Title 21, Section 1040.10 of the United States Code of Federal Regulations (CFR)) that is safe under all conditions of normal use. In some implementations, the lidar system 100 may be classified as an eye-safe laser product (e.g., with a Class 1 or Class I classification) configured to operate at any suitable wavelength between approximately 1400 nm and approximately 2100 nm. In some implementations, the light source 110 may include a laser with an operating wavelength between approximately 1400 nm and approximately 1600 nm, and the lidar system 100 may be operated in an eye-safe manner.

In some implementations, the light source 110 or the lidar system 100 may be an eye-safe laser product that includes a scanned laser with an operating wavelength between approximately 1530 nm and approximately 1560 nm. In some implementations, the lidar system 100 may be a Class 1 or Class I laser product that includes a fiber laser or solid-state laser with an operating wavelength between approximately 1400 nm and approximately 1600 nm.

The receiver 140 may receive or detect photons from the input beam 135 and generate one or more representative signals. For example, the receiver 140 may generate an output electrical signal 145 that is representative of the input beam 135. The receiver may send the electrical signal 145 to the controller 150. Depending on the implementation, the controller 150 may include one or more processors, an application-specific integrated circuit (ASIC), a field-programmable gate array (FPGA), and/or other suitable circuitry configured to analyze one or more characteristics of the electrical signal 145 to determine one or more characteristics of the target 130, such as its distance downrange from the lidar system 100. More particularly, the controller 150 may analyze the time of flight or phase modulation for the beam of light 125 transmitted by the light source 110. If the lidar system 100 measures a time of flight of T (e.g., T represents a round-trip time of flight for an emitted pulse of light to travel from the lidar system 100 to the target 130 and back to the lidar system 100), then the distance D from the target 130 to the lidar system 100 may be expressed as $D=c \cdot T/2$, where c is the speed of light (approximately $3.0 \times 10^8$ m/s).

As a more specific example, if the lidar system 100 measures the time of flight to be T=300 ns, then the lidar system 100 can determine the distance from the target 130 to the lidar system 100 to be approximately D=45.0 m. As another example, the lidar system 100 measures the time of flight to be T=1.33 µs and accordingly determines that the distance from the target 130 to the lidar system 100 is approximately D=199.5 m. The distance D from lidar system 100 to the target 130 may be referred to as a distance, depth, or range of the target 130. As used herein, the speed of light c refers to the speed of light in any suitable medium, such as for example in air, water, or vacuum. The speed of light in vacuum is approximately $2.9979 \times 10^8$ m/s, and the speed of light in air (which has a refractive index of approximately 1.0003) is approximately $2.9970 \times 10^8$ m/s.

The target 130 may be located a distance D from the lidar system 100 that is less than or equal to a maximum range $R_{MAX}$ of the lidar system 100. The maximum range $R_{MAX}$ (which also may be referred to as a maximum distance) of a lidar system 100 may correspond to the maximum distance over which the lidar system 100 is configured to sense or identify targets that appear in a field of regard of the lidar system 100. The maximum range of lidar system 100 may be any suitable distance, such as for example, 25 m, 50 m, 100 m, 200 m, 500 m, or 1 km. As a specific example, a lidar system with a 200-m maximum range may be configured to sense or identify various targets located up to 200 m away. For a lidar system with a 200-m maximum range ($R_{MAX}$=200 m), the time of flight corresponding to the maximum range is approximately $2 \cdot R_{MAX}/c \cong 1.33$ µs.

In some implementations, the light source 110, the scanner 120, and the receiver 140 may be packaged together within a single housing 155, which may be a box, case, or enclosure that holds or contains all or part of a lidar system 100. The housing 155 includes a window 157 through which the beams 125 and 135 pass. In one example implementation, the lidar-system housing 155 contains the light source 110, the overlap mirror 115, the scanner 120, and the receiver 140 of a lidar system 100. The controller 150 may reside within the same housing 155 as the components 110, 120, and 140, or the controller 150 may reside remotely from the housing.

Moreover, in some implementations, the housing 155 includes multiple lidar sensors, each including a respective scanner and a receiver. Depending on the particular implementation, each of the multiple sensors can include a separate light source or a common light source. The multiple sensors can be configured to cover non-overlapping adjacent fields of regard or partially overlapping fields of regard, depending on the implementation.

The housing 155 may be an airtight or watertight structure that prevents water vapor, liquid water, dirt, dust, or other contaminants from getting inside the housing 155. The housing 155 may be filled with a dry or inert gas, such as for example dry air, nitrogen, or argon. The housing 155 may include one or more electrical connections for conveying electrical power or electrical signals to and/or from the housing.

The window 157 may be made from any suitable substrate material, such as for example, glass or plastic (e.g., polycarbonate, acrylic, cyclic-olefin polymer, or cyclic-olefin copolymer). The window 157 may include an interior surface (surface A) and an exterior surface (surface B), and surface A or surface B may include a dielectric coating having particular reflectivity values at particular wavelengths. A dielectric coating (which may be referred to as a thin-film coating, interference coating, or coating) may include one or more thin-film layers of dielectric materials (e.g., $SiO_2$, $TiO_2$, $Al_2O_3$, $Ta_2O_5$, $MgF_2$, $LaF_3$, or $AlF_3$) having particular thicknesses (e.g., thickness less than 1 µm) and particular refractive indices. A dielectric coating may be deposited onto surface A or surface B of the window 157 using any suitable deposition technique, such as for example, sputtering or electron-beam deposition.

The dielectric coating may have a high reflectivity at a particular wavelength or a low reflectivity at a particular wavelength. A high-reflectivity (HR) dielectric coating may have any suitable reflectivity value (e.g., a reflectivity greater than or equal to 80%, 90%, 95%, or 99%) at any suitable wavelength or combination of wavelengths. A low-reflectivity dielectric coating (which may be referred to as an anti-reflection (AR) coating) may have any suitable reflectivity value (e.g., a reflectivity less than or equal to 5%, 2%, 1%, 0.5%, or 0.2%) at any suitable wavelength or combination of wavelengths. In particular embodiments, a dielectric coating may be a dichroic coating with a particular combination of high or low reflectivity values at particular wavelengths. For example, a dichroic coating may have a reflectivity of less than or equal to 0.5% at approximately 1550-1560 nm and a reflectivity of greater than or equal to 90% at approximately 800-1500 nm.

In some implementations, surface A or surface B has a dielectric coating that is anti-reflecting at an operating wavelength of one or more light sources 110 contained within enclosure 155. An AR coating on surface A and surface B may increase the amount of light at an operating wavelength of light source 110 that is transmitted through the window 157. Additionally, an AR coating at an operating wavelength of the light source 110 may reduce the amount of incident light from output beam 125 that is reflected by the window 157 back into the housing 155. In an example implementation, each of surface A and surface B has an AR coating with reflectivity less than 0.5% at an operating wavelength of light source 110. As an example, if the light source 110 has an operating wavelength of approximately 1550 nm, then surface A and surface B may each have an AR coating with a reflectivity that is less than 0.5% from approximately 1547 nm to approximately 1553 nm. In another implementation, each of surface A and surface B has an AR coating with reflectivity less than 1% at the operating wavelengths of the light source 110. For example, if the housing 155 encloses two sensor heads with respective light sources, the first light source emits pulses at a wavelength of approximately 1535 nm and the second light source emits pulses at a wavelength of approximately 1540 nm, then surface A and surface B may each have an AR coating with reflectivity less than 1% from approximately 1530 nm to approximately 1545 nm.

The window 157 may have an optical transmission that is greater than any suitable value for one or more wavelengths of one or more light sources 110 contained within the housing 155. As an example, the window 157 may have an optical transmission of greater than or equal to 70%, 80%, 90%, 95%, or 99% at a wavelength of light source 110. In one example implementation, the window 157 can transmit greater than or equal to 95% of light at an operating wavelength of the light source 110. In another implementation, the window 157 transmits greater than or equal to 90% of light at the operating wavelengths of the light sources enclosed within the housing 155.

Surface A or surface B may have a dichroic coating that is anti-reflecting at one or more operating wavelengths of one or more light sources 110 and high-reflecting at wavelengths away from the one or more operating wavelengths. For example, surface A may have an AR coating for an operating wavelength of the light source 110, and surface B may have a dichroic coating that is AR at the light-source operating wavelength and HR for wavelengths away from the operating wavelength. A coating that is HR for wavelengths away from a light-source operating wavelength may prevent most incoming light at unwanted wavelengths from being transmitted through the window 117. In one implementation, if light source 110 emits optical pulses with a wavelength of approximately 1550 nm, then surface A may have an AR coating with a reflectivity of less than or equal to 0.5% from approximately 1546 nm to approximately 1554 nm. Additionally, surface B may have a dichroic coating that is AR at approximately 1546-1554 nm and HR (e.g., reflectivity of greater than or equal to 90%) at approximately 800-1500 nm and approximately 1580-1700 nm.

Surface B of the window 157 may include a coating that is oleophobic, hydrophobic, or hydrophilic. A coating that is oleophobic (or, lipophobic) may repel oils (e.g., fingerprint oil or other non-polar material) from the exterior surface (surface B) of the window 157. A coating that is hydrophobic may repel water from the exterior surface. For example, surface B may be coated with a material that is both oleophobic and hydrophobic. A coating that is hydrophilic attracts water so that water may tend to wet and form a film on the hydrophilic surface (rather than forming beads of water as may occur on a hydrophobic surface). If surface B has a hydrophilic coating, then water (e.g., from rain) that lands on surface B may form a film on the surface. The surface film of water may result in less distortion, deflection, or occlusion of an output beam 125 than a surface with a non-hydrophilic coating or a hydrophobic coating.

With continued reference to FIG. 1, the light source 110 may include a pulsed laser configured to produce or emit pulses of light with a certain pulse duration. In an example implementation, the pulse duration or pulse width of the pulsed laser is approximately 10 picoseconds (ps) to 20 nanoseconds (ns). In another implementation, the light source 110 is a pulsed laser that produces pulses with a pulse duration of approximately 1-4 ns. In yet another implementation, the light source 110 is a pulsed laser that produces pulses at a pulse repetition frequency of approximately 100 kHz to 5 MHz or a pulse period (e.g., a time between successive pulses) of approximately 200 ns to 10 µs. The light source 110 may have a substantially constant or a variable pulse repetition frequency, depending on the implementation. As an example, the light source 110 may be a pulsed laser that produces pulses at a substantially constant pulse repetition frequency of approximately 640 kHz (e.g., 640,000 pulses per second), corresponding to a pulse period of approximately 1.56 µs. As another example, the light source 110 may have a pulse repetition frequency that can be varied from approximately 500 kHz to 3 MHz. As used herein, a pulse of light may be referred to as an optical pulse, a light pulse, or a pulse, and a pulse repetition frequency may be referred to as a pulse rate.

In general, the output beam 125 may have any suitable average optical power, and the output beam 125 may include optical pulses with any suitable pulse energy or peak optical power. Some examples of the average power of the output beam 125 include the approximate values of 1 mW, 10 mW, 100 mW, 1 W, and 10 W. Example values of pulse energy of the output beam 125 include the approximate values of 0.1 µJ, 1 µJ, 10 µJ, 100 µJ, and 1 mJ. Examples of peak power values of pulses included in the output beam 125 are the approximate values of 10 W, 100 W, 1 kW, 5 kW, 10 kW. An example optical pulse with a duration of 1 ns and a pulse energy of 1 µJ has a peak power of approximately 1 kW. If the pulse repetition frequency is 500 kHz, then the average power of the output beam 125 with 1-µJ pulses is approximately 0.5 W, in this example.

The light source 110 may include a laser diode, such as a Fabry-Perot laser diode, a quantum well laser, a distributed Bragg reflector (DBR) laser, a distributed feedback (DFB) laser, or a vertical-cavity surface-emitting laser (VCSEL). The laser diode operating in the light source 110 may be an aluminum-gallium-arsenide (AlGaAs) laser diode, an indium-gallium-arsenide (InGaAs) laser diode, or an indium-gallium-arsenide-phosphide (InGaAsP) laser diode, or any other suitable diode. In some implementations, the light source 110 includes a pulsed laser diode with a peak emission wavelength of approximately 1400-1600 nm. Further, the light source 110 may include a laser diode that is current-modulated to produce optical pulses.

In some implementations, the light source 110 includes a pulsed laser diode followed by one or more optical-amplification stages. For example, the light source 110 may be a fiber-laser module that includes a current-modulated laser diode with a peak wavelength of approximately 1550 nm, followed by a single-stage or a multi-stage erbium-doped fiber amplifier (EDFA). As another example, the light source 110 may include a continuous-wave (CW) or quasi-CW laser diode followed by an external optical modulator (e.g., an electro-optic modulator), and the output of the modulator may be fed into an optical amplifier. A light source 110 that includes a laser diode followed by one or more optical-amplification stages may be referred to as a master oscillator power amplifier (MOPA) in which the laser diode acts as a master oscillator. In yet other implementations, the light source 110 may include a pulsed solid-state laser or a pulsed fiber laser.

In some implementations, the output beam of light 125 emitted by the light source 110 is a collimated optical beam with any suitable beam divergence, such as a divergence of approximately 0.1 to 3.0 milliradian (mrad). Divergence of the output beam 125 may refer to an angular measure of an increase in beam size (e.g., a beam radius or beam diameter) as the output beam 125 travels away from the light source 110 or the lidar system 100. The output beam 125 may have a substantially circular cross section with a beam divergence characterized by a single divergence value. For example, the output beam 125 with a circular cross section and a divergence of 1 mrad may have a beam diameter or spot size of approximately 10 cm at a distance of 100 m from the lidar system 100. In some implementations, the output beam 125 may be an astigmatic beam or may have a substantially elliptical cross section and may be characterized by two divergence values. As an example, the output beam 125 may have a fast axis and a slow axis, where the fast-axis divergence is greater than the slow-axis divergence. As another example, the output beam 125 may be an astigmatic beam with a fast-axis divergence of 2 mrad and a slow-axis divergence of 0.5 mrad.

The output beam of light 125 emitted by light source 110 may be unpolarized or randomly polarized, may have no specific or fixed polarization (e.g., the polarization may vary with time), or may have a particular polarization (e.g., the output beam 125 may be linearly polarized, elliptically polarized, or circularly polarized). As an example, the light source 110 may produce linearly polarized light, and the lidar system 100 may include a quarter-wave plate that converts this linearly polarized light into circularly polarized light. The lidar system 100 may transmit the circularly polarized light as the output beam 125, and receive the input beam 135, which may be substantially or at least partially circularly polarized in the same manner as the output beam 125 (e.g., if the output beam 125 is right-hand circularly polarized, then the input beam 135 may also be right-hand circularly polarized). The input beam 135 may pass through the same quarter-wave plate (or a different quarter-wave plate), resulting in the input beam 135 being converted to linearly polarized light which is orthogonally polarized (e.g., polarized at a right angle) with respect to the linearly polarized light produced by light source 110. As another example, the lidar system 100 may employ polarization-diversity detection where two polarization components are detected separately. The output beam 125 may be linearly polarized, and the lidar system 100 may split the input beam 135 into two polarization components (e.g., s-polarization and p-polarization) which are detected separately by two photodiodes (e.g., a balanced photoreceiver that includes two photodiodes).

With continued reference to FIG. 1, the output beam 125 and input beam 135 may be substantially coaxial. In other words, the output beam 125 and input beam 135 may at least partially overlap or share a common propagation axis, so that the input beam 135 and the output beam 125 travel along substantially the same optical path (albeit in opposite directions). As the lidar system 100 scans the output beam 125 across a field of regard, the input beam 135 may follow along with the output beam 125, so that the coaxial relationship between the two beams is maintained.

The lidar system 100 also may include one or more optical components configured to condition, shape, filter, modify, steer, or direct the output beam 125 and/or the input beam 135. For example, lidar system 100 may include one or more lenses, mirrors, filters (e.g., bandpass or interference filters), beam splitters, polarizers, polarizing beam splitters, wave plates (e.g., half-wave or quarter-wave plates), diffractive elements, or holographic elements. In some implementations, lidar system 100 includes a telescope, one or more lenses, or one or more mirrors to expand, focus, or collimate the output beam 125 to a desired beam diameter or divergence. As an example, the lidar system 100 may include one or more lenses to focus the input beam 135 onto an active region of the receiver 140. As another example, the lidar system 100 may include one or more flat mirrors or curved mirrors (e.g., concave, convex, or parabolic mirrors) to steer or focus the output beam 125 or the input beam 135. For example, the lidar system 100 may include an off-axis parabolic mirror to focus the input beam 135 onto an active region of receiver 140. As illustrated in FIG. 1, the lidar system 100 may include the mirror 115, which may be a metallic or dielectric mirror. The mirror 115 may be configured so that the light beam 125 passes through the mirror 115. As an example, mirror 115 may include a hole, slot, or aperture through which the output light beam 125 passes. As another example, the mirror 115 may be configured so that at least 80% of the output beam 125 passes through the mirror 115 and at least 80% of the input beam 135 is reflected by the mirror 115. In some implementations, the mirror 115 may provide for the output beam 125 and the input beam 135 to be substantially coaxial, so that the beams 125 and 135 travel along substantially the same optical path, in opposite directions.

Generally speaking, the scanner 120 steers the output beam 125 in one or more directions downrange. The scanner 120 may include one or more scanning mirrors and one or more actuators driving the mirrors to rotate, tilt, pivot, or move the mirrors in an angular manner about one or more axes, for example. For example, the first mirror of the scanner may scan the output beam 125 along a first direction, and the second mirror may scan the output beam 125 along a second direction that is substantially orthogonal to the first direction. Example implementations of the scanner 120 are discussed in more detail below with reference to FIG. 2.

The scanner 120 may be configured to scan the output beam 125 over a 5-degree angular range, 20-degree angular range, 30-degree angular range, 60-degree angular range, or any other suitable angular range. For example, a scanning mirror may be configured to periodically rotate over a 15-degree range, which results in the output beam 125 scanning across a 30-degree range (e.g., a Θ-degree rotation by a scanning mirror results in a 2Θ-degree angular scan of the output beam 125). A field of regard (FOR) of the lidar system 100 may refer to an area, region, or angular range over which the lidar system 100 may be configured to scan or capture distance information. When the lidar system 100 scans the output beam 125 within a 30-degree scanning range, the lidar system 100 may be referred to as having a 30-degree angular field of regard. As another example, a lidar system 100 with a scanning mirror that rotates over a 30-degree range may produce the output beam 125 that scans across a 60-degree range (e.g., a 60-degree FOR). In various implementations, the lidar system 100 may have a FOR of approximately 10°, 20°, 40°, 60°, 120°, or any other suitable FOR. The FOR also may be referred to as a scan region.

The scanner 120 may be configured to scan the output beam 125 horizontally and vertically, and the lidar system 100 may have a particular FOR along the horizontal direction and another particular FOR along the vertical direction. For example, the lidar system 100 may have a horizontal FOR of 10° to 120° and a vertical FOR of 2° to 45°.

The one or more scanning mirrors of the scanner 120 may be communicatively coupled to the controller 150 which may control the scanning mirror(s) so as to guide the output beam 125 in a desired direction downrange or along a desired scan pattern. In general, a scan pattern may refer to a pattern or path along which the output beam 125 is directed, and also may be referred to as an optical scan pattern, optical scan path, or scan path. As an example, the scanner 120 may include two scanning mirrors configured to scan the output beam 125 across a 60° horizontal FOR and a 20° vertical FOR. The two scanner mirrors may be controlled to follow a scan path that substantially covers the 60°×20° FOR. The lidar system 100 can use the scan path to generate a point cloud with pixels that substantially cover the 60°×20° FOR. The pixels may be approximately evenly distributed across the 60°×20° FOR. Alternately, the pixels may have a particular non-uniform distribution (e.g., the pixels may be distributed across all or a portion of the 60°×20° FOR, and the pixels may have a higher density in one or more particular regions of the 60°×20° FOR).

In operation, the light source 110 may emit pulses of light which the scanner 120 scans across a FOR of lidar system 100. The target 130 may scatter one or more of the emitted pulses, and the receiver 140 may detect at least a portion of the pulses of light scattered by the target 130.

The receiver 140 may be referred to as (or may include) a photoreceiver, optical receiver, optical sensor, detector, photodetector, or optical detector. The receiver 140 in some implementations receives or detects at least a portion of the input beam 135 and produces an electrical signal that corresponds to the input beam 135. For example, if the input beam 135 includes an optical pulse, then the receiver 140 may produce an electrical current or voltage pulse that corresponds to the optical pulse detected by the receiver 140. In an example implementation, the receiver 140 includes one or more avalanche photodiodes (APDs) or one or more single-photon avalanche diodes (SPADs). In another implementation, the receiver 140 includes one or more PN photodiodes (e.g., a photodiode structure formed by a p-type semiconductor and a n-type semiconductor) or one or more PIN photodiodes (e.g., a photodiode structure formed by an undoped intrinsic semiconductor region located between p-type and n-type regions).

The receiver 140 may have an active region or an avalanche-multiplication region that includes silicon, germanium, or InGaAs. The active region of receiver 140 may have any suitable size, such as for example, a diameter or width of approximately 50-500 μm. The receiver 140 may include circuitry that performs signal amplification, sampling, filtering, signal conditioning, analog-to-digital conversion, time-to-digital conversion, pulse detection, threshold detection, rising-edge detection, or falling-edge detection. For example, the receiver 140 may include a transimpedance amplifier that converts a received photocurrent (e.g., a current produced by an APD in response to a received optical signal) into a voltage signal. The receiver 140 may direct the voltage signal to pulse-detection circuitry that produces an analog or digital output signal 145 that corresponds to one or more characteristics (e.g., rising edge, falling edge, amplitude, or duration) of a received optical pulse. For example, the pulse-detection circuitry may perform a time-to-digital conversion to produce a digital output signal 145. The receiver 140 may send the electrical output signal 145 to the controller 150 for processing or analysis, e.g., to determine a time-of-flight value corresponding to a received optical pulse.

The controller 150 may be electrically coupled or otherwise communicatively coupled to one or more of the light source 110, the scanner 120, and the receiver 140. The controller 150 may receive electrical trigger pulses or edges from the light source 110, where each pulse or edge corresponds to the emission of an optical pulse by the light source 110. The controller 150 may provide instructions, a control signal, or a trigger signal to the light source 110 indicating when the light source 110 should produce optical pulses. For example, the controller 150 may send an electrical trigger signal that includes electrical pulses, where the light source 110 emits an optical pulse in response to each electrical pulse. Further, the controller 150 may cause the light source 110 to adjust one or more of the frequency, period, duration, pulse energy, peak power, average power, or wavelength of the optical pulses produced by light source 110.

The controller 150 may determine a time-of-flight value for an optical pulse based on timing information associated with when the pulse was emitted by light source 110 and when a portion of the pulse (e.g., the input beam 135) was detected or received by the receiver 140. The controller 150 may include circuitry that performs signal amplification, sampling, filtering, signal conditioning, analog-to-digital conversion, time-to-digital conversion, pulse detection, threshold detection, rising-edge detection, or falling-edge detection.

As indicated above, the lidar system 100 may be used to determine the distance to one or more downrange targets 130. By scanning the lidar system 100 across a field of regard, the system can be used to map the distance to a number of points within the field of regard. Each of these depth-mapped points may be referred to as a pixel or a voxel. A collection of pixels captured in succession (which may be referred to as a depth map, a point cloud, or a frame) may be rendered as an image or may be analyzed to identify or detect objects or to determine a shape or distance of objects within the FOR. For example, a depth map may cover a field of regard that extends 60° horizontally and 15° vertically, and the depth map may include a frame of 100-2000 pixels in the horizontal direction by 4-400 pixels in the vertical direction.

The lidar system 100 may be configured to repeatedly capture or generate point clouds of a field of regard at any suitable frame rate between approximately 0.1 frames per second (FPS) and approximately 1,000 FPS. For example, the lidar system 100 may generate point clouds at a frame rate of approximately 0.1 FPS, 0.5 FPS, 1 FPS, 2 FPS, 5 FPS, 10 FPS, 20 FPS, 100 FPS, 500 FPS, or 1,000 FPS. In an example implementation, the lidar system 100 is configured to produce optical pulses at a rate of $5\times10^5$ pulses/second (e.g., the system may determine 500,000 pixel distances per second) and scan a frame of 1000×50 pixels (e.g., 50,000 pixels/frame), which corresponds to a point-cloud frame rate of 10 frames per second (e.g., 10 point clouds per second). The point-cloud frame rate may be substantially fixed or dynamically adjustable, depending on the implementation. For example, the lidar system 100 may capture one or more point clouds at a particular frame rate (e.g., 1 Hz) and then switch to capture one or more point clouds at a different frame rate (e.g., 10 Hz). In general, the lidar system can use a slower frame rate (e.g., 1 Hz) to capture one or more high-resolution point clouds, and use a faster frame rate (e.g., 10 Hz) to rapidly capture multiple lower-resolution point clouds.

The field of regard of the lidar system 100 can overlap, encompass, or enclose at least a portion of the target 130, which may include all or part of an object that is moving or stationary relative to lidar system 100. For example, the target 130 may include all or a portion of a person, vehicle, motorcycle, truck, train, bicycle, wheelchair, pedestrian, animal, road sign, traffic light, lane marking, road-surface marking, parking space, pylon, guard rail, traffic barrier, pothole, railroad crossing, obstacle in or near a road, curb, stopped vehicle on or beside a road, utility pole, house, building, trash can, mailbox, tree, any other suitable object, or any suitable combination of all or part of two or more objects.

The controller 150 can include a distance/velocity mode selector 160 that determines whether the lidar system operates in the distance-determination mode or the velocity-determination mode. Depending on the implementation, the mode selector 160 can be implemented as a software module, a hardware module, or a combination thereof. The mode selector 160 can provide electrical signals to the light source 110 to control when the light source generates pulses and, in some cases, other parameters of the pulses such as amplitude, wavelength, etc.

Figure 2:
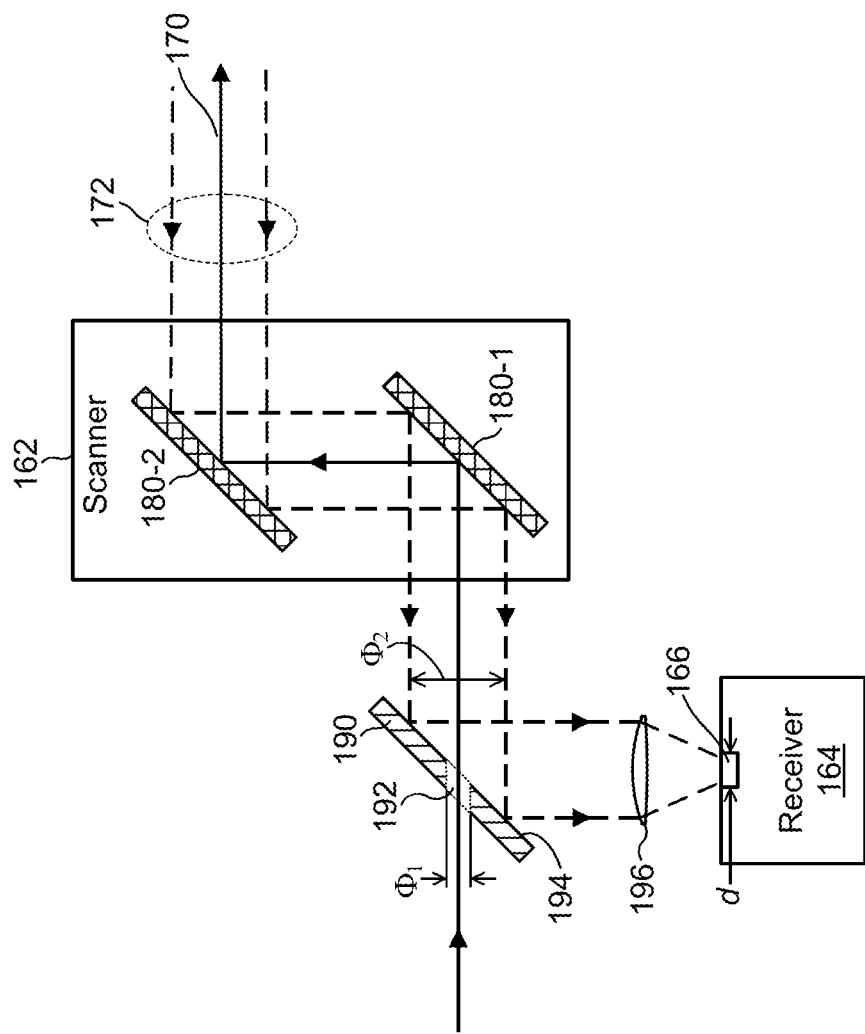
FIG. 2 illustrates in more detail several components that can operate in the system of FIG. 1 to scan a field of regard of the lidar system.

Now referring to FIG. 2, a scanner 162 and a receiver 164 can operate in the lidar system of FIG. 1 as the scanner 120 and the receiver 140, respectively. More generally, the scanner 162 and the receiver 164 can operate in any suitable lidar system.

The scanner 162 may include any suitable number of mirrors driven by any suitable number of mechanical actuators. For example, the scanner 162 may include a galvanometer scanner, a resonant scanner, a piezoelectric actuator, a polygonal scanner, a rotating-prism scanner, a voice coil motor, a DC motor, a brushless DC motor, a stepper motor, or a microelectromechanical systems (MEMS) device, or any other suitable actuator or mechanism.

A galvanometer scanner (which also may be referred to as a galvanometer actuator) may include a galvanometer-based scanning motor with a magnet and coil. When an electrical current is supplied to the coil, a rotational force is applied to the magnet, which causes a mirror attached to the galvanometer scanner to rotate. The electrical current supplied to the coil may be controlled to dynamically change the position of the galvanometer mirror. A resonant scanner (which may be referred to as a resonant actuator) may include a spring-like mechanism driven by an actuator to produce a periodic oscillation at a substantially fixed frequency (e.g., 1 kHz). A MEMS-based scanning device may include a mirror with a diameter between approximately 1 and 10 mm, where the mirror is rotated using electromagnetic or electrostatic actuation. A voice coil motor (which may be referred to as a voice coil actuator) may include a magnet and coil. When an electrical current is supplied to the coil, a translational force is applied to the magnet, which causes a mirror attached to the magnet to move or rotate.

In an example implementation, the scanner 162 includes a single mirror configured to scan an output beam 170 along a single direction (e.g., the scanner 162 may be a one-dimensional scanner that scans along a horizontal or vertical direction). The mirror may be a flat scanning mirror attached to a scanner actuator or mechanism which scans the mirror over a particular angular range. The mirror may be driven by one actuator (e.g., a galvanometer) or two actuators configured to drive the mirror in a push-pull configuration. When two actuators drive the mirror in one direction in a push-pull configuration, the actuators may be located at opposite ends or sides of the mirror. The actuators may operate in a cooperative manner so that when one actuator pushes on the mirror, the other actuator pulls on the mirror, and vice versa. In another example implementation, two voice coil actuators arranged in a push-pull configuration drive a mirror along a horizontal or vertical direction.

In some implementations, the scanner 162 may include one mirror configured to be scanned along two axes, where two actuators arranged in a push-pull configuration provide motion along each axis. For example, two resonant actuators arranged in a horizontal push-pull configuration may drive the mirror along a horizontal direction, and another pair of resonant actuators arranged in a vertical push-pull configuration may drive mirror along a vertical direction. In another example implementation, two actuators scan the output beam 170 along two directions (e.g., horizontal and vertical), where each actuator provides rotational motion along a particular direction or about a particular axis.

The scanner 162 also may include one mirror driven by two actuators configured to scan the mirror along two substantially orthogonal directions. For example, a resonant actuator or a galvanometer actuator may drive one mirror along a substantially horizontal direction, and a galvanometer actuator may drive the mirror along a substantially vertical direction. As another example, two resonant actuators may drive a mirror along two substantially orthogonal directions.

In some implementations, the scanner 162 includes two mirrors, where one mirror scans the output beam 170 along a substantially horizontal direction and the other mirror scans the output beam 170 along a substantially vertical direction. In the example of FIG. 2, the scanner 162 includes two mirrors, a mirror 180-1 and a mirror 180-2. The mirror 180-1 may scan the output beam 170 along a substantially horizontal direction, and the mirror 180-2 may scan the output beam 170 along a substantially vertical direction (or vice versa). Mirror 180-1 or mirror 180-2 may be a flat mirror, a curved mirror, or a polygon mirror with two or more reflective surfaces.

The scanner 162 in other implementations includes two galvanometer scanners driving respective mirrors. For example, the scanner 162 may include a galvanometer actuator that scans the mirror 180-1 along a first direction (e.g., vertical), and the scanner 162 may include another galvanometer actuator that scans the mirror 180-2 along a second direction (e.g., horizontal). In yet another implementation, the scanner 162 includes two mirrors, where a galvanometer actuator drives one mirror, and a resonant actuator drives the other mirror. For example, a galvanometer actuator may scan the mirror 180-1 along a first direction, and a resonant actuator may scan the mirror 180-2 along a second direction. The first and second scanning directions may be substantially orthogonal to one another, e.g., the first direction may be substantially vertical, and the second direction may be substantially horizontal. In yet another implementation, the scanner 162 includes two mirrors, where one mirror is a polygon mirror that is rotated in one direction (e.g., clockwise or counter-clockwise) by an electric motor (e.g., a brushless DC motor). For example, mirror 180-1 may be a polygon mirror that scans the output beam 170 along a substantially horizontal direction, and mirror 180-2 may scan the output beam 170 along a substantially vertical direction. A polygon mirror may have two or more reflective surfaces, and the polygon mirror may be continuously rotated in one direction so that the output beam 170 is reflected sequentially from each of the reflective surfaces. A polygon mirror may have a cross-sectional shape that corresponds to a polygon, where each side of the polygon has a reflective surface. For example, a polygon mirror with a square cross-sectional shape may have four reflective surfaces, and a polygon mirror with a pentagonal cross-sectional shape may have five reflective surfaces.

To direct the output beam 170 along a particular scan pattern, the scanner 162 may include two or more actuators driving a single mirror synchronously. For example, the two or more actuators can drive the mirror synchronously along two substantially orthogonal directions to make the output beam 170 follow a scan pattern with substantially straight lines. In some implementations, the scanner 162 may include two mirrors and actuators driving the two mirrors synchronously to generate a scan pattern that includes substantially straight lines. For example, a galvanometer actuator may drive the mirror 180-2 with a substantially linear back-and-forth motion (e.g., the galvanometer may be driven with a substantially sinusoidal or triangle-shaped waveform) that causes the output beam 170 to trace a substantially horizontal back-and-forth pattern, and another galvanometer actuator may scan the mirror 180-1 along a substantially vertical direction. The two galvanometers may be synchronized so that for every 64 horizontal traces, the output beam 170 makes a single trace along a vertical direction. Whether one or two mirrors are used, the substantially straight lines can be directed substantially horizontally, vertically, or along any other suitable direction.

The scanner 162 also may apply a dynamically adjusted deflection along a vertical direction (e.g., with a galvanometer actuator) as the output beam 170 is scanned along a substantially horizontal direction (e.g., with a galvanometer or resonant actuator) to achieve the straight lines. If a vertical deflection is not applied, the output beam 170 may trace out a curved path as it scans from side to side. In some implementations, the scanner 162 uses a vertical actuator to apply a dynamically adjusted vertical deflection as the output beam 170 is scanned horizontally as well as a discrete vertical offset between each horizontal scan (e.g., to step the output beam 170 to a subsequent row of a scan pattern).

With continued reference to FIG. 2, an overlap mirror 190 in this example implementation is configured to overlap the input beam 172 and output beam 170, so that the beams 170 and 172 are substantially coaxial. In FIG. 2, the overlap mirror 190 includes a hole, slot, or aperture 192 through which the output beam 170 passes, and a reflecting surface 194 that reflects at least a portion of the input beam 172 toward the receiver 164. The overlap mirror 190 may be oriented so that input beam 172 and output beam 170 are at least partially overlapped.

In some implementations, the overlap mirror 190 may not include a hole 192. For example, the output beam 170 may be directed to pass by a side of mirror 190 rather than passing through an aperture 192. The output beam 170 may pass alongside mirror 190 and may be oriented at a slight angle with respect to the orientation of the input beam 172. As another example, the overlap mirror 190 may include a small reflective section configured to reflect the output beam 170, and the rest of the overlap mirror 190 may have an AR coating configured to transmit the input beam 172.

The input beam 172 may pass through a lens 196 which focuses the beam onto an active region 166 of the receiver 164. The active region 166 may refer to an area over which receiver 164 may receive or detect input light. The active region may have any suitable size or diameter d, such as for example, a diameter of approximately 25 µm, 50 µm, 80 µm, 100 µm, 200 µm, 500 µm, 1 mm, 2 mm, or 5 mm. The overlap mirror 190 may have a reflecting surface 194 that is substantially flat or the reflecting surface 194 may be curved (e.g., the mirror 190 may be an off-axis parabolic mirror configured to focus the input beam 172 onto an active region of the receiver 140).

The aperture 192 may have any suitable size or diameter $\Phi_1$, and the input beam 172 may have any suitable size or diameter $\Phi_2$, where $\Phi_2$ is greater than $\Phi_1$. For example, the aperture 192 may have a diameter $\Phi_1$ of approximately 0.2 mm, 0.5 mm, 1 mm, 2 mm, 3 mm, 5 mm, or 10 mm, and the input beam 172 may have a diameter $\Phi_2$ of approximately 2 mm, 5 mm, 10 mm, 15 mm, 20 mm, 30 mm, 40 mm, or 50 mm. In some implementations, the reflective surface 194 of the overlap mirror 190 may reflect 70% or more of input beam 172 toward the receiver 164. For example, if the reflective surface 194 has a reflectivity R at an operating wavelength of the light source, then the fraction of input beam 172 directed toward the receiver 164 may be expressed as $R \times [1-(\Phi_1/\Phi_2)^2]$. As a more specific example, if R is 95%, $\Phi_1$ is 2 mm, and $\Phi_2$ is 10 mm, then approximately 91% of the input beam 172 may be directed toward the receiver 164 by the reflective surface 194.

Figure 3:
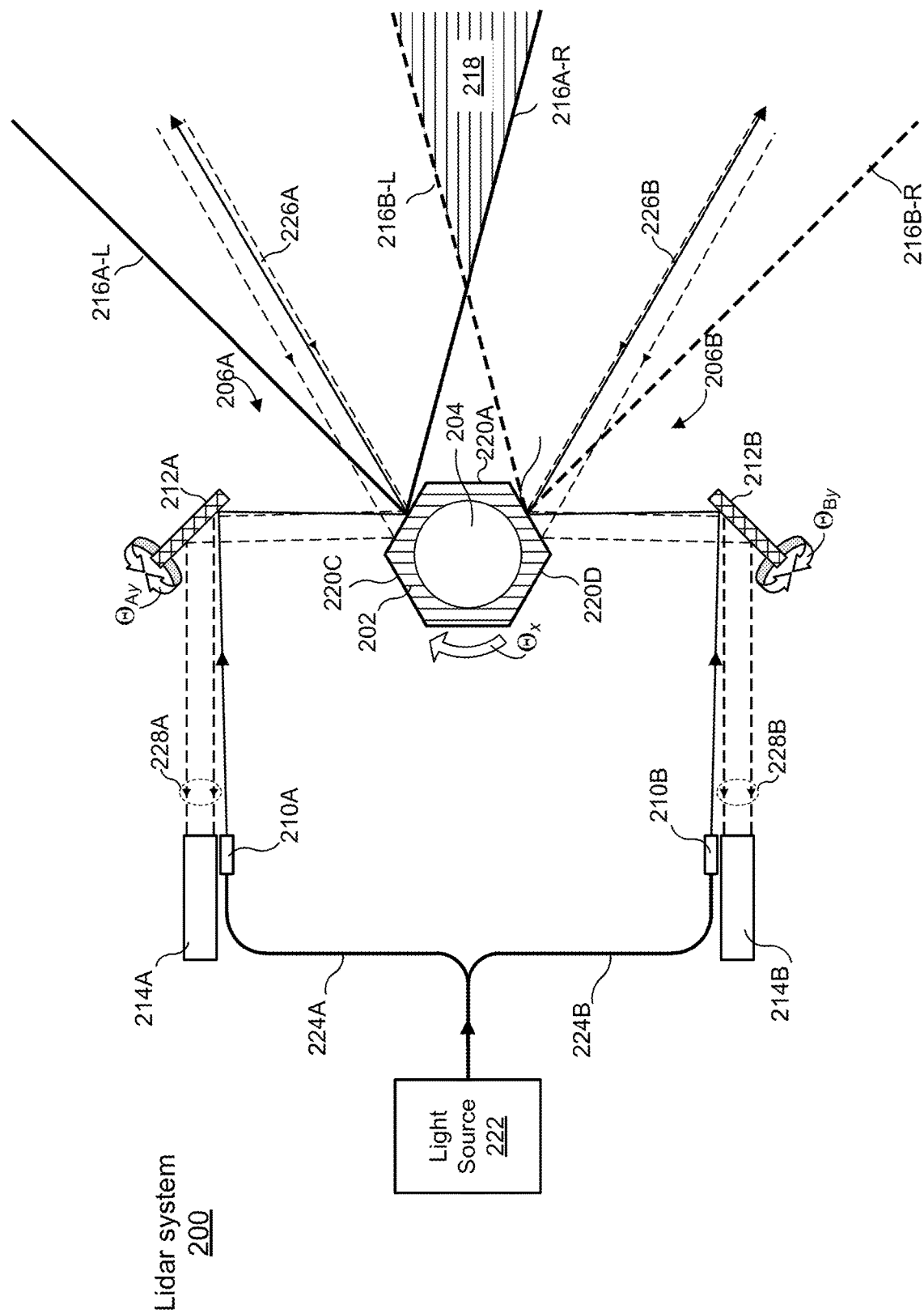
FIG. 3 is a block diagram of a lidar system in which the scanner includes a polygon mirror and can operate in a two-eye configuration with overlapping fields of regard.

FIG. 3 illustrates another example lidar system 200 that can operate in a dual mode to determine the distance to a target as well as the velocity of the target. The lidar system 200 includes a polygon mirror 202 driven by a motor 204. The lidar system 200 operates in a two-eye configuration, with a first eye 206A and a second eye 206B. The first eye 206A includes a collimator 210A, a scan mirror 212A, and a receiver 214A, and the second eye 206B includes a collimator 210B, a scan mirror 212B, and a receiver 214B. The polygon mirror 202 may be in the form of a rotatable block with multiple reflective surfaces angularly offset from one another along the polygon periphery of the rotatable block. In this example implementation, the polygon mirror 202 has six reflective surfaces 220A, 220B, . . . 220F; however, the polygon mirror 202 in general can include any suitable number of surfaces, e.g., three, four, five, eight, etc. The motor 204 imparts rotation to the rotatable polygon mirror 202. The scan mirrors 212A and 212B are configured to rotate, in an oscillatory manner within a certain angular range, about the respective axis orthogonal to the axis of rotation of the polygon mirror 202.

A light source 222 can be a fiber laser that includes a seed laser diode. The output of the light source 222 can be provided to the collimators 210A and 210B via fiber-optic cables 224A and 224B, free-space coupling, or in any other suitable manner. While the lidar system 200 uses collimators coupled to a shared light source, in other implementations of this system each eye can include its own direct-emitted laser diode. The light source 222 in this case can be made of multiple direct-emitter laser diodes (e.g., high-power laser diodes) that directly emit the pulses without requiring optical amplification. The laser diodes can be housed in the respective sensor heads.

In operation, the collimators 210A and 210B direct output beams 226A and 226B to the scan mirrors 212A and 212B, respectively. The scan mirrors 212A and 212B then reflect these beams toward non-adjacent reflective surfaces of the polygon mirror 202, which then directs the output beams 226A and 226B to respective fields of regard. Input beams 228A and 228B are incident on non-adjacent reflective surfaces of the polygon mirror 202 and are reflected toward the scan mirrors 212A and 212B, respectively. The input beams 228A and 228B then propagate toward the receivers 214A and 214B. In other implementations, input and output beams from different eyes can be incident on adjacent surfaces of the polygon mirror.

Referring back to FIG. 1, the scanner 120 in some implementations includes a polygon mirror similar to the polygon mirror 202 and one or two mirrors similar to the scan mirrors 212A and 212B, depending on the number of eyes of the lidar system.

In the configuration of FIG. 3, the field of regard (FOR) of the lidar system includes the FOR is the combination of the FOR of the first eye 206A, which extends from the left boundary 216A-L to the right boundary 216A-R, and the FOR of the second eye 206B, which extends from the left boundary 216B-L to the right boundary 216B-R. The FORs of the two eyes define an overlap region 218. In some implementations, the lidar system 200 generates a higher density of information when scanning the overlap region 218. In another implementation, the lidar system 200 operates the first eye in distance-determination mode and the second eye in the velocity-determination mode, only when scanning the overlap region 218. To this end, the light source 222 can include separately operable lasers or a shared laser with separately operable optical modulators responsible for transmitting different respective optical signals via the links 224A and 224B. A controller similar to the distance/velocity mode selector 160 can provide different electrical signals to these separately operable lasers or optical modulators.

Figure 4:
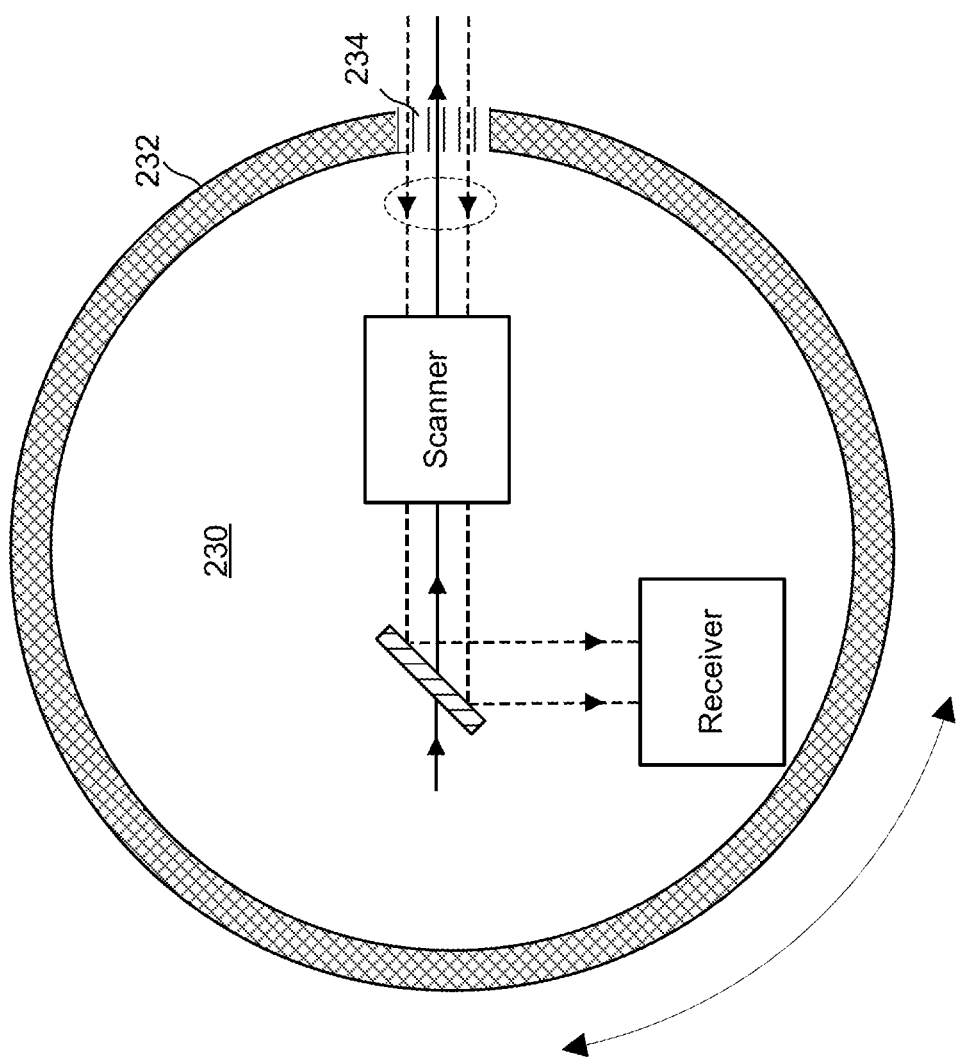
FIG. 4 illustrates an example configuration in which the components of FIG. 1 scan a 360-degree field of regard through a window in a rotating housing.

FIG. 4 illustrates an example configuration in which several components of the lidar system 100 or another suitable system may operate to scan a 360-degree view of regard. Generally speaking, the field of view of a light source in this configuration follows a circular trajectory and accordingly defines a circular scan pattern on a two-dimensional plane. All points on the trajectory remain at the same elevation relative to the ground level, according to one implementation. In this case, separate beams may follow the circular trajectory with certain vertical offsets relative to each other. In another implementation, the points of the trajectory may define a spiral scan pattern in three-dimensional space. A single beam can be sufficient to trace out the spiral scan pattern but, if desired, multiple beams can be used.

In the example of FIG. 4, a rotating scan module 230 revolves around a central axis in one or both directions as indicated. An electric motor may drive the rotating scan module 230 around the central axis at a constant speed, for example. The rotating scan module 230 includes a scanner, a receiver, an overlap mirror, etc. The components of the rotating module 230 may be similar to the scanner 120, the receiver 140, and the overlap mirror 115 discussed above. In some implementations, the rotating scan module 230 also includes a light source and a controller. In other implementations, the light source and/or the controller are disposed apart from the rotating scan module 230 and/or exchange optical and electrical signals with the components of the rotating scan module 230 via corresponding links.

The rotating scan module 230 may include a housing 232 with a window 234. Similar to the window 157 of FIG. 1, the window 234 may be made of glass, plastic, or any other suitable material. The window 234 allows outbound beams as well as return signals to pass through the housing 232. The arc length defined by the window 234 can correspond to any suitable percentage of the circumference of the housing 232. For example, the arc length can correspond to 5%, 20%, 30%, 60%, or possibly even 100% of the circumference.

Figure 5:
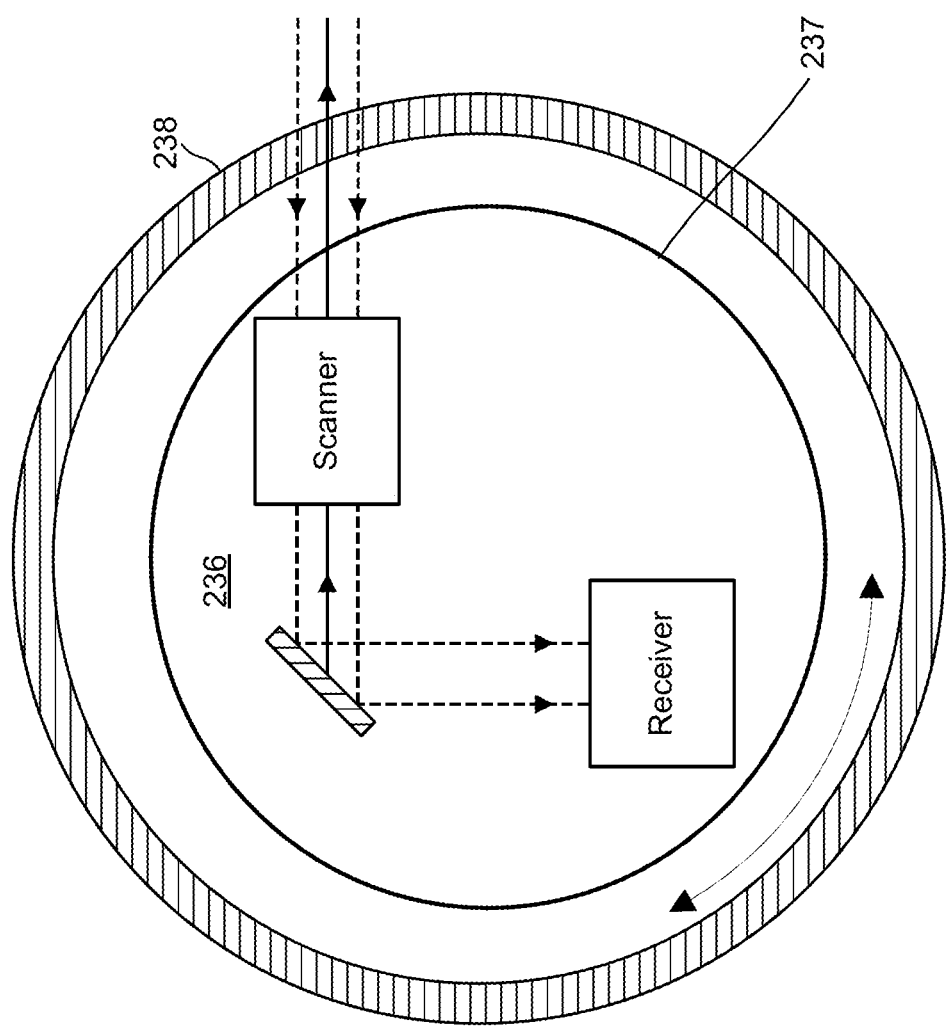
FIG. 5 illustrates another configuration in which the components of FIG. 1 scan a 360-degree field of regard through a substantially transparent stationary housing.

Now referring to FIG. 5, a rotating scan module 236 is generally similar to the rotating scan module 230. In this implementation, however, the components of the rotating scan module 236 are disposed on a platform 237 which rotates inside a stationary circular housing 238. In this implementation, the circular housing 238 is substantially transparent to light at the lidar-system operating wavelength to pass inbound and outbound light signals. The circular housing 238 in a sense defines a circular window similar to the window 234 and may be made of similar material.

Generating Pixels within a Field of Regard

Figure 6:
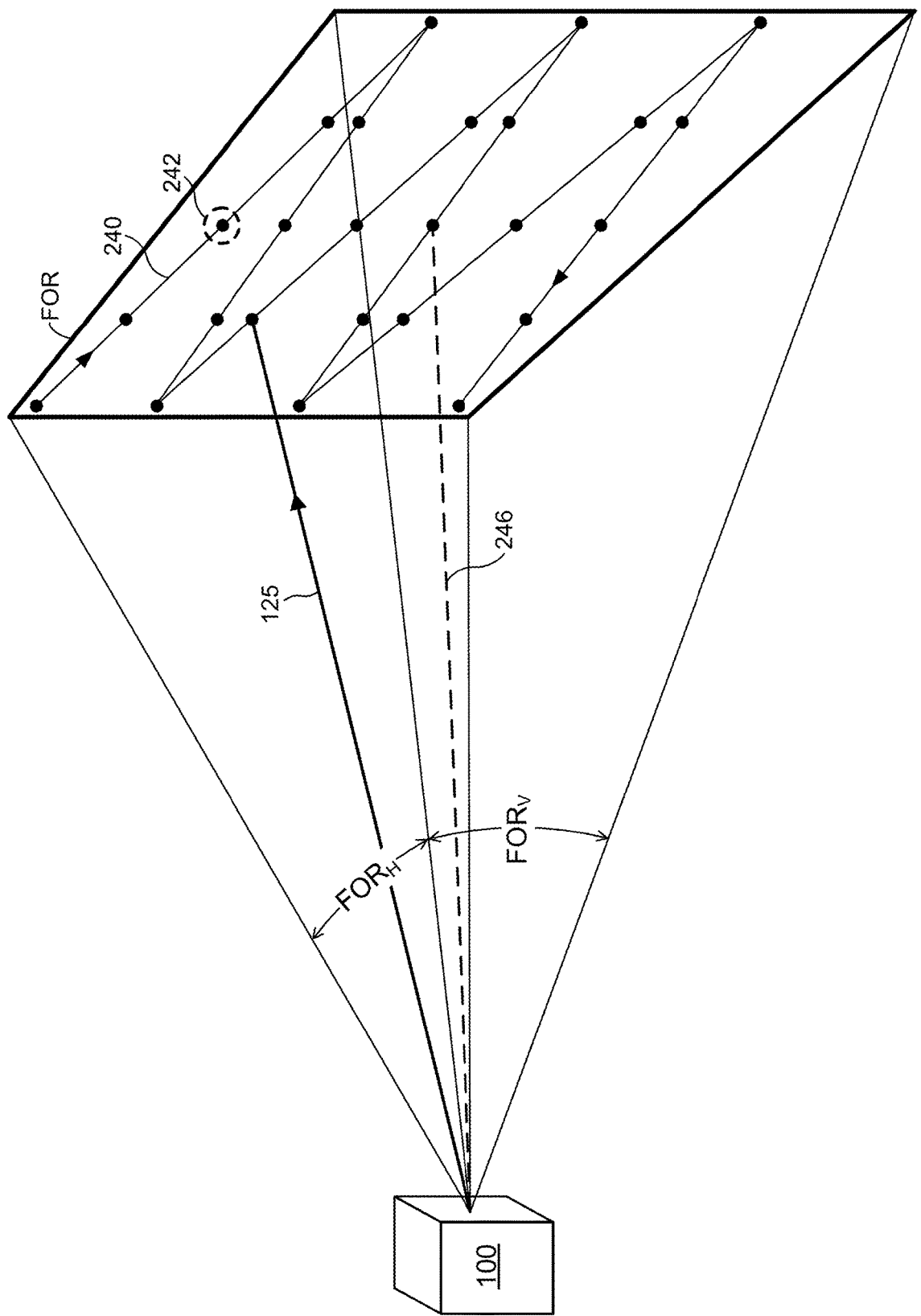
FIG. 6 illustrates an example scan pattern which the lidar system of FIG. 1 equipped with a scanner of FIG. 2 can produce when scanning a field of regard.

FIG. 6 illustrates an example scan pattern 240 which the lidar system 100 of FIG. 1 or the lidar system 200 of FIG. 3 can produce, along with an example image 241 captured by the camera 101. The scan pattern 240 overlaps the FOR of the camera 101 at least partially, and thus the lidar system 100 or 200 emits pulses in the direction of objects depicted in the image 241. However, some or all of the objects in the image 241 may be outside the maximum range of the lidar system 100 or 200.

The lidar system 100 may be configured to scan output optical beam 125 along one or more scan patterns 240. In some implementations, the scan pattern 240 corresponds to a scan across any suitable field of regard (FOR) having any suitable horizontal FOR ($FOR_H$) and any suitable vertical FOR ($FOR_V$). For example, a certain scan pattern may have a field of regard represented by angular dimensions (e.g., $FOR_H \times FOR_V$) 40°×30°, 90°×40°, or 60°×15°. As another example, a certain scan pattern may have a $FOR_H$ greater than or equal to 10°, 25°, 30°, 40°, 60°, 90°, or 120°. As yet another example, a certain scan pattern may have a $FOR_V$ greater than or equal to 2°, 5°, 10°, 15°, 20°, 30°, or 45°. In the example of FIG. 6, reference line 246 represents a center of the field of regard of scan pattern 240. The reference line 246 may have any suitable orientation, such as, a horizontal angle of 0° (e.g., reference line 246 may be oriented straight ahead) and a vertical angle of 0° (e.g., reference line 246 may have an inclination of 0°), or the reference line 246 may have a nonzero horizontal angle or a nonzero inclination (e.g., a vertical angle of +10° or −10°). In FIG. 6, if the scan pattern 240 has a 60°×15° field of regard, then the scan pattern 240 covers a ±30° horizontal range with respect to reference line 246 and a ±7.5° vertical range with respect to reference line 246. Additionally, the optical beam 125 in FIG. 6 has an orientation of approximately −15° horizontal and +3° vertical with respect to reference line 246. The beam 125 may be referred to as having an azimuth of −15° and an altitude of +3° relative to the reference line 246. An azimuth (which may be referred to as an azimuth angle) may represent a horizontal angle with respect to the reference line 246, and an altitude (which may be referred to as an altitude angle, elevation, or elevation angle) may represent a vertical angle with respect to the reference line 246. The azimuth angle also can be referred to herein as the horizontal scan angle, and altitude angle can be referred to herein as the vertical scan angle.

The scan pattern 240 may include multiple pixels 242, and each pixel 242 may be associated with one or more laser pulses and one or more corresponding distance measurements. A cycle of scan pattern 240 may include a total of $P_x \times P_y$ pixels 242 (e.g., a two-dimensional distribution of $P_x$ by $P_y$ pixels). For example, the scan pattern 240 may include a distribution with dimensions of approximately 100-2,000 pixels 242 along a horizontal direction and approximately 4-400 pixels 242 along a vertical direction. As another example, the scan pattern 240 may include a distribution of 1,000 pixels 242 along the horizontal direction by 64 pixels 242 along the vertical direction (e.g., the frame size is 1000×64 pixels) for a total of 64,000 pixels per cycle of scan pattern 240. The number of pixels 242 along a horizontal direction may be referred to as a horizontal resolution of the scan pattern 240, and the number of pixels 242 along a vertical direction may be referred to as a vertical resolution of the scan pattern 240. As an example, the scan pattern 240 may have a horizontal resolution of greater than or equal to 100 pixels 242 and a vertical resolution of greater than or equal to 4 pixels 242. As another example, the scan pattern 240 may have a horizontal resolution of 100-2,000 pixels 242 and a vertical resolution of 4-400 pixels 242.

Each pixel 242 may be associated with a distance (e.g., a distance to a portion of a target 130 from which the corresponding laser pulse was scattered) or one or more angular values. As an example, the pixel 242 may be associated with a distance value and two angular values (e.g., an azimuth and altitude) that represent the angular location of the pixel 242 with respect to the lidar system 100. A distance to a portion of the target 130 may be determined based at least in part on a time-of-flight measurement for a corresponding pulse. An angular value (e.g., an azimuth or altitude) may correspond to an angle (e.g., relative to reference line 246) of the output beam 125 (e.g., when a corresponding pulse is emitted from lidar system 100) or an angle of the input beam 135 (e.g., when an input signal is received by lidar system 100). In some implementations, the lidar system 100 determines an angular value based at least in part on a position of a component of the scanner 120. For example, an azimuth or altitude value associated with the pixel 242 may be determined from an angular position of one or more corresponding scanning mirrors of the scanner 120.

In some implementations, the lidar system 100 concurrently directs multiple beams across the field of regard. In the example implementation of FIG. 7, the lidar system generates output beams 250A, 250B, 250C, . . . 250N etc., each of which follows a linear scan pattern 254A, 254B, 254C, . . . 254N. The number of parallel lines can be 2, 4, 12, 20, or any other suitable number. The lidar system 100 may angularly separate the beams 250A, 250B, 250C, . . . 250N, so that, for example, the separation between beams 250A and 250B at a certain distance may be 30 cm, and the separation between the same beams 250A and 250B at a longer distance may be 50 cm.

Figure 7:
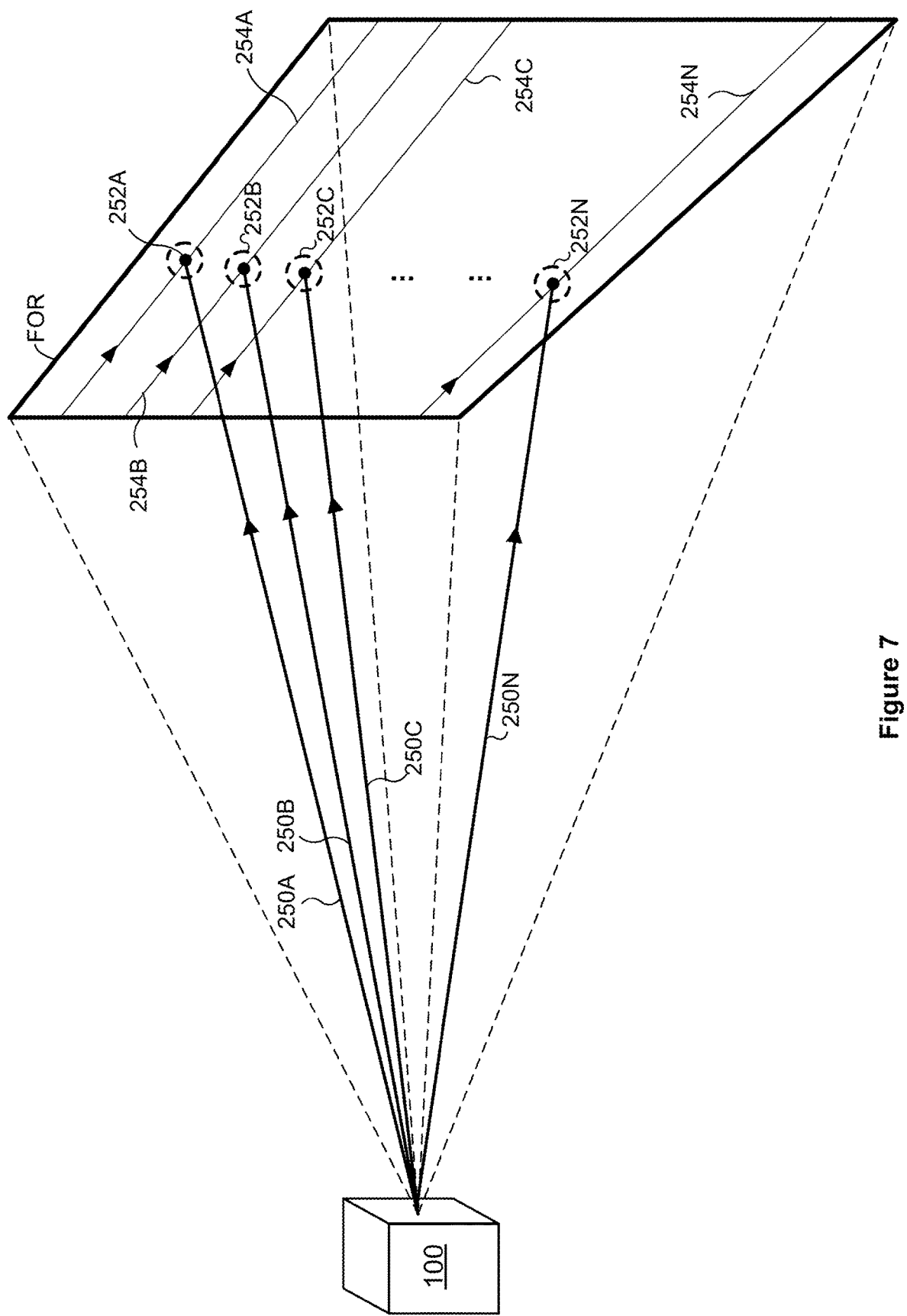
FIG. 7 illustrates an example scan pattern which the lidar system of FIG. 1 can produce when scanning a field of regard using multiple beams.

Similar to the scan pattern 240, each of the linear scan patterns 254A-N includes pixels associated with one or more laser pulses and distance measurements. FIG. 7 illustrates example pixels 252A, 252B and 252C along the scan patterns 254A, 254B and 254C, respectively. The lidar system 100 in this example may generate the values for the pixels 252A-252N at the same time, thus increasing the rate at which values for pixels are determined.

Depending on the implementation, the lidar system 100 may output the beams 250A-N at the same wavelength or different wavelengths. The beam 250A for example may have the wavelength of 1540 nm, the beam 250B may have the wavelength of 1550 nm, the beam 250C may have the wavelength of 1560 nm, etc. The number of different wavelengths the lidar system 100 uses need not match the number of beams. Thus, the lidar system 100 in the example implementation of FIG. 7 may use M wavelengths with N beams, where 1≤M≤N.

Figure 8:
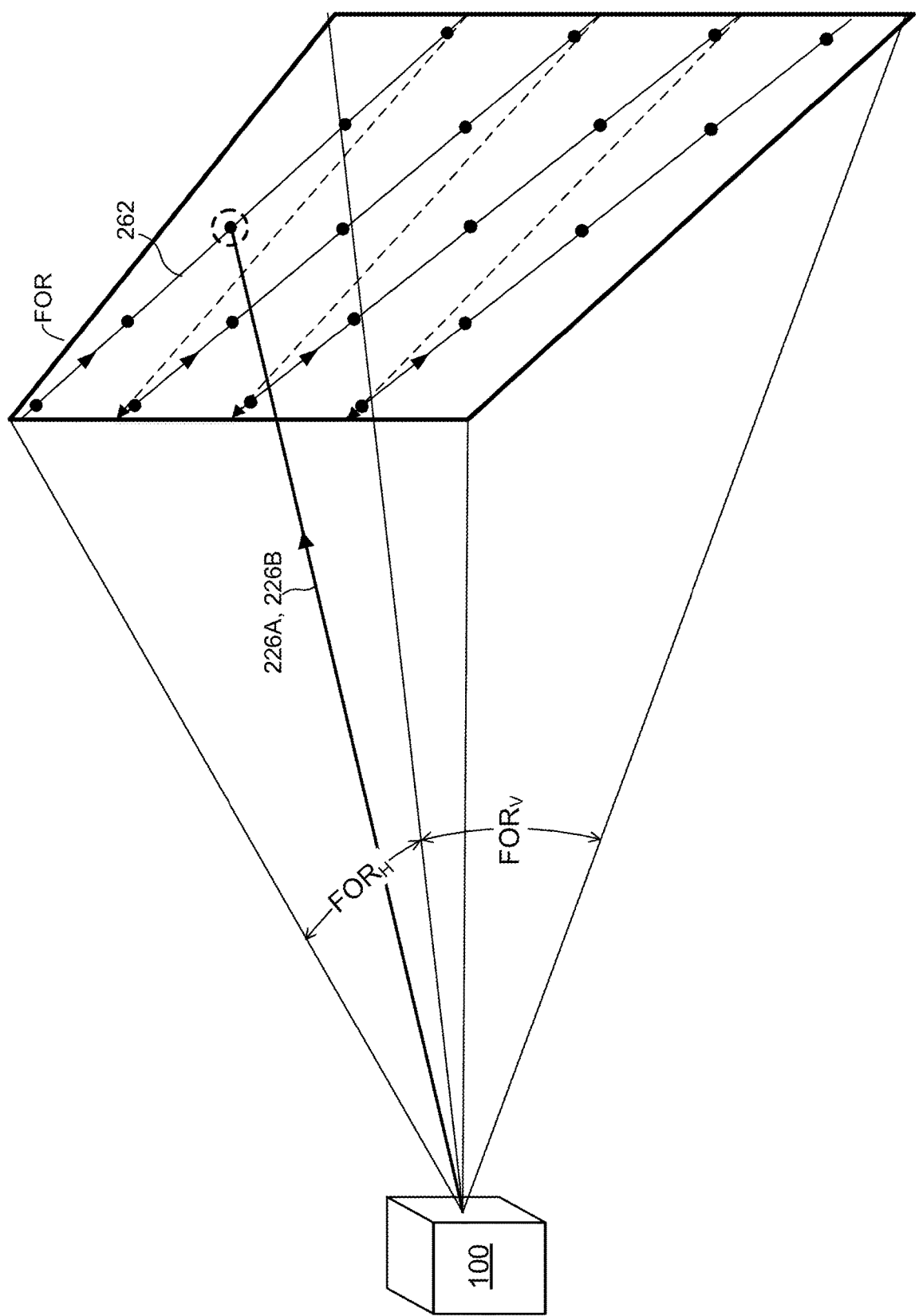
FIG. 8 illustrates an example scan pattern which the lidar system of FIG. 1 equipped with a polygon mirror can produce when scanning a field of regard.

FIG. 8 illustrates an example scan pattern which a lidar system that uses a rotating polygon mirror (e.g., the lidar system 200 of FIG. 3) can generate. The lidar in this case directs an output beam 226A or 226B along a pattern 262 made up of slanted lines (due to the oscillation of the scan mirror 212A or 212B along the vertical dimension during rotation of the polygon minor 202).

Figure 9:
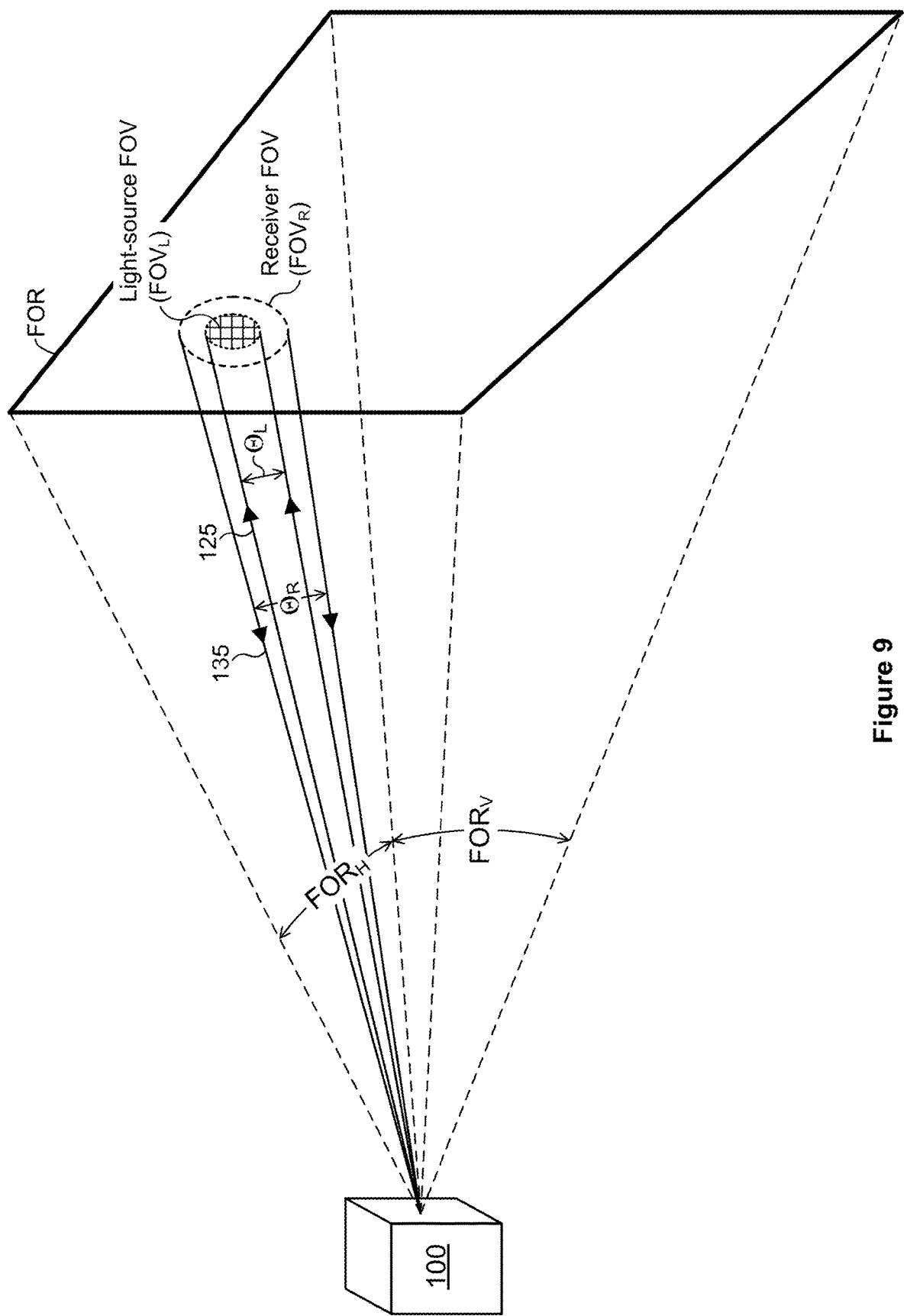
FIG. 9 schematically illustrates fields of view (FOVs) of a light source and a detector that can operate in the lidar system of FIG. 1.

Next, FIG. 9 illustrates an example light-source field of view ($FOV_L$) and receiver field of view ($FOV_R$) for the lidar system 100. The light source 110 may emit pulses of light as the $FOV_L$ and $FOV_R$ are scanned by the scanner 120 across a field of regard (FOR). The light-source field of view may refer to an angular cone illuminated by the light source 110 at a particular instant of time. Similarly, a receiver field of view may refer to an angular cone over which the receiver 140 may receive or detect light at a particular instant of time, and any light outside the receiver field of view may not be received or detected. For example, as the scanner 120 scans the light-source field of view across a field of regard, the lidar system 100 may send the pulse of light in the direction the $FOV_L$ is pointing at the time the light source 110 emits the pulse. The pulse of light may scatter off the target 130, and the receiver 140 may receive and detect a portion of the scattered light that is directed along or contained within the $FOV_R$.

An instantaneous FOV may refer to an angular cone being illuminated by a pulse directed along the direction the light-source FOV is pointing at the instant the pulse of light is emitted. Thus, while the light-source FOV and the detector FOV are scanned together in a synchronous manner (e.g., the scanner 120 scans both the light-source FOV and the detector FOV across the field of regard along the same scan direction and at the same scan speed, maintaining the same relative position to each other), the instantaneous FOV remains "stationary," and the detector FOV effectively moves relative to the instantaneous FOV. More particularly, when a pulse of light is emitted, the scanner 120 directs the pulse along the direction in which the light-source FOV currently is pointing. Each instantaneous FOV (IFOV) corresponds to a pixel. Thus, each time a pulse is emitted, the lidar system 100 produces or defines an IFOV (or pixel) that is fixed in place and corresponds to the light-source FOV at the time when the pulse is emitted. During operation of the scanner 120, the detector FOV moves relative to the light-source IFOV but does not move relative to the light-source FOV.

In some implementations, the scanner 120 is configured to scan both a light-source field of view and a receiver field of view across a field of regard of the lidar system 100. The lidar system 100 may emit and detect multiple pulses of light as the scanner 120 scans the $FOV_L$ and $FOV_R$ across the field of regard while tracing out the scan pattern 240. The scanner 120 in some implementations scans the light-source field of view and the receiver field of view synchronously with respect to one another. In this case, as the scanner 120 scans $FOV_L$ across a scan pattern 240, the $FOV_R$ follows substantially the same path at the same scanning speed. Additionally, the $FOV_L$ and $FOV_R$ may maintain the same relative position to one another as the scanner 120 scans $FOV_L$ and $FOV_R$ across the field of regard. For example, the $FOV_L$ may be substantially overlapped with or centered inside the $FOV_R$ (as illustrated in FIG. 9), and the scanner 120 may maintain this relative positioning between $FOV_L$ and $FOV_R$ throughout a scan. As another example, the $FOV_R$ may lag behind the $FOV_L$ by a particular, fixed amount throughout a scan (e.g., the $FOV_R$ may be offset from the $FOV_L$ in a direction opposite the scan direction).

The $FOV_L$ may have an angular size or extent $\Theta_L$ that is substantially the same as or that corresponds to the divergence of the output beam 125, and the $FOV_R$ may have an angular size or extent $\Theta_R$ that corresponds to an angle over which the receiver 140 may receive and detect light. The receiver field of view may be any suitable size relative to the light-source field of view. For example, the receiver field of view may be smaller than, substantially the same size as, or larger than the angular extent of the light-source field of view. In some implementations, the light-source field of view has an angular extent of less than or equal to 50 milliradians, and the receiver field of view has an angular extent of less than or equal to 50 milliradians. The $FOV_L$ may have any suitable angular extent $\Theta_L$, such as for example, approximately 0.1 mrad, 0.2 mrad, 0.5 mrad, 1 mrad, 1.5 mrad, 2 mrad, 3 mrad, 5 mrad, 10 mrad, 20 mrad, 40 mrad, or 50 mrad. Similarly, the $FOV_R$ may have any suitable angular extent $\Theta_R$, such as for example, approximately 0.1 mrad, 0.2 mrad, 0.5 mrad, 1 mrad, 1.5 mrad, 2 mrad, 3 mrad, 5 mrad, 10 mrad, 20 mrad, 40 mrad, or 50 mrad. The light-source field of view and the receiver field of view may have approximately equal angular extents. As an example, $\Theta_L$ and $\Theta_R$ may both be approximately equal to 1 mrad, 2 mrad, or 3 mrad. In some implementations, the receiver field of view is larger than the light-source field of view, or the light-source field of view is larger than the receiver field of view. For example, $\Theta_L$ may be approximately equal to 1.5 mrad, and $\Theta_R$ may be approximately equal to 3 mrad.

A pixel 242 may represent or correspond to a light-source field of view. As the output beam 125 propagates from the light source 110, the diameter of the output beam 125 (as well as the size of the corresponding pixel 242) may increase according to the beam divergence $\Theta_L$. As an example, if the output beam 125 has a $\Theta_L$ of 2 mrad, then at a distance of 100 m from the lidar system 100, the output beam 125 may have a size or diameter of approximately 20 cm, and a corresponding pixel 242 may also have a corresponding size or diameter of approximately 20 cm. At a distance of 200 m from the lidar system 100, the output beam 125 and the corresponding pixel 242 may each have a diameter of approximately 40 cm.

A Lidar System Operating in a Vehicle

As indicated above, one or more lidar systems 100 may be integrated into a vehicle. In one example implementation, multiple lidar systems 100 may be integrated into a car to provide a complete 360-degree horizontal FOR around the car. As another example, 4-10 lidar systems 100, each system having a 45-degree to 90-degree horizontal FOR, may be combined together to form a sensing system that provides a point cloud covering a 360-degree horizontal FOR. The lidar systems 100 may be oriented so that adjacent FORs have an amount of spatial or angular overlap to allow data from the multiple lidar systems 100 to be combined or stitched together to form a single or continuous 360-degree point cloud. As an example, the FOR of each lidar system 100 may have approximately 1-15 degrees of overlap with an adjacent FOR. In particular embodiments, a vehicle may refer to a mobile machine configured to transport people or cargo. For example, a vehicle may include, may take the form of, or may be referred to as a car, automobile, motor vehicle, truck, bus, van, trailer, off-road vehicle, farm vehicle, lawn mower, construction equipment, golf cart, motorhome, taxi, motorcycle, scooter, bicycle, skateboard, train, snowmobile, watercraft (e.g., a ship or boat), aircraft (e.g., a fixed-wing aircraft, helicopter, or dirigible), or spacecraft. In particular embodiments, a vehicle may include an internal combustion engine or an electric motor that provides propulsion for the vehicle.

In some implementations, one or more lidar systems 100 are included in a vehicle as part of an advanced driver assistance system (ADAS) to assist a driver of the vehicle in the driving process. For example, a lidar system 100 may be part of an ADAS that provides information or feedback to a driver (e.g., to alert the driver to potential problems or hazards) or that automatically takes control of part of a vehicle (e.g., a braking system or a steering system) to avoid collisions or accidents. The lidar system 100 may be part of a vehicle ADAS that provides adaptive cruise control, automated braking, automated parking, collision avoidance, alerts the driver to hazards or other vehicles, maintains the vehicle in the correct lane, or provides a warning if an object or another vehicle is in a blind spot.

In some cases, one or more lidar systems 100 are integrated into a vehicle as part of an autonomous-vehicle driving system. In an example implementation, the lidar system 100 provides information about the surrounding environment to a driving system of an autonomous vehicle. An autonomous-vehicle driving system may include one or more computing systems that receive information from the lidar system 100 about the surrounding environment, analyze the received information, and provide control signals to the vehicle's driving systems (e.g., steering wheel, accelerator, brake, or turn signal). For example, the lidar system 100 integrated into an autonomous vehicle may provide an autonomous-vehicle driving system with a point cloud every 0.1 seconds (e.g., the point cloud has a 10 Hz update rate, representing 10 frames per second). The autonomous-vehicle driving system may analyze the received point clouds to sense or identify targets 130 and their respective locations, distances, or speeds, and the autonomous-vehicle driving system may update control signals based on this information. As an example, if the lidar system 100 detects a vehicle ahead that is slowing down or stopping, the autonomous-vehicle driving system may send instructions to release the accelerator and apply the brakes.

An autonomous vehicle may be referred to as an autonomous car, driverless car, self-driving car, robotic car, or unmanned vehicle. An autonomous vehicle may be a vehicle configured to sense its environment and navigate or drive with little or no human input. For example, an autonomous vehicle may be configured to drive to any suitable location and control or perform all safety-critical functions (e.g., driving, steering, braking, parking) for the entire trip, with the driver not expected to control the vehicle at any time. As another example, an autonomous vehicle may allow a driver to safely turn their attention away from driving tasks in particular environments (e.g., on freeways), or an autonomous vehicle may provide control of a vehicle in all but a few environments, requiring little or no input or attention from the driver.

An autonomous vehicle may be configured to drive with a driver present in the vehicle, or an autonomous vehicle may be configured to operate the vehicle with no driver present. As an example, an autonomous vehicle may include a driver's seat with associated controls (e.g., steering wheel, accelerator pedal, and brake pedal), and the vehicle may be configured to drive with no one seated in the driver's seat or with little or no input from a person seated in the driver's seat. As another example, an autonomous vehicle may not include any driver's seat or associated driver's controls, and the vehicle may perform substantially all driving functions (e.g., driving, steering, braking, parking, and navigating) without human input. As another example, an autonomous vehicle may be configured to operate without a driver (e.g., the vehicle may be configured to transport human passengers or cargo without a driver present in the vehicle). As another example, an autonomous vehicle may be configured to operate without any human passengers (e.g., the vehicle may be configured for transportation of cargo without having any human passengers onboard the vehicle).

In some implementations, a light source of a lidar system is located remotely from some of the other components of the lidar system such as the scanner and the receiver. Moreover, a lidar system implemented in a vehicle may include fewer light sources than scanners and receivers.

Figure 10:
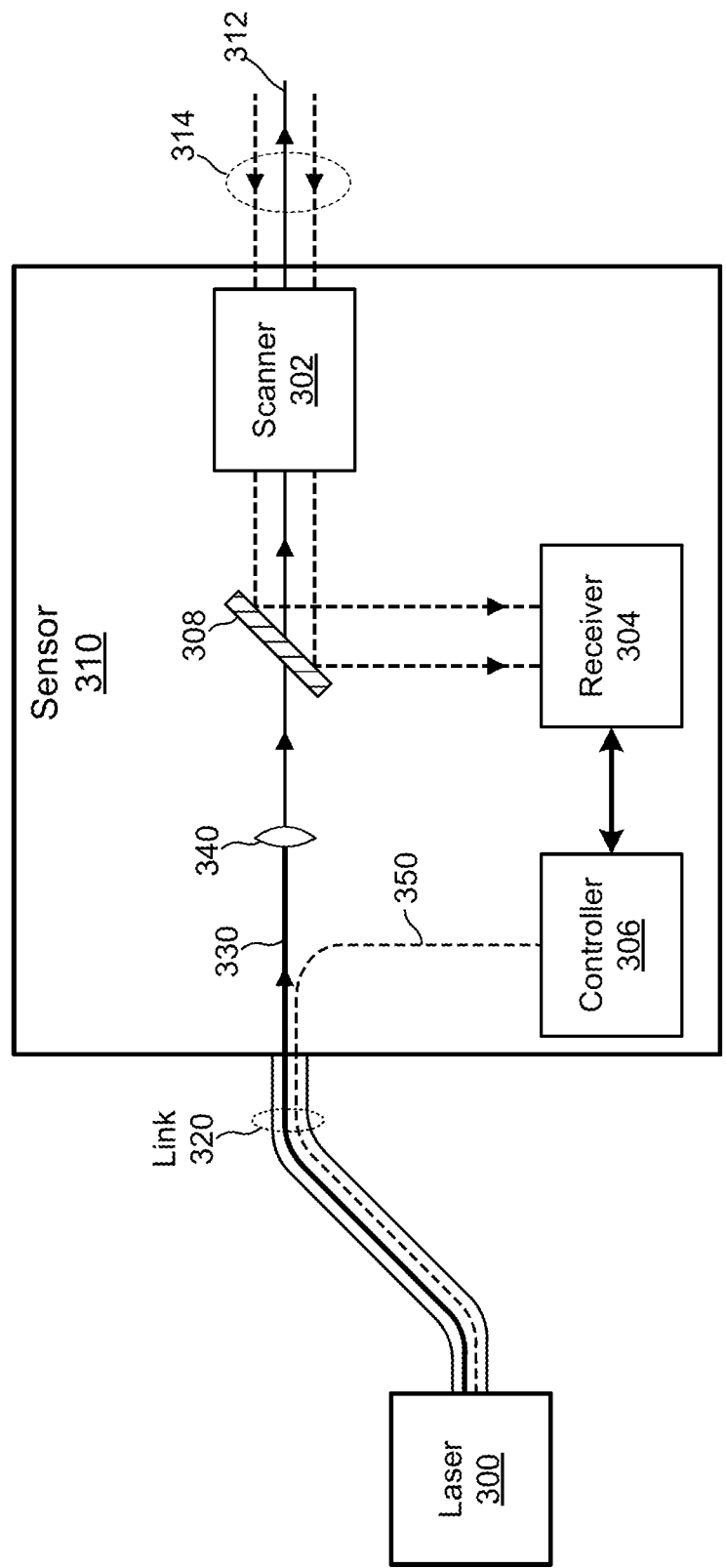
FIG. 10 illustrates an example configuration of the lidar system of FIG. 1 or another suitable lidar system, in which a laser is disposed away from sensor components.

FIG. 10 illustrates an example configuration in which a laser-sensor link 320 includes an optical link 330 and an electrical link 350 coupled between a laser 300 and a sensor 310. The laser 300 may be configured to emit pulses of light and may be referred to as a laser system, laser head, or light source. The laser 300 may include, may be part of, may be similar to, or may be substantially the same as the light source 110 illustrated in FIG. 1 and discussed above. Further, the scanner 302, the receiver 304, the controller 306, and the mirror 308 may be similar to the scanner 120, the receiver 140, the controller 150, and the mirror 115 discussed above. In the example of FIG. 10, the laser 300 is coupled to the remotely located sensor 310 by a laser-sensor link 320 (which may be referred to as a link). The sensor 310 may be referred to as a sensor head and may include the mirror 308, the scanner 302, the receiver 304, and the controller 306. In an example implementation, the laser 300 includes a pulsed laser diode (e.g., a pulsed DFB laser) followed by an optical amplifier, and light from the laser 300 is conveyed by an optical fiber of the laser-sensor link 320 of a suitable length to the scanner 120 in a remotely located sensor 310.

The laser-sensor link 320 may include any suitable number of optical links 330 (e.g., 0, 1, 2, 3, 5, or 10) and any suitable number of electrical links 350 (e.g., 0, 1, 2, 3, 5, or 10). In the example configuration depicted in FIG. 10, the laser-sensor link 320 includes one optical link 330 from the laser 300 to an output collimator 340 and one electrical link 350 that connects the laser 300 to the controller 150. The optical link 330 may include optical fiber (which may be referred to as fiber-optic cable or fiber) that conveys, carries, transports, or transmits light between the laser 300 and the sensor 310. The optical fiber may be, for example, single-mode (SM) fiber, multi-mode (MM) fiber, large-mode-area (LMA) fiber, polarization-maintaining (PM) fiber, photonic-crystal or photonic-bandgap fiber, gain fiber (e.g., rare-earth-doped optical fiber for use in an optical amplifier), or any suitable combination thereof. The output collimator 340 receives optical pulses conveyed from the laser 300 by the optical link 330 and produces a free-space optical beam 312 that includes the optical pulses. The output collimator 340 directs the free-space optical beam 312 through the mirror 308 and to the scanner 302.

The electrical link 350 may include electrical wire or cable (e.g., a coaxial cable or twisted-pair cable) that conveys or transmits electrical power and/or one or more electrical signals between the laser 300 and the sensor 310. For example, the laser 300 may include a power supply or a power conditioner that provides electrical power to the laser 300, and additionally, the power supply or power conditioner may provide power to one or more components of the sensor 310 (e.g., the scanner 304, the receiver 304, and/or the controller 306) via the one or more electrical links 350. The electrical link 350 in some implementations may convey electrical signals that include data or information in analog or digital format. Further, the electrical link 350 may provide an interlock signal from the sensor 310 to the laser 300. If the controller 306 detects a fault condition indicating a problem with the sensor 310 or the overall lidar system, the controller 306 may change a voltage on the interlock line (e.g., from 5 V to 0 V) indicating that the laser 300 should shut down, stop emitting light, or reduce the power or energy of emitted light. A fault condition may be triggered by a failure of the scanner 302, a failure of the receiver 304, or by a person or object coming within a threshold distance of the sensor 310 (e.g., within 0.1 m, 0.5 m, 1 m, 5 m, or any other suitable distance).

As discussed above, a lidar system can include one or more processors to determine a distance D to a target. In the implementation illustrated in FIG. 10, the controller 306 may be located in the laser 300 or in the sensor 310, or parts of the controller 150 may be distributed between the laser 300 and the sensor 310. In an example implementation, each sensor head 310 of a lidar system includes electronics (e.g., an electronic filter, transimpedance amplifier, threshold detector, or time-to-digital (TDC) converter) configured to receive or process a signal from the receiver 304 or from an APD or SPAD of the receiver 304. Additionally, the laser 300 may include processing electronics configured to determine a time-of-flight value or a distance to the target based on a signal received from the sensor head 310 via the electrical link 350.

Figure 11:
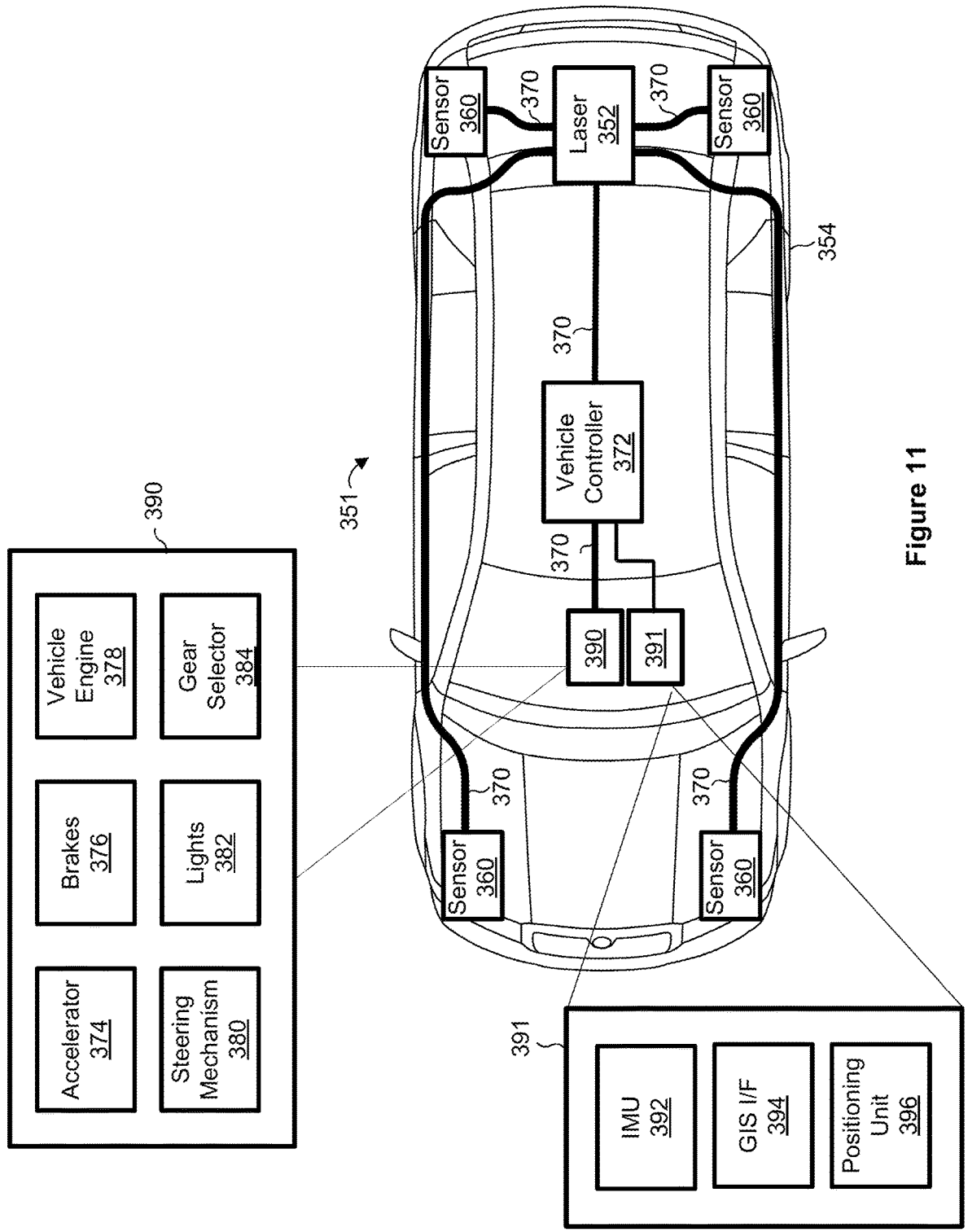
FIG. 11 illustrates an example vehicle in which the lidar system of FIG. 1 can operate.

Next, FIG. 11 illustrates an example vehicle 354 with a lidar system 351 that includes a laser 352 with multiple sensor heads 360 coupled to the laser 352 via multiple laser-sensor links 370. The laser 352 and the sensor heads 360 may be similar to the laser 300 and the sensor 310 discussed above, in some implementations. For example, each of the laser-sensor links 370 may include one or more optical links and/or one or more electrical links. The sensor heads 360 in FIG. 11 are positioned or oriented to provide a greater than 30-degree view of an environment around the vehicle. More generally, a lidar system with multiple sensor heads may provide a horizontal field of regard around a vehicle of approximately 30°, 45°, 60°, 90°, 120°, 180°, 270°, or 360°. Each of the sensor heads may be attached to or incorporated into a bumper, fender, grill, side panel, spoiler, roof, headlight assembly, taillight assembly, rear-view mirror assembly, hood, trunk, window, or any other suitable part of the vehicle.

In the example of FIG. 11, four sensor heads 360 are positioned at or near the four corners of the vehicle (e.g., the sensor heads may be incorporated into a light assembly, side panel, bumper, or fender), and the laser 352 may be located within the vehicle (e.g., in or near the trunk). The four sensor heads 360 may each provide a 90° to 120° horizontal field of regard (FOR), and the four sensor heads 360 may be oriented so that together they provide a complete 360-degree view around the vehicle. As another example, the lidar system 351 may include six sensor heads 360 positioned on or around a vehicle, where each of the sensor heads 360 provides a 60° to 90° horizontal FOR. As another example, the lidar system 351 may include eight sensor heads 360, and each of the sensor heads 360 may provide a 45° to 60° horizontal FOR. As yet another example, the lidar system 351 may include six sensor heads 360, where each of the sensor heads 360 provides a 70° horizontal FOR with an overlap between adjacent FORs of approximately 10°. As another example, the lidar system 351 may include two sensor heads 360 which together provide a forward-facing horizontal FOR of greater than or equal to 30°.

Data from each of the sensor heads 360 may be combined or stitched together to generate a point cloud that covers a greater than or equal to 30-degree horizontal view around a vehicle. For example, the laser 352 may include a controller or processor that receives data from each of the sensor heads 360 (e.g., via a corresponding electrical link 370) and processes the received data to construct a point cloud covering a 360-degree horizontal view around a vehicle or to determine distances to one or more targets. The point cloud or information from the point cloud may be provided to a vehicle controller 372 via a corresponding electrical, optical, or radio link 370. In some implementations, the point cloud is generated by combining data from each of the multiple sensor heads 360 at a controller included within the laser 352 and provided to the vehicle controller 372. In other implementations, each of the sensor heads 360 includes a controller or process that constructs a point cloud for a portion of the 360-degree horizontal view around the vehicle and provides the respective point cloud to the vehicle controller 372. The vehicle controller 372 then combines or stitches together the points clouds from the respective sensor heads 360 to construct a combined point cloud covering a 360-degree horizontal view. Still further, the vehicle controller 372 in some implementations communicates with a remote server to process point cloud data.

In any event, the vehicle 354 may be an autonomous vehicle where the vehicle controller 372 provides control signals to various components 390 within the vehicle 354 to maneuver and otherwise control operation of the vehicle 354. The components 390 are depicted in an expanded view in FIG. 11 for ease of illustration only. The components 390 may include an accelerator 374, brakes 376, a vehicle engine 378, a steering mechanism 380, lights 382 such as brake lights, head lights, reverse lights, emergency lights, etc., a gear selector 384, and/or other suitable components that effectuate and control movement of the vehicle 354. The gear selector 384 may include the park, reverse, neutral, drive gears, etc. Each of the components 390 may include an interface via which the component receives commands from the vehicle controller 372 such as "increase speed," "decrease speed," "turn left 5 degrees," "activate left turn signal," etc. and, in some cases, provides feedback to the vehicle controller 372.

In some implementations, the vehicle controller 372 receives point cloud data from the laser 352 or sensor heads 360 via the link 370 and analyzes the received point cloud data to sense or identify targets 130 and their respective locations, distances, speeds, shapes, sizes, type of target (e.g., vehicle, human, tree, animal), etc. The vehicle controller 372 then provides control signals via the link 370 to the components 390 to control operation of the vehicle based on the analyzed information. For example, the vehicle controller 372 may identify an intersection based on the point cloud data and determine that the intersection is the appropriate location at which to make a left turn. Accordingly, the vehicle controller 372 may provide control signals to the steering mechanism 380, the accelerator 374, and brakes 376 for making a proper left turn. In another example, the vehicle controller 372 may identify a traffic light based on the point cloud data and determine that the vehicle 354 needs to come to a stop. As a result, the vehicle controller 372 may provide control signals to release the accelerator 374 and apply the brakes 376.

Example Receiver Implementation

Figure 12:
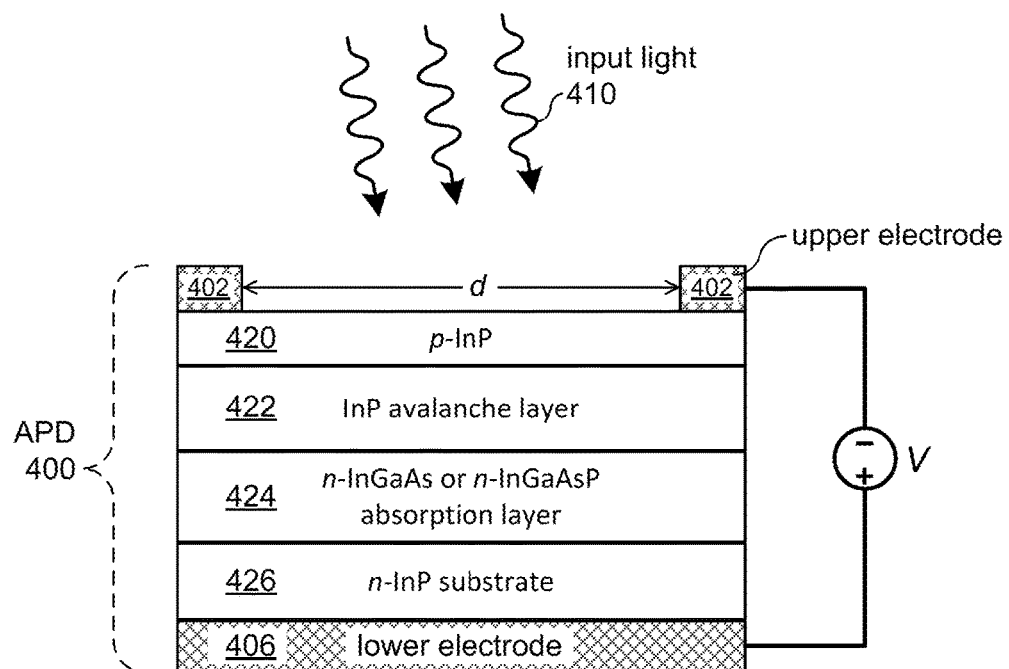
FIG. 12 illustrates an example InGaAs avalanche photodiode which can operate in the lidar system of FIG. 1.

FIG. 12 illustrates an example InGaAs avalanche photodiode (APD) 400. Referring back to FIG. 1, the receiver 140 may include one or more APDs 400 configured to receive and detect light from input light such as the beam 135. More generally, the APD 400 can operate in any suitable receiver of input light. The APD 400 may be configured to detect a portion of pulses of light which are scattered by a target located downrange from the lidar system in which the APD 400 operates. For example, the APD 400 may receive a portion of a pulse of light scattered by the target 130 depicted in FIG. 1, and generate an electrical-current signal corresponding to the received pulse of light.

The APD 400 may include doped or undoped layers of any suitable semiconductor material, such as for example, silicon, germanium, InGaAs, InGaAsP, or indium phosphide (InP). Additionally, the APD 400 may include an upper electrode 402 and a lower electrode 406 for coupling the ADP 400 to an electrical circuit. The APD 400 for example may be electrically coupled to a voltage source that supplies a reverse-bias voltage V to the APD 400. Additionally, the APD 400 may be electrically coupled to a transimpedance amplifier which receives electrical current generated by the APD 400 and produces an output voltage signal that corresponds to the received current. The upper electrode 402 or lower electrode 406 may include any suitable electrically conductive material, such as for example a metal (e.g., gold, copper, silver, or aluminum), a transparent conductive oxide (e.g., indium tin oxide), a carbon-nanotube material, or polysilicon. In some implementations, the upper electrode 402 is partially transparent or has an opening to allow input light 410 to pass through to the active region of the APD 400. In FIG. 12, the upper electrode 402 may have a ring shape that at least partially surrounds the active region of the APD 400, where the active region refers to an area over which the APD 400 may receive and detect the input light 410. The active region may have any suitable size or diameter d, such as for example, a diameter of approximately 25 μm, 50 μm, 80 μm, 100 μm, 200 μm, 500 μm, 1 mm, 2 mm, or 5 mm.

The APD 400 may include any suitable combination of any suitable semiconductor layers having any suitable doping (e.g., n-doped, p-doped, or intrinsic undoped material). In the example of FIG. 12, the InGaAs APD 400 includes a p-doped InP layer 420, an InP avalanche layer 422, an absorption layer 424 with n-doped InGaAs or InGaAsP, and an n-doped InP substrate layer 426. Depending on the implementation, the APD 400 may include separate absorption and avalanche layers, or a single layer may act as both an absorption and avalanche region. The APD 400 may operate electrically as a PN diode or a PIN diode, and, during operation, the APD 400 may be reverse-biased with a positive voltage V applied to the lower electrode 406 with respect to the upper electrode 402. The applied reverse-bias voltage V may have any suitable value, such as for example approximately 5 V, 10 V, 20 V, 30 V, 50 V, 75 V, 100 V, or 200 V.

In FIG. 12, photons of the input light 410 may be absorbed primarily in the absorption layer 424, resulting in the generation of electron-hole pairs (which may be referred to as photo-generated carriers). For example, the absorption layer 424 may be configured to absorb photons corresponding to the operating wavelength of the lidar system 100 (e.g., any suitable wavelength between approximately 1400 nm and approximately 1600 nm). In the avalanche layer 422, an avalanche-multiplication process occurs where carriers (e.g., electrons or holes) generated in the absorption layer 424 collide with the semiconductor lattice of the absorption layer 424, and produce additional carriers through impact ionization. This avalanche process can repeat numerous times so that one photo-generated carrier may result in the generation of multiple carriers. As an example, a single photon absorbed in the absorption layer 424 may lead to the generation of approximately 10, 50, 100, 200, 500, 1000, 10,000, or any other suitable number of carriers through an avalanche-multiplication process. The carriers generated in an APD 400 may produce an electrical current that is coupled to an electrical circuit which may perform signal amplification, sampling, filtering, signal conditioning, analog-to-digital conversion, time-to-digital conversion, pulse detection, threshold detection, rising-edge detection, or falling-edge detection.

The number of carriers generated from a single photo-generated carrier may increase as the applied reverse bias V is increased. If the applied reverse bias V is increased above a particular value referred to as the APD breakdown voltage, then a single carrier can trigger a self-sustaining avalanche process (e.g., the output of the APD 400 is saturated regardless of the input light level). The APD 400 that is operated at or above a breakdown voltage may be referred to as a single-photon avalanche diode (SPAD) and may be referred to as operating in a Geiger mode or a photon-counting mode. The APD 400 that is operated below a breakdown voltage may be referred to as a linear APD, and the output current generated by the APD 400 may be sent to an amplifier circuit (e.g., a transimpedance amplifier). The receiver 140 (see FIG. 1) may include an APD configured to operate as a SPAD and a quenching circuit configured to reduce a reverse-bias voltage applied to the SPAD when an avalanche event occurs in the SPAD. The APD 400 configured to operate as a SPAD may be coupled to an electronic quenching circuit that reduces the applied voltage V below the breakdown voltage when an avalanche-detection event occurs. Reducing the applied voltage may halt the avalanche process, and the applied reverse-bias voltage may then be re-set to await a subsequent avalanche event. Additionally, the APD 400 may be coupled to a circuit that generates an electrical output pulse or edge when an avalanche event occurs.

In some implementations, the APD 400 or the APD 400 along with transimpedance amplifier have a noise-equivalent power (NEP) that is less than or equal to 100 photons, 50 photons, 30 photons, 20 photons, or 10 photons. For example, the APD 400 may be operated as a SPAD and may have a NEP of less than or equal to 20 photons. As another example, the APD 400 may be coupled to a transimpedance amplifier that produces an output voltage signal with a NEP of less than or equal to 50 photons. The NEP of the APD 400 is a metric that quantifies the sensitivity of the APD 400 in terms of a minimum signal (or a minimum number of photons) that the APD 400 can detect. The NEP may correspond to an optical power (or to a number of photons) that results in a signal-to-noise ratio of 1, or the NEP may represent a threshold number of photons above which an optical signal may be detected. For example, if the APD 400 has a NEP of 20 photons, then the input beam 410 with 20 photons may be detected with a signal-to-noise ratio of approximately 1 (e.g., the APD 400 may receive 20 photons from the input beam 410 and generate an electrical signal representing the input beam 410 that has a signal-to-noise ratio of approximately 1). Similarly, the input beam 410 with 100 photons may be detected with a signal-to-noise ratio of approximately 5. In some implementations, the lidar system 100 with the APD 400 (or a combination of the APD 400 and transimpedance amplifier) having a NEP of less than or equal to 100 photons, 50 photons, 30 photons, 20 photons, or 10 photons offers improved detection sensitivity with respect to a conventional lidar system that uses a PN or PIN photodiode. For example, an InGaAs PIN photodiode used in a conventional lidar system may have a NEP of approximately $10^4$ to $10^5$ photons, and the noise level in a lidar system with an InGaAs PIN photodiode may be $10^3$ to $10^4$ times greater than the noise level in a lidar system 100 with the InGaAs APD detector 400.

Referring back to FIG. 1, an optical filter may be located in front of the receiver 140 and configured to transmit light at one or more operating wavelengths of the light source 110 and attenuate light at surrounding wavelengths. For example, an optical filter may be a free-space spectral filter located in front of APD 400 of FIG. 12. This spectral filter may transmit light at the operating wavelength of the light source 110 (e.g., between approximately 1530 nm and 1560 nm) and attenuate light outside that wavelength range. As a more specific example, light with wavelengths of approximately 400-1530 nm or 1560-2000 nm may be attenuated by any suitable amount, such as for example, by at least 5 dB, 10 dB, 20 dB, 30 dB, or 40 dB.

Figure 13:
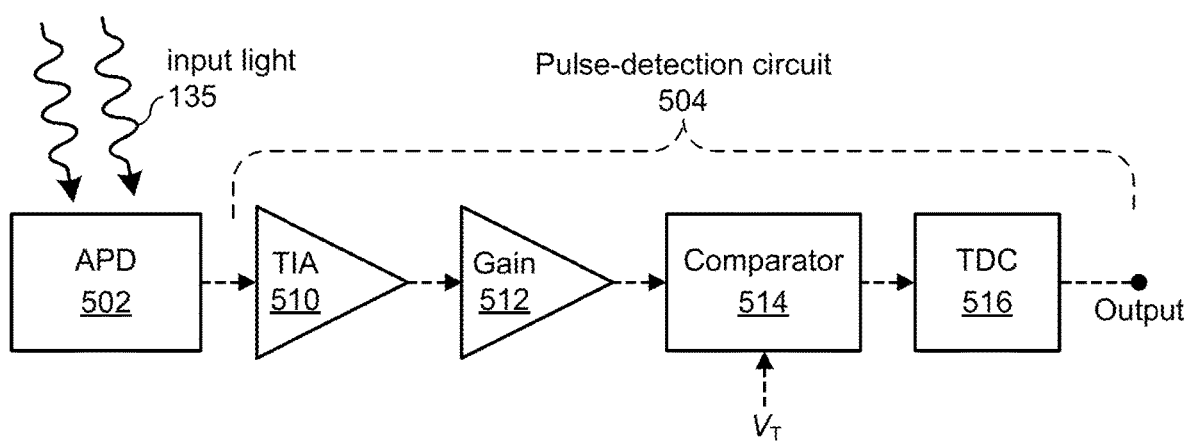
FIG. 13 illustrates an example photodiode coupled to a pulse-detection circuit, which can operate in the lidar system of FIG. 1.

Next, FIG. 13 illustrates an APD 502 coupled to an example pulse-detection circuit 504. The APD 502 can be similar to the APD 400 discussed above with reference to FIG. 10, or can be any other suitable detector. The pulse-detection circuit 504 can operate in the lidar system of FIG. 1 as part of the receiver 140. Further, the pulse-detection circuit 504 can operate in the receiver 164 of FIG. 2, the receiver 304 of FIG. 10, or any other suitable receiver. The pulse-detection circuit 504 alternatively can be implemented in the controller 150, the controller 306, or another suitable controller. In some implementations, parts of the pulse-detection circuit 504 can operate in a receiver and other parts of the pulse-detection circuit 504 can operate in a controller. For example, components 510 and 512 may be a part of the receiver 140, and components 514 and 516 may be a part of the controller 150.

The pulse-detection circuit 504 may include circuitry that receives a signal from a detector (e.g., an electrical current from the APD 502) and performs current-to-voltage conversion, signal amplification, sampling, filtering, signal conditioning, analog-to-digital conversion, time-to-digital conversion, pulse detection, threshold detection, rising-edge detection, or falling-edge detection. The pulse-detection circuit 504 may determine whether an optical pulse has been received by the APD 502 or may determine a time associated with receipt of an optical pulse by the APD 502. Additionally, the pulse-detection circuit 504 may determine a duration of a received optical pulse. In an example implementation, the pulse-detection circuit 504 includes a transimpedance amplifier (TIA) 510, a gain circuit 512, a comparator 514, and a time-to-digital converter (TDC) 516.

The TIA 510 may be configured to receive an electrical-current signal from the APD 502 and produce a voltage signal that corresponds to the received electrical-current signal. For example, in response to a received optical pulse, the APD 502 may produce a current pulse corresponding to the optical pulse. The TIA 510 may receive the current pulse from the APD 502 and produce a voltage pulse that corresponds to the received current pulse. The TIA 510 may also act as an electronic filter. For example, the TIA 510 may be configured as a low-pass filter that removes or attenuates high-frequency electrical noise by attenuating signals above a particular frequency (e.g., above 1 MHz, 10 MHz, 20 MHz, 50 MHz, 100 MHz, 200 MHz, or any other suitable frequency).

The gain circuit 512 may be configured to amplify a voltage signal. As an example, the gain circuit 512 may include one or more voltage-amplification stages that amplify a voltage signal received from the TIA 510. For example, the gain circuit 512 may receive a voltage pulse from the TIA 510, and the gain circuit 512 may amplify the voltage pulse by any suitable amount, such as for example, by a gain of approximately 3 dB, 10 dB, 20 dB, 30 dB, 40 dB, or 50 dB. Additionally, the gain circuit 512 may also act as an electronic filter configured to remove or attenuate electrical noise.

The comparator 514 may be configured to receive a voltage signal from the TIA 510 or the gain circuit 512 and produce an electrical-edge signal (e.g., a rising edge or a falling edge) when the received voltage signal rises above or falls below a particular threshold voltage $V_T$. As an example, when a received voltage rises above $V_T$, the comparator 514 may produce a rising-edge digital-voltage signal (e.g., a signal that steps from approximately 0 V to approximately 2.5 V, 3.3 V, 5 V, or any other suitable digital-high level). As another example, when a received voltage falls below $V_T$, the comparator 514 may produce a falling-edge digital-voltage signal (e.g., a signal that steps down from approximately 2.5 V, 3.3 V, 5 V, or any other suitable digital-high level to approximately 0 V). The voltage signal received by the comparator 514 may be received from the TIA 510 or the gain circuit 512 and may correspond to an electrical-current signal generated by the APD 502. For example, the voltage signal received by the comparator 514 may include a voltage pulse that corresponds to an electrical-current pulse produced by the APD 502 in response to receiving an optical pulse. The voltage signal received by the comparator 514 may be an analog signal, and an electrical-edge signal produced by the comparator 514 may be a digital signal.

The time-to-digital converter (TDC) 516 may be configured to receive an electrical-edge signal from the comparator 514 and determine an interval of time between emission of a pulse of light by the light source and receipt of the electrical-edge signal. The output of the TDC 516 may be a numerical value that corresponds to the time interval determined by the TDC 516. In some implementations, the TDC 516 has an internal counter or clock with any suitable period, such as for example, 5 ps, 10 ps, 15 ps, 20 ps, 30 ps, 50 ps, 100 ps, 0.5 ns, 1 ns, 2 ns, 5 ns, or 10 ns. The TDC 516 for example may have an internal counter or clock with a 20 ps period, and the TDC 516 may determine that an interval of time between emission and receipt of a pulse is equal to 25,000 time periods, which corresponds to a time interval of approximately 0.5 microseconds. Referring back to FIG. 1, the TDC 516 may send the numerical value "25000" to a processor or controller 150 of the lidar system 100, which may include a processor configured to determine a distance from the lidar system 100 to the target 130 based at least in part on an interval of time determined by a TDC 516. The processor may receive a numerical value (e.g., "25000") from the TDC 516 and, based on the received value, the processor may determine the distance from the lidar system 100 to a target 130.

Operating a Dual-Mode Lidar System

Figure 14:
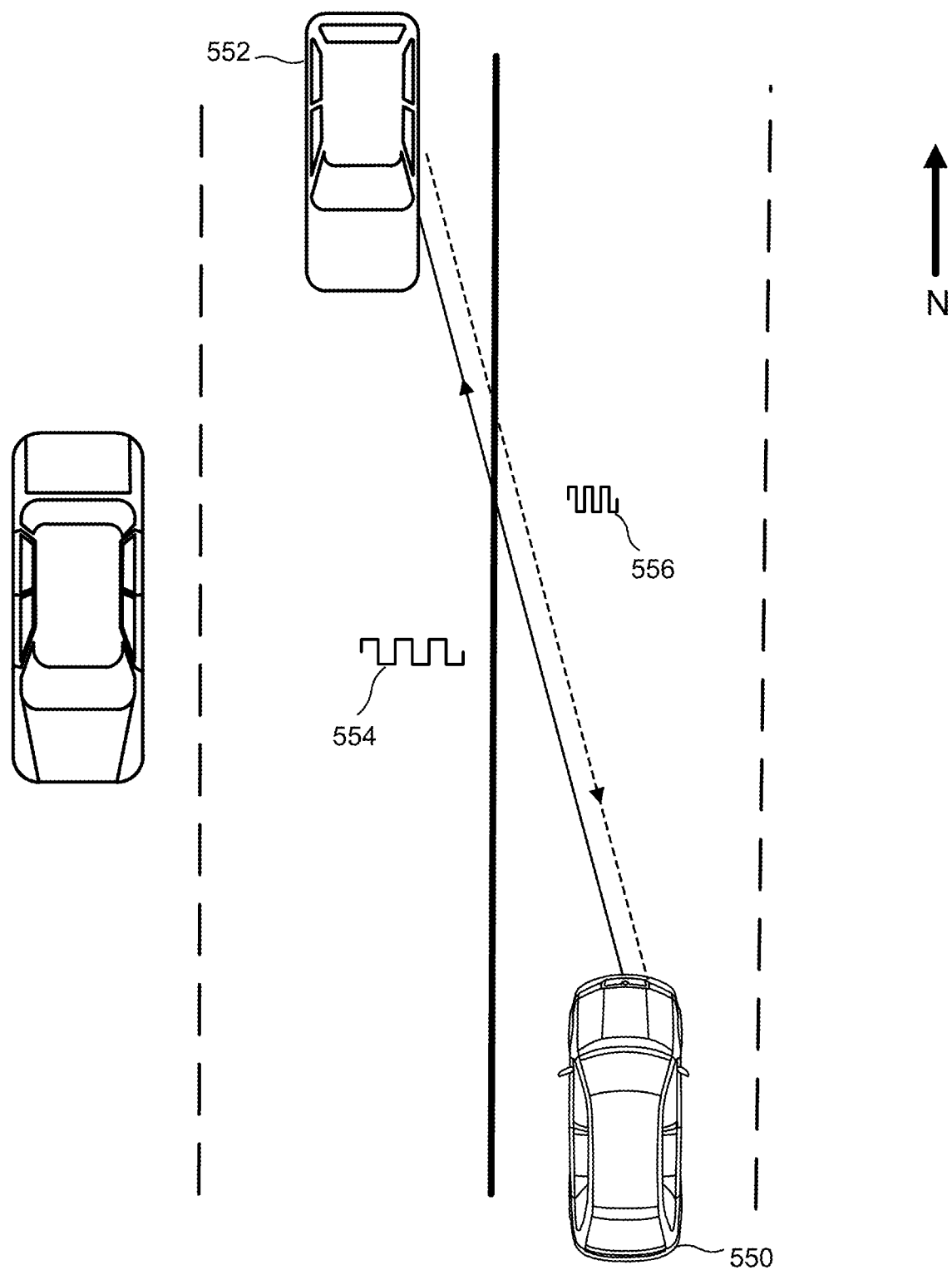
FIG. 14 illustrates an example scenario in which a vehicle equipped with a dual-mode lidar system of this disclosure detects the distance to, and the velocity of, a target headed generally toward the vehicle.
Figure 15:
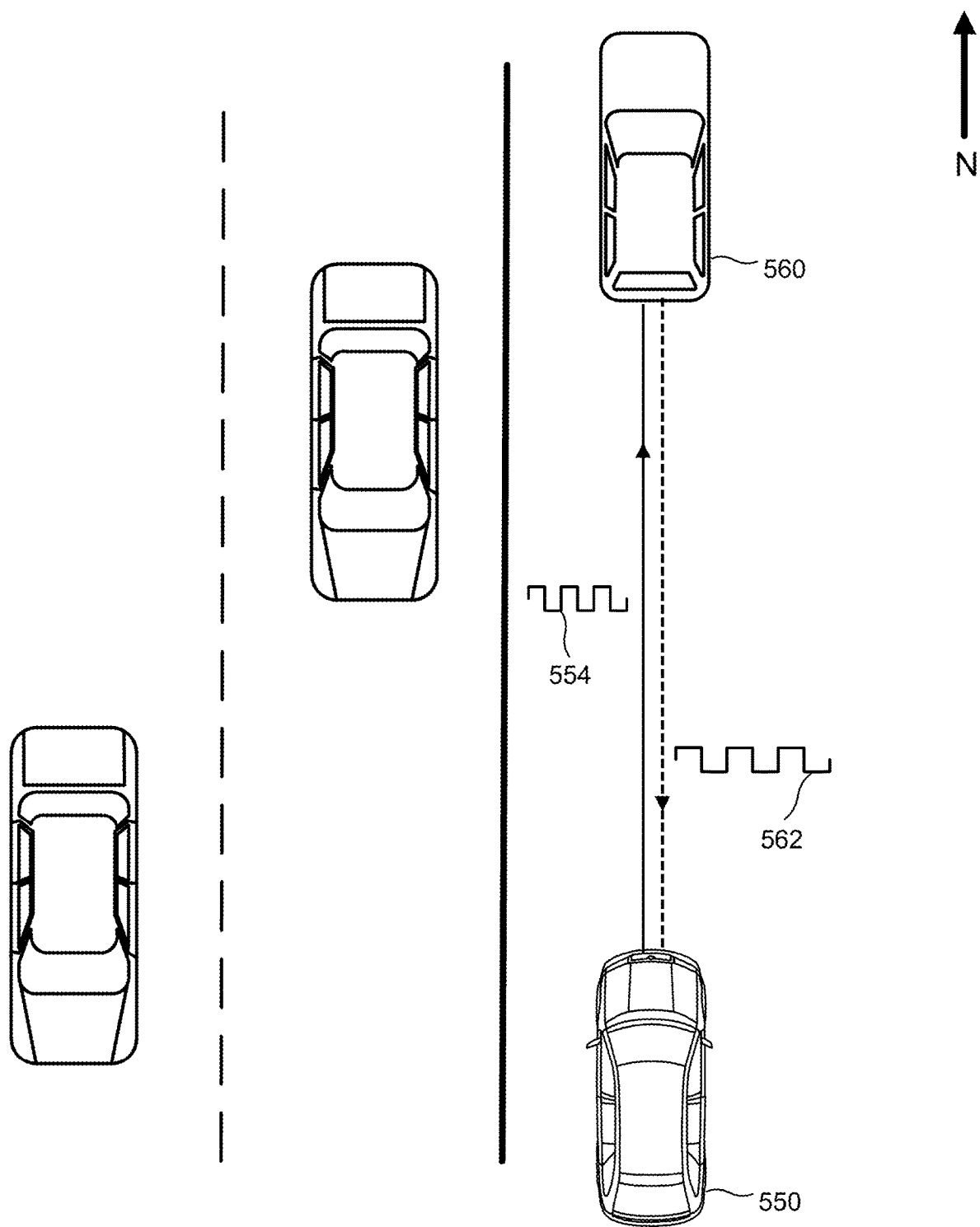
FIG. 15 illustrates an example scenario in which a vehicle equipped with a dual-mode lidar system of this disclosure detects the distance to, and the velocity of, a target headed generally away from the vehicle.
Figure 16:
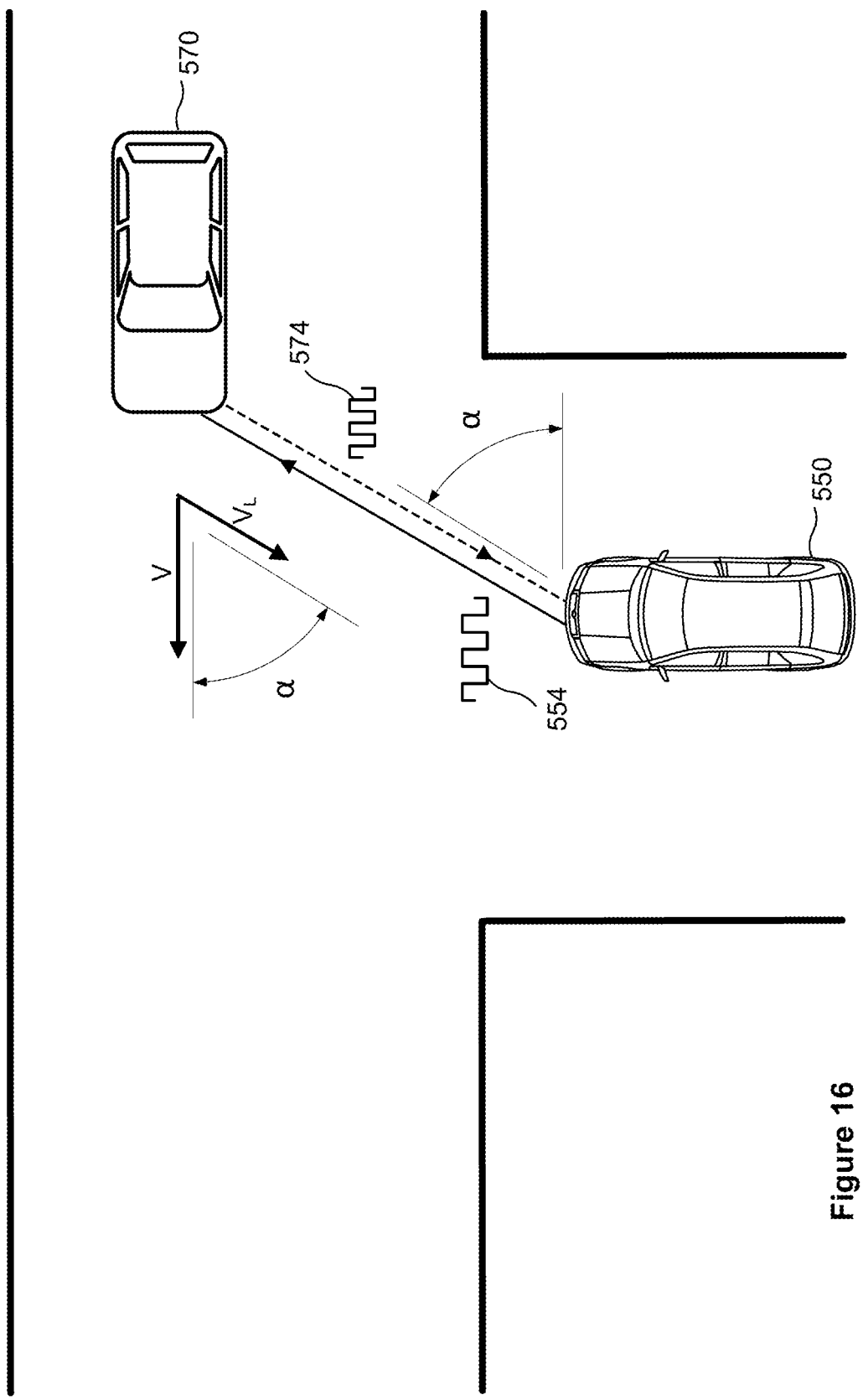
FIG. 16 illustrates an example scenario in which a vehicle equipped with a lidar system of this disclosure detects the distance to, and the velocity of, a target moving along a line generally perpendicular to the forward-facing direction of the vehicle.

Now referring to FIGS. 14-16, an example vehicle 550 is equipped with a dual-mode lidar system capable of determining the distance to a target as well as a relative velocity of the target, i.e., the velocity of the target relative to the vehicle 550. In each of these scenarios, the vehicle 550 generates a pulse to determine a distance to another vehicle and then a pulse train 554 in which successive pulses are separated by equal time intervals. The pulse train in general need not be characterized by equal time intervals, however, as discussed in more detail below.

When the target is traveling at approximately the same speed as the vehicle 550 in approximately the same direction, the relative velocity of the target is approximately 0 mph. When the vehicle 550 is travelling at 30 mph and the target is travelling in the same direction at 40 mph, for example, the relative velocity is +10 mph. On the other hand, when an oncoming vehicle is travelling at 20 mph in the opposite direction, the target in this case has the relatively velocity of −50 mph, where the negative sign indicates that the lidar system and the target are moving toward each other.

In the scenario of FIG. 14, a vehicle 552 is moving substantially toward the vehicle 550. The angles at which pulses are emitted are illustrated in FIG. 4 in an exaggerated manner for clarity. When the vehicle 552 scatters the light in the pulse train 554, the intervals between pulses in a return pulse train 556 are compressed in accordance with the velocity of the vehicle 552 relative to the vehicle 550.

On the other hand, a vehicle 560 is moving substantially away from the vehicle 550 in the scenario of FIG. 15. Accordingly, when the vehicle 560 scatters the light in the pulse train 554, the intervals between pulses in a return pulse train 562 are expanded in accordance with the velocity of the vehicle 560 relative to the vehicle 550.

In the scenario of FIG. 16, a vehicle 570 is moving in a direction substantially perpendicular to the forward-facing direction of the vehicle 550. The vehicle 570 can be moving along a perpendicular street when the vehicle 550 is approaching, or is stopped at, an intersection. The vehicle 550 emits the pulse train 554 at an angle α relative to direction of the vehicle 570. The vehicle 570 scatters the pulse train 554, and the intervals between adjacent pulses in a return pulse train 574 are compressed. If the frequency shift between the pulse trains 554 and 574 yields a velocity measurement $v_L$ along a straight line between the vehicles 550 and 570, the velocity of the vehicle 570 in the direction of travel can be calculated as $v=v_L/\cos(\alpha)$.

Although the targets in the example scenarios of FIGS. 14-16 are vehicles, in general the lidar system of this disclosure can determine the velocity of any target such as a person, a bicycle, an animal, etc.

Figure 17:
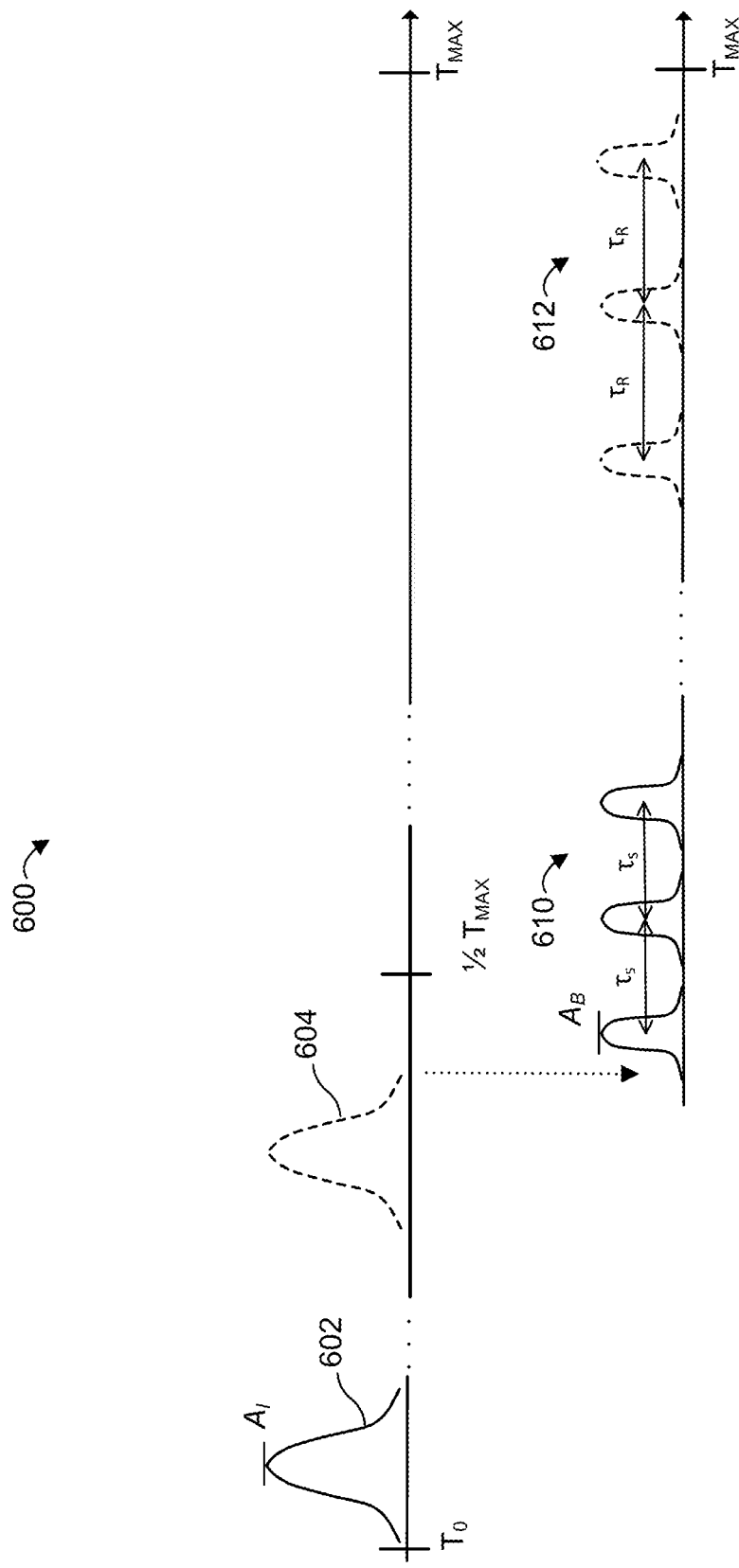
FIG. 17 is a timing diagram of an example ranging event during which the dual-mode lidar system of FIG. 1 can emit pulses to determine the distance to, and the velocity of, a target.

FIG. 17 is a timing diagram of an example ranging event 600 of duration $T_{MAX}$. The time $T_{MAX}$ can correspond to the time it takes a pulse to travel the maximum distance $R_{MAX}$ and back to the dual-mode lidar system. The dual-mode lidar system first operates in the distance-detection mode and generates an outbound pulse 602. The target scatters some of the light in the outbound pulse 602, and the system detects a return signal 604. The lidar system then detects a distance to the target based on the timing of the return signal 604. In this case, the return signal 604 arrives at the lidar system before $T_{MAX}/2$, and thus there is sufficient time for the lidar system to operate in the velocity-detection mode within the same ranging event. Processing this and other conditions for transitioning to the velocity-measurement mode is discussed in more detail with reference to the method of FIG. 24.

The dual-mode lidar system accordingly generates a series of pulses 610, referred to below as the "pulse train." There is an equal separation $\tau_s$ between successive pulses in this example, defining a constant pulse repetition frequency (PRF). The pulse train 610 can be emitted immediately upon receipt of the return pulse 604 or in response to other conditions, as discussed below. The dual-mode lidar system then can detect the velocity of the target based on the difference between $\tau_s$ and the equal separation $\tau_R$ between successive pulses of a return pulse train 612.

In an example implementation, the pulse train 610 includes ten pulses having a pulse repetition frequency of at least 10 MHz. In another implementation, the pulse train 610 includes more than ten pulses. Each of the pulses in the pulse train 610 can have the pulse duration of less than 10 ns, for example.

In an example scenario, the relative speed between a target and lidar system is v=45 m/s (=100 mph). The time interval between successive pulses in pulse burst is τ=1 ns; the pulse repetition frequency is f=1/τ=1 GHz; and the relative distance moved between successive pulses: Δd=(45 m/s)×(1 ns)=45 nm. The change in time interval between successive pulses: Δτ=(2×Δd)/c=0.3 fs, and the change in frequency between transmitted and received pulses: $\Delta f=(\Delta\tau)/\tau^2=300$ Hz. Because it is generally easier to detect a frequency shift of 300 Hz than a time-domain shift of 0.3 fs, a dual-model lidar system can process pulse-frequency characteristics in frequency domain. However, both frequency-domain and time-domain approaches are discussed below.

Figure 18A:
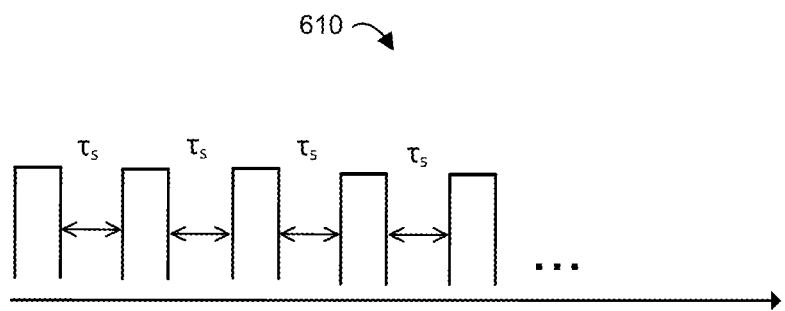
FIG. 18A illustrates an example pulse train with equal intervals between successive pulses, which the lidar system of FIG. 1 can generate to determine the velocity of a target.
Figure 18B:
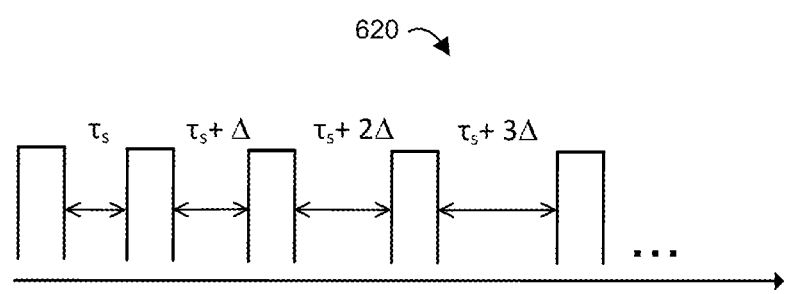
FIG. 18B illustrates an example "chirped" pulse train with increasing intervals between successive pulses, which the lidar system of FIG. 1 can generate to determine the velocity of a target.
Figure 18C:
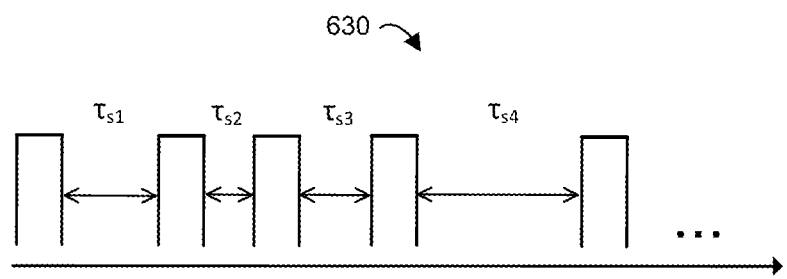
FIG. 18C illustrates an example pulse train with random intervals between successive pulses, which the lidar system of FIG. 1 can generate to determine the velocity of a target.

For further clarity, FIGS. 18A-C illustrate several example patterns according to which a pulse train can be transmitted. FIG. 18A first illustrates an example pulse train 610 in which successive pulses are separated by a constant time interval $\tau_s$. FIG. 18B then illustrates an example "chirped" pulse train with increasing intervals between successive pulses, $\tau_s$, $\tau_s+\Delta$, $\tau_s+2\Delta$, $\tau_s+3\Delta$, etc. More generally, a chirped signal can have an increasing PRF or a decreasing PRF, and the intervals can change according to any suitable principle, such as an exponential increase in time intervals between successive pulses.

Next, FIG. 18C illustrates an example pulse train with pseudo-random intervals between successive pulses, $\tau_{s1}$, $\tau_{s2}$, $\tau_{s3}$, etc. In one such implementation, a dual-mode lidar system generates pseudo-random intervals using certain properties of mode-locked lasers such as vertical external cavity semiconductor lasers (VECSELs) or mode-locked integrated external-cavity surface emitting lasers (MIXSELs). As a more specific example, a MIXSEL can produce a pseudo-random pulse train at a very high frequency (e.g., at 0.5 GHz to 50 GHz rate) upon activation, and the dual-mode lidar system can store the "signature," or the particular sequence of intervals in the first N pulses of the sequence, of an outbound pulse train. The dual-mode lidar system then can detect whether a return pulse train includes this signature, in its original form or as transformed due to the Doppler effect. In another implementation, the dual-mode lidar system is configured with a particular sequence $\tau_{s1}$, $\tau_{s2}$, $\tau_{s3}$, etc. defining a persistent signature. In any case, signatures imparted to pulse trains can reduce the probability of cross-talk and otherwise improve reliability of detection.

Generally speaking, a dual-mode lidar system can obtain pulse-frequency characteristics of emitted and received pulse trains using analog and/or digital signal processing techniques. These techniques can be implemented in hardware, firmware, software, or any suitable combination thereof. The calculations can be carried out in frequency domain or time domain, depending on the particular pulse-frequency characteristics used.

Figure 19:
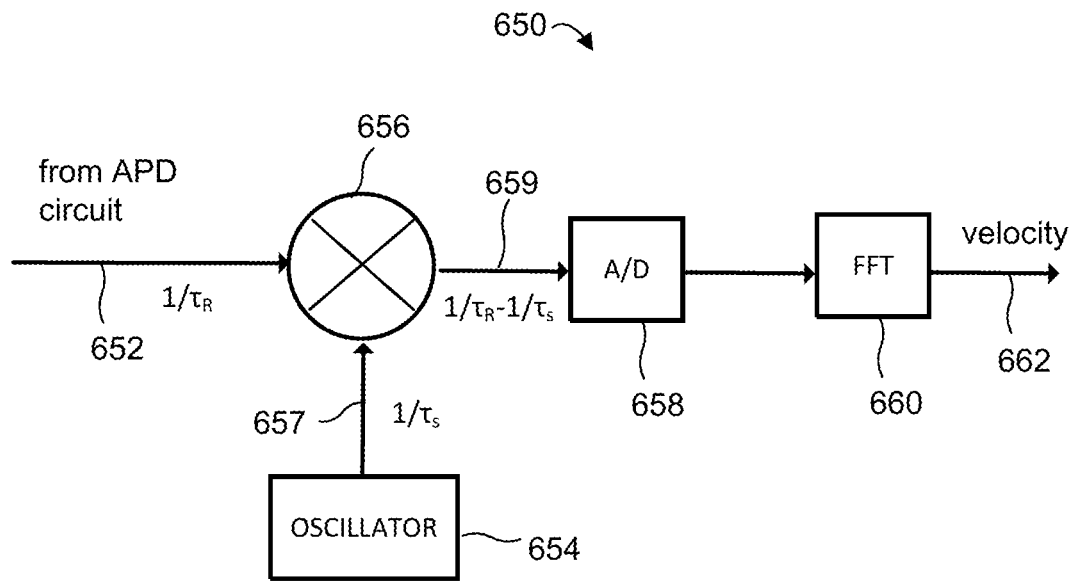
FIG. 19 is a block diagram of an example module for extracting a signal representative of a velocity of a target using a heterodyne technique, which can be implemented in the lidar system of FIG. 1.

FIG. 19 illustrates an example circuit 650 that a lidar system can implement to determine the velocity of a target in the frequency domain using a heterodyne technique. The circuit 650 includes a mixer element 656 that receives an electrical signal 657 corresponding to the series of emitted pulses (e.g., the pulse train 610 of FIG. 17). The mixer element 656 can receive this electrical signal from an oscillator 654, for example. The mixer element 656 also receives an input signal 652 that corresponds to the series of scattered pulses (e.g., the return pulse train 612 of FIG. 17). Referring back to FIGS. 12 and 13, the input signal 652 can correspond to the output of the gain circuit 512, i.e., the output of the APD 502 amplified by the TIA 510 and processed by the gain circuit 512. The mixer element 656 electrically mixes these inputs to generate a mixed output signal 659.

The output signal 659 is an electrical signal with one or more frequencies that corresponds to the velocity of the vehicle. In the example of FIG. 19, the output signal 659 is provided to an analog-to-digital converter (ADC) 658 and then to an FFT module 660. The FFT module 660 can generate a velocity signal 662 that represents the relative velocity of the target.

Figure 20A:
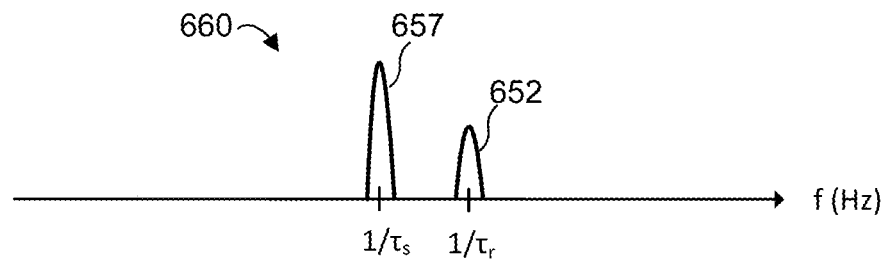
FIGS. 20A and 20B illustrate a relationship between signals corresponding to the emitted pulse train and the velocity of the vehicle, in frequency domain.
Figure 20B:
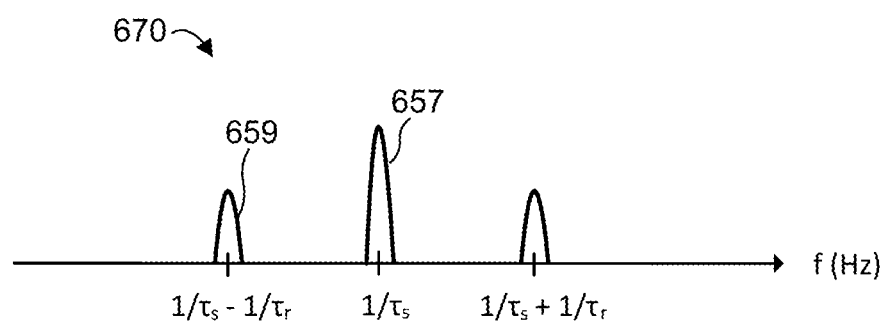

For clarity, FIGS. 20A and 20B illustrate the relationships between the signals of FIG. 19 in frequency domain: FIG. 20A illustrates the signals 657 and 652 in frequency domain, and FIG. 20B illustrates the results of frequency mixing.

In other implementations, electrical signals corresponding to received pulse train can be processed in time domain. Generally speaking, a signal first can be digitized using comparators, TDCs, etc., a time or frequency characteristic of the digitized electrical signal can be determined, and the determined time or frequency characteristic can be compared with the corresponding characteristic of the emitted pulse train.

Figure 21:
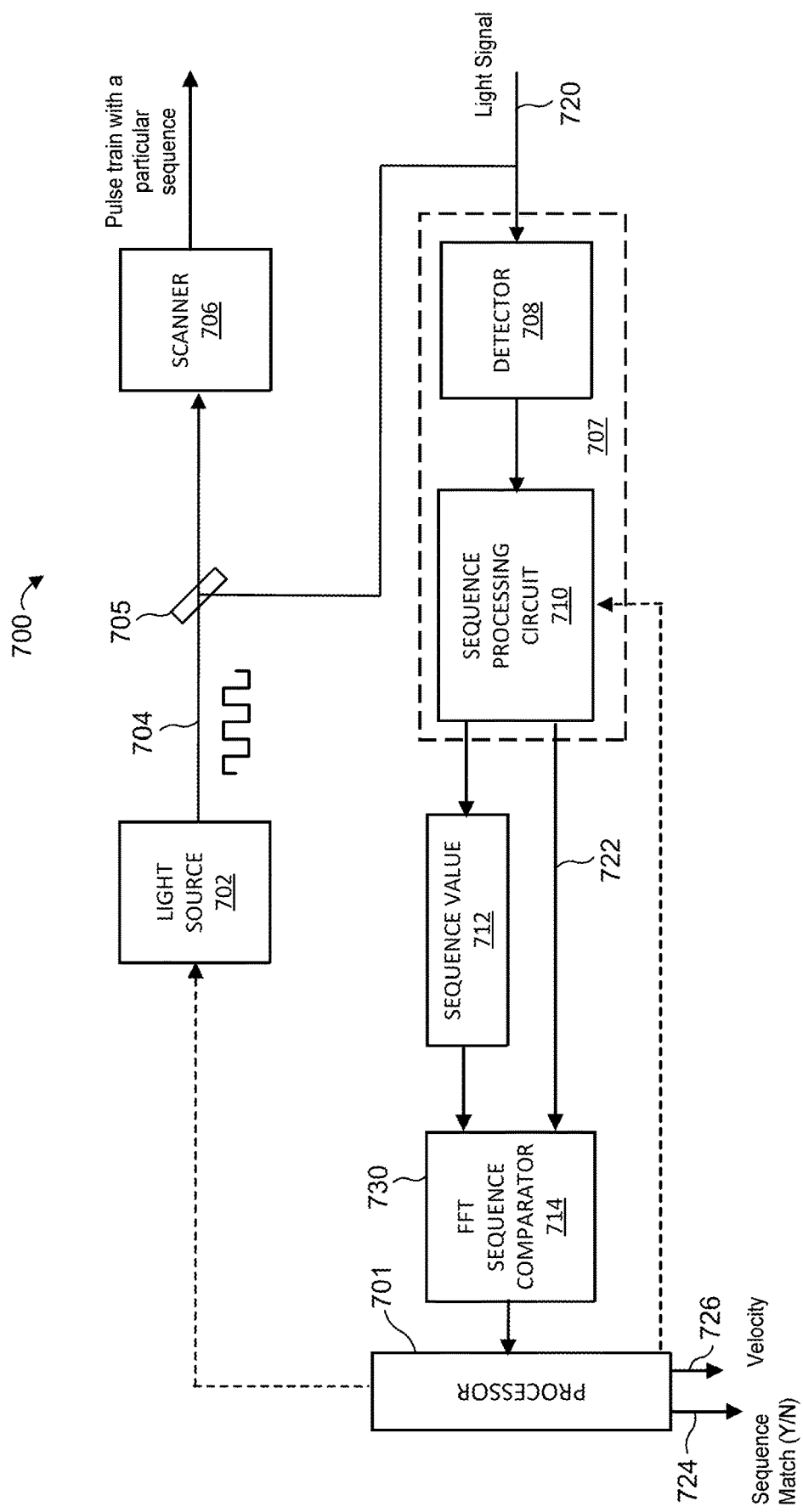
FIG. 21 is a diagram of an example circuit that can be implemented in the system of FIG. 1 to encode an outbound pulse train with a certain pattern and determine the pattern encoded in a return pulse train.

FIG. 21 is a diagram of an example circuit 700 that can be implemented in the system of FIG. 1 or FIG. 3, for example, to impart a signature to a pulse train, record the signature of the outbound pulse train, use the recorded signature to detect return light corresponding to the outbound pulse train, and detect the change in pulse-frequency characteristics to determine the velocity of the target.

A controller 701 can provide a control signal to a light source 702 (or, in another implementation, an optical modulator coupled to the light source 702) to cause the light source 702 to output a pulse train having particular pulse-frequency characteristics. The controller 701 in general can cause the light source 702 to output a pulse train 704 with a constant PRF, an increasing PRF, a decreasing PRF, a pseudo-random PRF, etc. However, the implementation of FIG. 21 is particularly suitable for those implementations where the PRF is pseudo-random.

Some of the energy of the output pulse train 704 can be directed to a receiver 707 by an optical element 705. The receiver 707 includes a detector 708 and a sequence processing circuit 710. The same detector 708 and sequence processing circuit 710 may be used to process both the generated outbound pulse train and the return pulse train. In another implementation, separate detectors may be used for outbound and inbound signals. Yet in another implementation, separate detectors as well as separate sequence processing circuits may be used to process outbound and inbound signals.

The sequence processing circuit 710 may determine time intervals between successive pairs of the first N peaks of the pulse train and store these intervals in a memory element such as a sequence value register 712. For example, referring to FIG. 22A, the sequence processing circuit 710 can detect the rising edge and the falling edge for each of the pulses 750A-D. The processing in this example can rely on a single threshold value 770. Upon detecting the sequence of values $\{t_{1R}, t_{1F}, t_{2R}, t_{2F}, t_{3R}, t_{3RF}, \ldots\}$, the circuit 700 can determine the time intervals between the successive pulses by calculating the intervals between the respective rising or falling edges, e.g., $t_{1R}$-$t_{2R}$, $t_{2R}$-$t_{3R}$, etc. and store these values in a sequence value register 712.

Referring back to FIG. 21, when a light signal 720 arrives at the detector 708, the processor 701 may generate a different control signal to instruct the sequence processing circuit 710 to not store the determined sequence in the sequence value register 712 and instead provide the output as a determined sequence 722 to an FFT sequence comparator 730. The FFT sequence comparator 730 may be implemented a separate processing unit that performs comparisons using hardware, firmware, software, or any suitable combination of hardware, firmware, or software. In a different implementation, the FFT sequence comparator 730 may be a software routine stored in the memory of the processor 701. The processor 714 processes the light signal 720 as a return pulse train corresponding to the output pulse train 704 only if the value stored in the sequence value register 712 matches the determined sequence 722, adjusted for the Doppler effect. The processor 701 can output an indication 724 of whether the determined sequence 722 corresponds to the output pulse train 704, and an indication of velocity 726.

Figure 22:
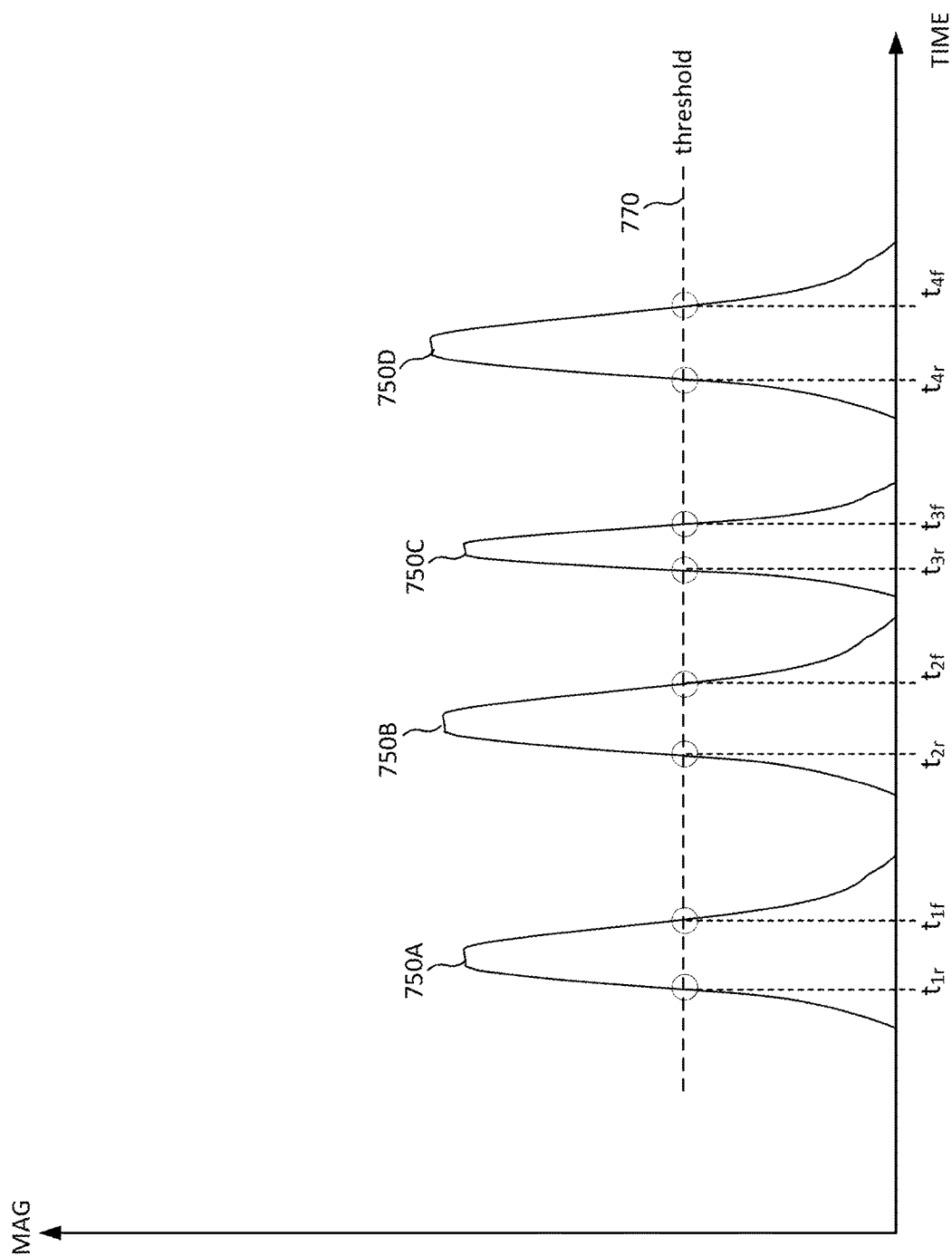
FIG. 22 schematically illustrates detecting rising and falling edges of pulses making up a pulse train that can be generated in the lidar system of FIG. 1.
Figure 23:
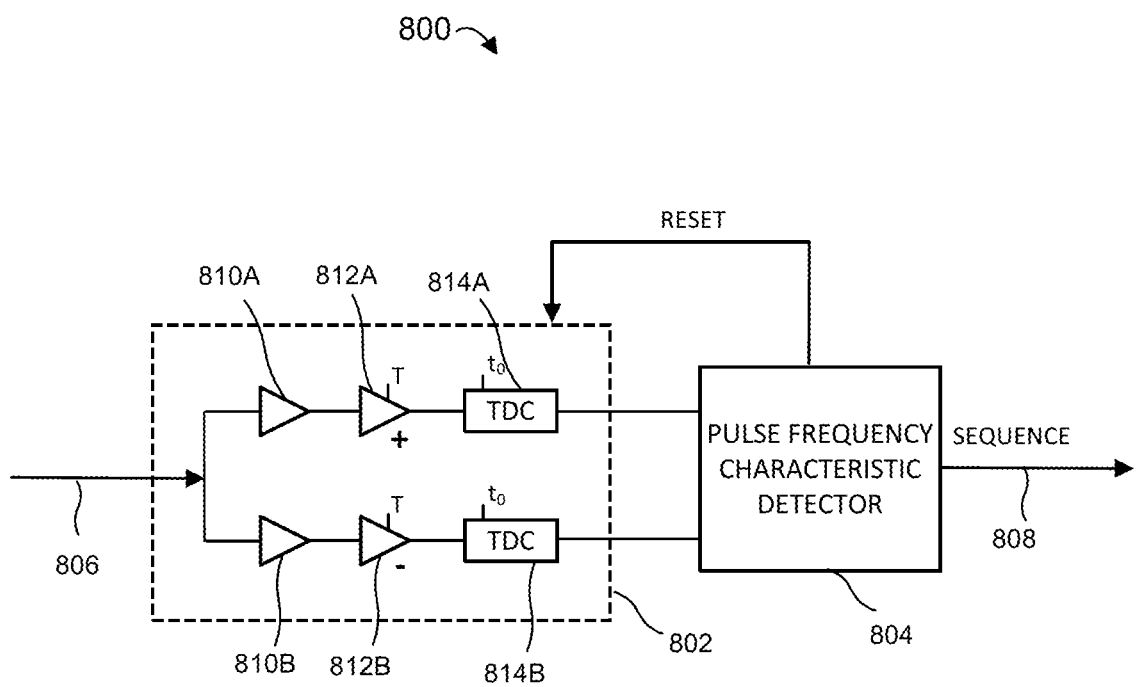
FIG. 23 is a block diagram of an example circuit that uses time-to-digital converters (TDCs) to determine the pattern of a pulse train.

FIG. 23 illustrates an example digital circuit 800 that can detect time intervals between successive pulses in a sequence such as the sequence of FIG. 22. An edge detection circuit 802 includes an amplifier 810A and a comparator 812A configured to trigger when the rising edge of a pulse in a pulse train reaches the threshold value T, and an amplifier 810B and a comparator 812B configured to trigger when the falling edge of the pulse reaches the threshold value T. The output of the comparator 812A is coupled to a time-to-digital converter (TDC) 814A to detect the number of clock cycles since time $t_0$, and the output of the comparator 812B is coupled to a TDC 814B to detect the number of clock cycles since time $t_0$. A pulse frequency characteristic detector 804 can include a register to store a certain number of values and the logic to reset component 802.

In operation, the edge detection circuit 802 receives an electric signal 806, such as the pulse train of FIG. 22. After the edge detection circuit 802 detects the rising edge of the first pulse in the input signal 806 reaching the threshold value T as well as the falling edge of the first pulse in the input signal 806 reaching the threshold value T, the pulse frequency characteristic detector 804 can store the corresponding time values (e.g., $t_{1R}$ and $t_{1F}$ illustrated in FIG. 22) in a memory and supply a reset signal to the edge detection circuit 802, so that the edge detection circuit 802 can detect the timing of the rising and the falling edges of the next pulse in the pulse train. After processing N pulses in the train, the pulse frequency characteristic detector 804 can output a sequence 808 in the format $\{t_{1R}, t_{1F}, t_{2R}, t_{2F}, t_{3R}, t_{3RF}, \ldots\}$, $\{t_{1R}\text{-}t_{2R}, t_{2R}\ t_{3R}, \ldots\}$, or any other suitable format. Referring back to FIG. 21, the digital circuit 800 can operate as the sequence processing circuit 710, for example, to output the sequence stored in the register 712 and the sequence 722.

Figure 24:
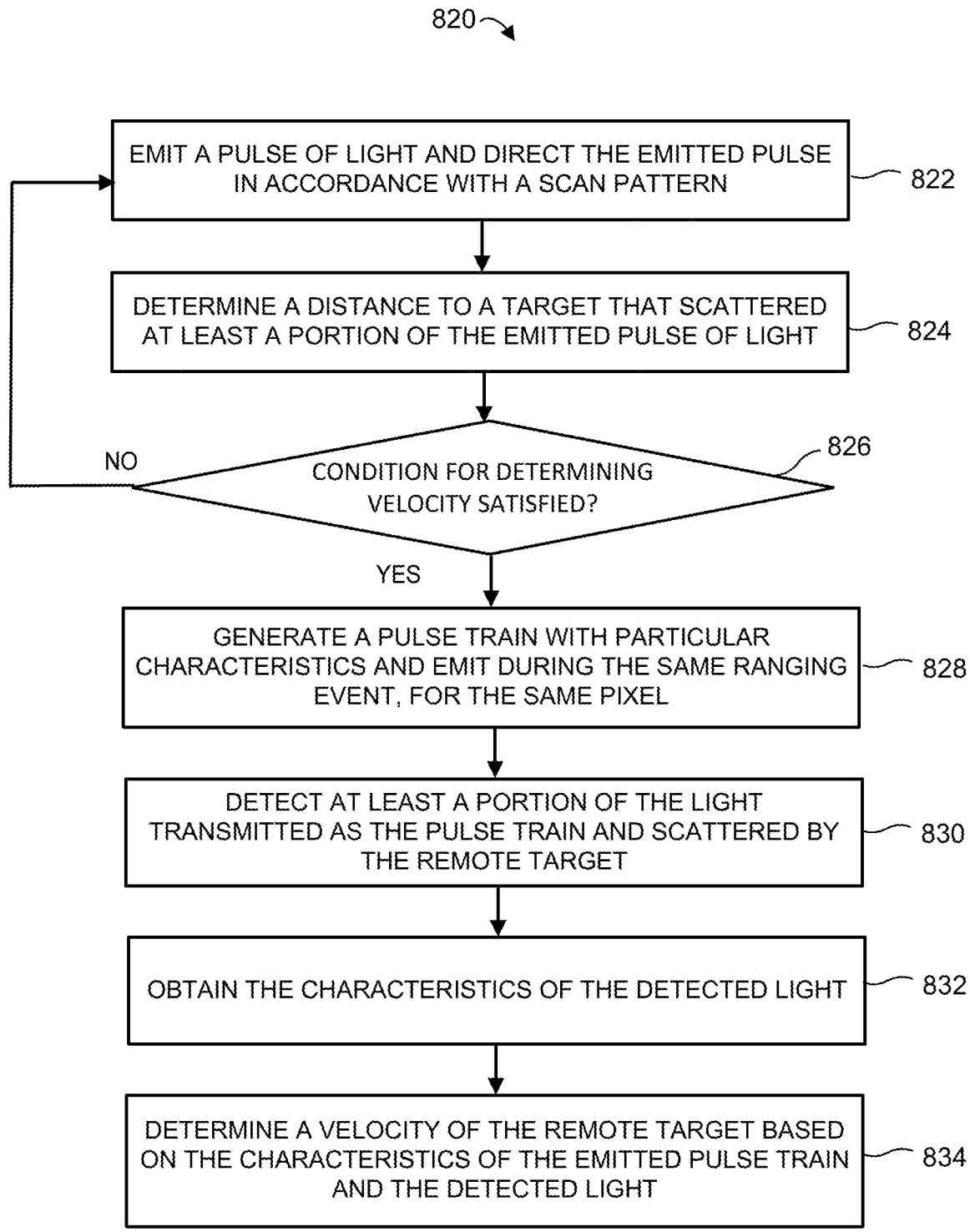
FIG. 24 is a flow diagram of an example method for determining a distance to a target and the velocity of the target, which can be implemented in the lidar system of this disclosure.

Next, FIG. 24 illustrates a flow diagram of an example method 800 for determining a distance to a target and the velocity of the target. The method 800 can be implemented in the controller 150 of FIG. 1, the controller 306 of FIG. 10, the controller 372 of FIG. 11, or another suitable processing hardware.

At block 822, a pulse of light is emitted and directed in accordance with the scan pattern, in the distance-determination operational mode. The distance to the target that scattered the emitted pulse of light is determined at block 824, using the time when the return from the emitted pulse of light is detected. Next, if it is determined at block 826 that one or more conditions for transitioning to the second mode to determine the velocity has been satisfied, the flow proceeds to block 828.

In one example implementation, the dual-mode lidar system at block 826 determines whether the distance to the target is greater than a certain maximum distance $D_{MAX}$. The maximum distance $D_{MAX}$ can be one half of the $R_{MAX}$ of the dual-model lidar system, when the system determines the distance and the velocity during the same ranging event. When the target is disposed more than $D_{MAX}$ meters away, there may not be sufficient time to send out a pulse train and receive a return signal; moreover, targets more than $D_{MAX}$ meters away may not be as important as nearby objects. More generally, the dual-mode lidar system can be configured to measure the velocity of the target only for certain distance ranges.

In an embodiment, a dual-mode lidar system also can detect whether the distance to the target is less than a certain minimum distance $D_{MIN}$. If the distance to the target is less than $D_{MIN}$, the system can reduce the pulse energy of the pulses in the pulse train. For example, when it is determined that the target within 20 m, the system can reduce the energy to approximately 10% of the value applied to pulse train at other distances. The dual-mode lidar system in this manner can improve eye safety as well as power usage, without losing so long as the pulse train has sufficient energy for the receiver when scattered from a nearby target.

More generally, once the distance to the target is determined at block 824, one or more parameters of the pulse train to be used for velocity measurement can be selected in view of the determined distance. In addition to modifying pulse energy as discussed above, a dual-mode lidar system can select the number of pulses in view of the distance: for example, the system can include fewer pulses in each pulse train when the target is closer, and more pulses in each pulse train when the target is farther away. Further, the system can modify the width of pulses included in the pulse train in view of the distance so that shorter-duration pulses are transmitted when the target is closer, for example.

In another example implementation, the dual-mode lidar system determines whether the time remaining in the ranging event is sufficient to determine the velocity of the target using a pulse train. For example, the dual-mode lidar system can determine whether at least half of the maximum ranging event remains.

Additionally or alternatively, the dual-mode lidar system at block 826 can determine, or receive an appropriate indication from another controller, whether the target is of a type for which velocity determination is relevant. For example, the vehicle controller 372 (see FIG. 11) can determine that a certain region of interest within the FOR includes a vehicle, a pedestrian, a bicycle, or another object of a dynamic or moving type using a classifier. When the dual-mode lidar system scans this region of interest, both distance and velocity measurements can be conducted. On the other hand, when the classifier in the vehicle controller 372 determines that a certain region within the FOR includes a building, a tree, a sign, a mailbox, a highway divider, or another object of a static type etc., the dual-mode lidar system can conduct only distance measurements when scanning this region.

Still further, it can be determined at block 826 whether the vehicle in which the dual-model lidar system operates is stopped. For example, the dual-model lidar system can be configured to determine velocity of cross traffic when the vehicle is stopped at an intersection. More generally, a the dual-model lidar system can be configured to carry out velocity measurements only at certain speeds (e.g., 0 to 20 mph).

In another implementation, the dual-mode lidar system is configured to determine velocities only for certain scan angles. Accordingly, at block 826, it can determined whether the horizontal scan angle is within a certain predefined range, the vertical scan angle is within a certain predefined range, or both. A suitable horizontal angular range for determining velocities in an example implementation is a 20-degree segment centered at the front-facing direction when the horizontal FOR spans 60 degrees, when the vehicle is in motion. A suitable vertical angular range for determining velocities in an example implementation are the upper 15 degrees when the vertical FOR spans 30 degrees because the lower portion of the FOR generally covers the road. In one implementation, the dual-mode lidar system dynamically determines which portion of the FOR covers the ground and operates in the velocity-measurement mode only for the above-ground portion of the FOR.

As discussed above with reference to FIG. 3, a dual-mode lidar system can operate in a two-eye mode with an area of overlap between the two FORs. When scanning the area of overlap, this dual-mode lidar system can determine distances to targets using one eye and determine velocities of targets using the other eye. When scanning other areas, the dual-mode lidar system can determine only distances, for example. In this manner, an eye of the dual-mode lidar system can utilize the entire duration of a ranging event to determine velocities, albeit only for the portion of the FOR where the other eye determines distances.

With continued reference to FIG. 24, a pulse train is generated with particular pulse-frequency characteristics is generated at block 828. The pulse train can be emitted upon receipt of the return signal corresponding to the pulse emitted at block 822, during the same ranging event. In another implementation, the pulse train is emitted during the next ranging event, so that pixels for which distance is determined are alternated with pixels for which velocity is determined. In still another implementation, velocity measurements are carried out once for every N pixels.

A return signal corresponding to the emitted pulse train and scattered by the target is detected at block 830. A pulse-frequency characteristic of the return pulse train is determined at block 832, and the velocity of the target is determined based on the determined characteristic at block 834. In some implementations, prior to determining the velocity of the target based on the Doppler effect, the dual-mode lidar system confirms that the signature the return pulse train corresponds to the signature imparted to the emitted pulse series. The dual-mode lidar system can discard the return pulse train when the signatures do not match after accounting for the Doppler effect.

In general, a dual-mode lidar system need not detect distance prior to detecting velocity in every implementation. Thus a dual-mode lidar system can be configured to first determine the velocity of the target and then determine the distance to the target.

Figure 25:
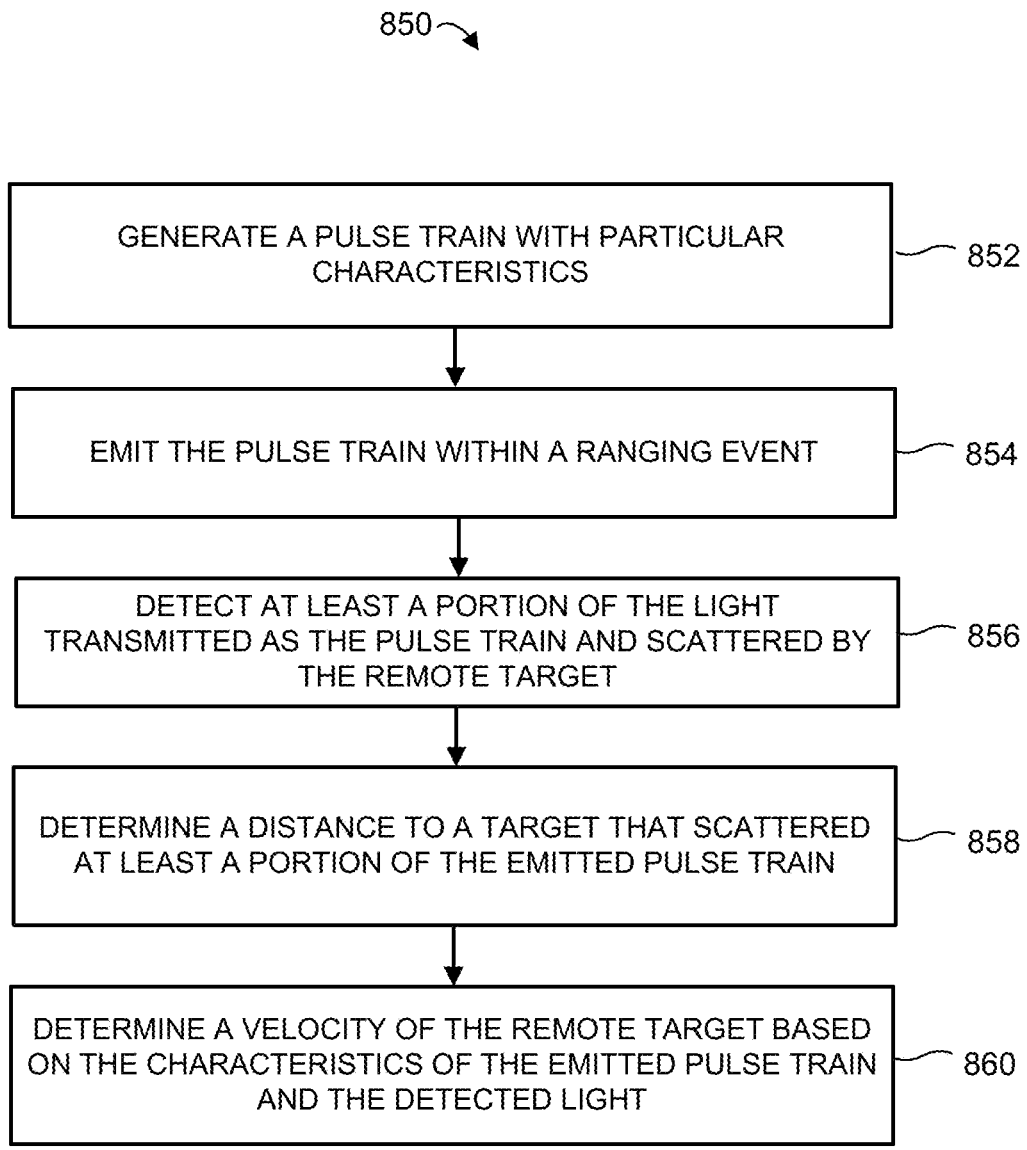
FIG. 25 is a flow diagram of an example method for determining a distance to a target and the velocity of the target, which can be implemented in the lidar system of this disclosure.

FIG. 25 is a flow diagram of an example method 850 for determining a distance to a target and the velocity of the target using a pulse train with a certain pulse-frequency characteristic, where the pulse train also operates as a single ranging pulse. The pulse train can be understood as defining a certain envelope as well as a sequence of individual pulse. Such a pulse train is generated at block 852 and emitted in accordance with the scan pattern at block 854. At least a portion of the light corresponding to the emitted pulse train is detected at block 856. The distance to the target is determined at block 858 using the time when the rising edge of the first pulse in the return pulse train reaches a certain level, for example. Referring back to FIG. 22, the time used for distance measurement can be $t_{1R}$. Next, at block 860, the velocity of the target is determined based on a comparison of pulse-frequency characteristics of the emitted pulse train and the received pulse train, using the techniques discussed above.

GENERAL CONSIDERATIONS

In some cases, a computing device may be used to implement various modules, circuits, systems, methods, or algorithm steps disclosed herein. As an example, all or part of a module, circuit, system, method, or algorithm disclosed herein may be implemented or performed by a general-purpose single- or multi-chip processor, a digital signal processor (DSP), an ASIC, a FPGA, any other suitable programmable-logic device, discrete gate or transistor logic, discrete hardware components, or any suitable combination thereof. A general-purpose processor may be a microprocessor, or, any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

In particular embodiments, one or more implementations of the subject matter described herein may be implemented as one or more computer programs (e.g., one or more modules of computer-program instructions encoded or stored on a computer-readable non-transitory storage medium). As an example, the steps of a method or algorithm disclosed herein may be implemented in a processor-executable software module which may reside on a computer-readable non-transitory storage medium. In particular embodiments, a computer-readable non-transitory storage medium may include any suitable storage medium that may be used to store or transfer computer software and that may be accessed by a computer system. Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs (e.g., compact discs (CDs), CD-ROM, digital versatile discs (DVDs), blue-ray discs, or laser discs), optical disc drives (ODDs), magneto-optical discs, magneto-optical drives, floppy diskettes, floppy disk drives (FDDs), magnetic tapes, flash memories, solid-state drives (SSDs), RAM, RAM-drives, ROM, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

In some cases, certain features described herein in the context of separate implementations may also be combined and implemented in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

While operations may be depicted in the drawings as occurring in a particular order, this should not be understood as requiring that such operations be performed in the particular order shown or in sequential order, or that all operations be performed. Further, the drawings may schematically depict one more example processes or methods in the form of a flow diagram or a sequence diagram. However, other operations that are not depicted may be incorporated in the example processes or methods that are schematically illustrated. For example, one or more additional operations may be performed before, after, simultaneously with, or between any of the illustrated operations. Moreover, one or more operations depicted in a diagram may be repeated, where appropriate. Additionally, operations depicted in a diagram may be performed in any suitable order. Furthermore, although particular components, devices, or systems are described herein as carrying out particular operations, any suitable combination of any suitable components, devices, or systems may be used to carry out any suitable operation or combination of operations. In certain circumstances, multitasking or parallel processing operations may be performed. Moreover, the separation of various system components in the implementations described herein should not be understood as requiring such separation in all implementations, and it should be understood that the described program components and systems may be integrated together in a single software product or packaged into multiple software products.

Various implementations have been described in connection with the accompanying drawings. However, it should be understood that the figures may not necessarily be drawn to scale. As an example, distances or angles depicted in the figures are illustrative and may not necessarily bear an exact relationship to actual dimensions or layout of the devices illustrated.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes or illustrates respective embodiments herein as including particular components, elements, functions, operations, or steps, any of these embodiments may include any combination or permutation of any of the components, elements, functions, operations, or steps described or illustrated anywhere herein that a person having ordinary skill in the art would comprehend.

The term "or" as used herein is to be interpreted as an inclusive or meaning any one or any combination, unless expressly indicated otherwise or indicated otherwise by context. Therefore, herein, the expression "A or B" means "A, B, or both A and B." As another example, herein, "A, B or C" means at least one of the following: A; B; C; A and B; A and C; B and C; A, B and C. An exception to this definition will occur if a combination of elements, devices, steps, or operations is in some way inherently mutually exclusive.

As used herein, words of approximation such as, without limitation, "approximately," "substantially," or "about" refer to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as having the required characteristics or capabilities of the unmodified feature. In general, but subject to the preceding discussion, a numerical value herein that is modified by a word of approximation such as "approximately" may vary from the stated value by ±0.5%, ±1%, ±2%, ±3%, ±4%, ±5%, ±10%, ±12%, or ±15%.

As used herein, the terms "first," "second," "third," etc. may be used as labels for nouns that they precede, and these terms may not necessarily imply a particular ordering (e.g., a particular spatial, temporal, or logical ordering). As an example, a system may be described as determining a "first result" and a "second result," and the terms "first" and "second" may not necessarily imply that the first result is determined before the second result.

As used herein, the terms "based on" and "based at least in part on" may be used to describe or present one or more factors that affect a determination, and these terms may not exclude additional factors that may affect a determination. A determination may be based solely on those factors which are presented or may be based at least in part on those factors. The phrase "determine A based on B" indicates that B is a factor that affects the determination of A. In some instances, other factors may also contribute to the determination of A. In other instances, A may be determined based solely on B.

What is claimed is:

1. A method comprising:
   emitting, by a light source of a lidar system, a pulse of light;
   detecting, by a receiver of the lidar system, at least a portion of the emitted pulse of light scattered by a target located a distance from the lidar system;
   determining, by a processor of the lidar system, the distance from the lidar system to the target based at least in part on a round-trip time of flight for the emitted pulse of light to travel from the lidar system to the target and back to the lidar system; and
   if (i) the distance to the target is greater than a particular maximum distance or (ii) at least one of a horizontal scan angle or a vertical scan angle is outside a respective particular range within a field of regard of the lidar system, then refraining from emitting a series of pulses of light, otherwise:
   emitting, by the light source, the series of pulses of light, the series of emitted pulses of light having particular pulse-frequency characteristics;
   detecting, by the receiver, at least a portion of the series of emitted pulses of light scattered by the target;
   comparing, by a comparison module, the pulse-frequency characteristics of the series of emitted pulses of light with corresponding pulse-frequency characteristics of the detected series of scattered pulses of light to determine a velocity of the target with respect to the lidar system.

2. The method of claim 1, wherein emitting the series of pulses is in response to determining the distance from the lidar system to the target.

3. The method of claim 1, wherein comparing the pulse-frequency characteristics comprises:
   electrically mixing an electrical signal corresponding to the series of emitted pulses of light with an electrical signal corresponding to the detected series of scattered pulses of light to produce a mixed output signal;
   determining one or more intermediate frequencies of the mixed output signal; and
   determining the velocity of the target with respect to the lidar system based on the one or more intermediate frequencies.

4. The method of claim 1, wherein comparing the pulse-frequency characteristics comprises:
   digitizing an electrical signal corresponding to the detected series of scattered pulses of light;
   determining a time or frequency characteristic of the digitized electrical signal; and
   comparing the determined time or frequency characteristic with a corresponding time or frequency characteristic of the series of emitted pulses of light to determine the velocity of the target with respect to the lidar system.

5. The method of claim 1, wherein the series of emitted pulses of light comprises greater than or equal to 10 pulses having a pulse repetition frequency of greater than 10 MHz, each of the pulses having a pulse duration of less than 10 ns.

6. The method of claim 1, wherein the pulse-frequency characteristics of the series of emitted pulses of light comprise a constant pulse repetition frequency.

7. The method of claim 1, including emitting the series of pulses of light only if a vehicle in which the lidar system operates is stopped.

8. The method of claim 1, further comprising:
determining a type of object to which the target corresponds;
emitting the series of pulses of light if the determined type corresponds to a dynamic type; and
refraining from emitting the series of pulses of light if the determined type corresponds to a static type.

9. The method of claim 1, further comprising:
receiving an indication of a region of interest within the field of regard of the lidar system; and
refraining from emitting the series of pulses of light if the target is not located within the region of interest.

10. The method of claim 1, further comprising reducing a pulse energy of the series of emitted pulses of light if the distance to the target is less than a particular minimum distance.

11. The method of claim 1, further comprising:
detecting another series of pulses of light emitted by another lidar system;
determining that the pulse-frequency characteristics of the series of emitted pulses of light do not match corresponding pulse-frequency characteristics of the another series of pulses of light; and
disregarding the other series of pulses of light.

12. A lidar system comprising:
a light source configured to emit a pulse of light;
a receiver configured to detect at least a portion of the emitted pulse of light scattered by a target located a distance from the lidar system; and
a processor configured to determine the distance from the lidar system to the target based at least in part on a round-trip time of flight for the emitted pulse of light to travel from the lidar system to the target and back to the lidar system;
wherein if (i) the distance to the target is greater than a particular maximum distance or (ii) at least one of a horizontal scan angle or a vertical scan angle is outside a respective particular range within a field of regard of the lidar system, then the light source is further configured to refrain from emitting a series of pulses of light, otherwise:
the light source is further configured to emit a series of pulses of light having particular pulse-frequency characteristics;
the receiver is further configured to detect at least a portion of the series of emitted pulses of light scattered by the target; and
the lidar system further comprises a comparison module configured to compare the pulse-frequency characteristics of the series of emitted pulses of light with corresponding pulse-frequency characteristics of the detected series of scattered pulses of light to determine a velocity of the target with respect to the lidar system.

13. The lidar system of claim 12, wherein the light source comprises:
a pulsed laser diode configured to produce optical seed pulses; and
one or more optical amplifiers configured to amplify the optical seed pulses to produce the emitted pulses of light.

14. The lidar system of claim 12, wherein the light source comprises a direct-emitter laser diode configured to produce the emitted pulses of light.

15. The lidar system of claim 12, further comprising a scanner configured to scan the emitted pulses of light across the field of regard of the lidar system.

16. The lidar system of claim 15, wherein the scanner comprises one or more mirrors, wherein each mirror is mechanically driven by a galvanometer scanner, a resonant scanner, a microelectromechanical systems (MEMS) device, a voice coil motor, or a synchronous electric motor.

17. The lidar system of claim 15, wherein the scanner comprises:
a first mirror driven by a first galvanometer scanner that scans the emitted pulses of light along a first direction; and
a second mirror driven by a second galvanometer scanner that scans the emitted pulses of light along a second direction substantially orthogonal to the first direction.

18. The lidar system of claim 15, wherein the scanner comprises:
a first mirror configured to scan the emitted pulses of light along a first direction; and
a polygon mirror configured to scan the emitted pulses of light along a second direction substantially orthogonal to the first direction.

19. The lidar system of claim 12, wherein the receiver comprises an avalanche photodiode (APD) configured to receive light scattered by the target and produce an electrical current corresponding to the received light.

20. A method comprising:
emitting, by a light source of a lidar system, a series of pulses of light having particular pulse-frequency characteristics;
detecting, by a receiver of the lidar system, at least a portion of the series of emitted pulses of light scattered by a first target located a first distance from the lidar system;
determining, by a processor of the lidar system, the first distance from the lidar system to the first target based at least in part on a round-trip time of flight for the series of emitted pulses of light to travel from the lidar system to the first target and back to the lidar system; and
comparing, by a comparison module, the pulse-frequency characteristics of the series of emitted pulses of light with corresponding pulse-frequency characteristics of the detected series of scattered pulses of light to determine a velocity of the first target with respect to the lidar system,
wherein each of the emitting, the detecting, the determining, and the comparing occurs in a first instance to generate a value of a first pixel, the method further comprising, in a second instance:
emitting, by the light source, a single pulse of light;
detecting, by the receiver, at least a portion of the emitted pulse of light scattered by a second target located a second distance from the lidar system; and
determining, by the processor of the lidar system, the second distance from the lidar system to the second target based at least in part on a round-trip time of flight for the emitted pulse of light to travel from the lidar system to the second target and back to the lidar system to generate a value of a second pixel,
wherein each of the first pixel and the second pixel correspond to respective ranging events of equal duration.

21. The method of claim 20, wherein comparing the pulse-frequency characteristics includes:
   determining a time or frequency characteristic of an electrical signal corresponding to the detected series of scattered pulses of light; and
   comparing the determined time or frequency characteristic with a corresponding time or frequency characteristic of the series of emitted pulses of light to determine the velocity of the first target with respect to the lidar system.

22. The method of claim 20, further comprising not modulating a frequency of the light.

23. A method comprising:
   emitting, by a light source of a lidar system, a pulse of light;
   detecting, by a receiver of the lidar system, at least a portion of the emitted pulse of light scattered by a target located a distance from the lidar system;
   determining, by a processor of the lidar system, the distance from the lidar system to the target based at least in part on a round-trip time of flight for the emitted pulse of light to travel from the lidar system to the target and back to the lidar system;
   emitting, by the light source, a series of pulses of light having particular pulse-frequency characteristics, wherein the pulse-frequency characteristics of the series of emitted pulses of light comprise (i) an increasing pulse repetition frequency, (ii) a decreasing pulse repetition frequency, or (iii) a pseudo-random sequence of pulses of light having pseudo-random intervals of time between the pulses;
   detecting, by the receiver, at least a portion of the series of emitted pulses of light scattered by the target; and
   comparing, by a comparison module, the pulse-frequency characteristics of the series of emitted pulses of light with corresponding pulse-frequency characteristics of the detected series of scattered pulses of light to determine a velocity of the target with respect to the lidar system.

24. A method comprising:
   emitting, by a light source of a lidar system, a pulse of light;
   detecting, by a receiver of the lidar system, at least a portion of the emitted pulse of light scattered by a target located a distance from the lidar system;
   determining, by a processor of the lidar system, the distance from the lidar system to the target based at least in part on a round-trip time of flight for the emitted pulse of light to travel from the lidar system to the target and back to the lidar system;
   selecting, by the processor and in view of the determined distance to the target, one or more of: (i) a pulse energy of pulses in a series of pulses of light, (ii) a width of pulses in the series of pulses of light, and (iii) a number of pulses to be included in the series of pulses of light;
   emitting, by the light source, the series of pulses of light, the series of emitted pulses of light having particular pulse-frequency characteristics;
   detecting, by the receiver, at least a portion of the series of emitted pulses of light scattered by the target; and
   comparing, by a comparison module, the pulse-frequency characteristics of the series of emitted pulses of light with corresponding pulse-frequency characteristics of the detected series of scattered pulses of light to determine a velocity of the target with respect to the lidar system.

* * * * *